United States Patent
Shutske et al.

(10) Patent No.: US 7,919,508 B2
(45) Date of Patent: Apr. 5, 2011

(54) 3-PIPERIDINYLISOCHROMAN-5-OLS AS DOPAMINE AGONISTS

(75) Inventors: Gregory Shutske, Pittstown, NJ (US); Keith J. Harris, Chester, NJ (US); Kenneth J. Bordeau, Kintnersville, PA (US); Michael R. Angelastro, Bridgewater, NJ (US); Stanly John, Bridgewater, NJ (US); Joseph T. Klein, Neshanic Station, NJ (US); Jinqi Lu, Green Brook, NJ (US); Catherine Bomont, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 1056 days.

(21) Appl. No.: 11/552,169

(22) Filed: Oct. 24, 2006

(65) Prior Publication Data
US 2007/0099955 A1    May 3, 2007

Related U.S. Application Data

(63) Continuation of application No. PCT/US2005/014487, filed on Apr. 27, 2005.

(60) Provisional application No. 60/566,557, filed on Apr. 29, 2004.

(51) Int. Cl.
*A61K 31/452*    (2006.01)
*C07D 405/02*    (2006.01)

(52) U.S. Cl. ......... 514/320; 514/309; 546/148; 546/196

(58) Field of Classification Search .......... 514/320, 514/309; 546/196, 148
See application file for complete search history.

(56) References Cited

U.S. PATENT DOCUMENTS
6,004,982 A    12/1999    Stupczewski et al.

FOREIGN PATENT DOCUMENTS
WO    WO 98/34933    8/1988

*Primary Examiner* — Celia Chang
(74) *Attorney, Agent, or Firm* — Jiang Lin

(57) ABSTRACT

The present invention provides compounds of formula I:

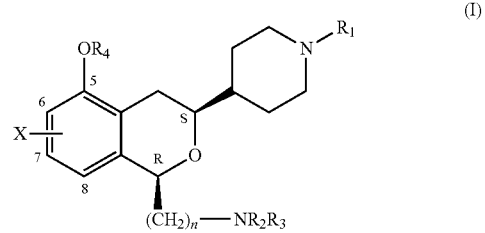

a stereoisomer or a pharmaceutically acceptable salt thereof, wherein the variables $R_1$, $R_2$, $R_3$, $R_4$, X and n are defined as defined herein. Additionally, a method for treating dopamine-related neurological disorders selected form the group consisting of neurological, psychological, cardiovascular, cognitive or attention disorders, substance abuse and addictive behavior, or a combination thereof, comprising administering to a patient in need of such treatment a therapeutically effective amount of compounds of formula I.

10 Claims, No Drawings

3-PIPERIDINYLISOCHROMAN-5-OLS AS DOPAMINE AGONISTS

CROSS-REFERENCE TO RELATED APPLICATIONS

This application is a continuation of International Application No. PCT/US2005/014487 filed on Apr. 27, 2005 which is incorporated herein by reference in its' entirety which also claims the benefit of priority of U.S. Provisional Appln. No. 60/566,557 filed on Apr. 29, 2004.

FIELD OF THE INVENTION

This invention relates generally to compounds and compositions for the treatment of central nervous system (CNS) disorders such as schizophrenia, Parkinsons' Disease, addiction, depression and the like. More specifically, the present invention relates to novel compounds which are selective dopamine agonists which turn on or enhance adenylate cyclase-linked receptors. These compounds are useful for treating the aforementioned disorders characterized by abnormal dopamine levels.

BACKGROUND OF THE INVENTION

Dopamine is an ubiquitous neurotransmitter found in the central nervous system (CNS) as well as in the peripheral nervous system of mammals. In the CNS, it is involved with motor function, perception, cognition, attention, arousal, motivation and emotion. In the peripheral nervous system, it is involved, for example, in the control of blood to the kidneys and in autonomic ganglion transmission.

It is now generally recognized that dopamine receptors in the CNS exist as five different receptors, designated as D1 through D5. Additionally, they are further classified as to whether they fall into the D1-like or D2-like family of receptors based upon their pharmacological differences. Accordingly, D1 and D5 are considered part of the D1 family of receptors, whereas D2, D3 and D4 are considered part of the D2 family.

Dopamine imbalance is believed to play a key role in a number of CNS-related disorders such as schizophrenia, Parkinson's disease, drug abuse, eating disorders and depression.

D1 receptors are positively linked to adenylate cyclase and are found in all areas of the human brain, with the frontal cortex and the substantia nigra pars compact a particularly rich with D1 receptors. D1 receptors are also found in the periphery, and have been identified in kidney and heart tissue. As such, disease states attributed to aberrations of the dopamine neuronal network could possibly be treated by drugs, which are selective for the D1 receptor. And, of particular interest are a class of drugs that would act as selective agonists at D1 receptors.

For instance D1 selective agonists have shown utility in treating Parkinson's disease. The loss of striatal dopamine within the basal ganglia, the region of the mammalian brain that is involved with motor control, has been established as the fundamental deficit in Parkinson's disease and primary to the etiology of that disease state. This deficiency is addressed via dopamine replacement therapy, primarily with L-DOPA (3,4-dihydroxyphenylalanine), which is converted to dopamine within the brain. Other compounds that act as agonists at the dopamine receptor have also been used to treat Parkinson's disease. Bromocriptine, the most widely used direct-acting dopamine agonist for the treatment of Parkinson's disease, is often administered with L-DOPA in order to lower dosages of the latter required to achieve the desired therapeutic response. Bromocriptine alone has been shown to relieve Parkinson's disease symptoms in some early Parkinson's disease patients, allowing for a delay in the onset of L-DOPA therapy. Chronic L-DOPA use is associated with a number of serious side effects and limitations, such as the development of dyskinesias, severe response fluctuations (on-off phenomenon) and diminishing efficacy during treatment.

Anti-schizophrenic drugs are postulated to exert their effects by blocking the dopamine receptors (i.e., acting as receptor antagonists), and consequently preventing excess receptor stimulation (G. P. Reynolds, TIPS, 13:116-121, 1992). However, these antipsychotic agents frequently produce undesirable side effects, the most common of which are the extrapyramidal effects that include bizarre involuntary movements and Parkinson-like states, as well as sedation and hypotension. Because of these often-severe side effects and the high incidence of patients unresponsive to dopamine blocking drugs, novel and improved therapies continue to be sought.

One complement to dopamine receptor antagonists for the treatment of schizophrenia has included the use of low doses of dopamine agonists, such as apomorphine and bromocriptine, which have been reported to produce antipsychotic effects, possibly due to preferential activation of dopamine presynaptic receptors resulting in decreased dopaminergic activity (M. Del Zompo et al, Progress in Brain Research, 65:41-48, 1986 and H. Y. Meltzer, Drug Development Research, 9:23-40, 1986). In addition, the dopamine D1-selective agonist, SKF 38393, when used in conjunction with the antipsychotic drug, haloperidol, a D2 antagonist, has been shown to ameliorate the undesired side effects of the haloperidol (M. Davidson et al., Arch Gen. Psychiatry, 47:190-191, 1990).

There is evidence that dopamine plays a role in the brain reward system. For example, animals trained to self-administer cocaine will increase their consumption of this drug after treatment with either a D1 or a D2 receptor antagonist, presumably in order to maintain the elevated dopamine levels responsible for the drug's euphorigenic and reinforcing properties (D. R. Britton et al, Pharmacology Biochemistry & Behavior, 39:911-915, 1991). The D1 agonist, SKF 38393, has also been reported to decrease food intake by rats, presumably by direct action of the drug on neural feeding mechanisms. Because of this interrelationship between dopamine and reward, dopaminergic agents would be useful for the treatment of substance abuse and other addictive behavior disorders, including cocaine addiction (A. L. Chausmer et al. Psychopharmacology, 159:145-153, 2002) nicotine addiction and eating disorders.

Affective disorders, the most common psychiatric disorders in adults, are characterized by changes in mood as the primary clinical manifestation, and result from a reduction in the central nervous system of certain biogenic amine neurotransmitters, such as dopamine, noradrenaline and serotonin. Currently available antidepressants work primarily by raising biogenic amine neurotransmitter levels, either by inhibiting their uptake or preventing their metabolism. No antidepressant drug to date, however, can substitute for electroconvulsive shock therapy for the treatment of severe, suicidal depression. Currently available drugs for treating affective disorders unfortunately suffer from delayed onset of action, poor efficacy, anticholinergic effects at therapeutic doses, cardiotoxicity, convulsions and the possibility of overdosing. A large number of clinically depressed individuals remain refractory to currently available therapies. A role for direct-acting dopamine agonists in antidepressant therapy has been suggested based on the effects observed for several dopamine agonists in various animal models (R. Muscat et al., Biological Psychiatry, 31:937-946, 1992).

A role for dopamine has also been established in cognition and attention mechanisms. Animal studies support the role of dopamine in attention-related behaviors involving search and exploratory activity, distractibility, response rate, discriminability and the switching of attention. Treatment of cognitive impairment and attention deficit disorders via dopamine-based therapy has been proposed and is under active investigation (A. Nieoullon, Progress in Neurobiology, 67:53-58 (2002) and T. Sawaguchi and P. S. Goldman-Rakic, Science, 252:947-940 (1991); and P. S. Goldman-Rakic et al., Science, 287:2020-2022 (2000)).

In addition, dopamine has been identified with a number of effects in the periphery, and has been used in the treatment of shock, congestive heart failure and acute renal failure. Stimulation of the peripheral D1 receptors causes vasodilation, particularly in the renal and mesenteric vascular beds where large numbers of these receptors are found. The utility of dopamine has been limited, however, by its ability to cause vasoconstriction at higher concentrations, presumably due to its secondary effects on adrenergic receptors, and by its emetic effects due to peripheral D2 stimulation. Agents selective for the peripheral D1 receptors appear to offer significant advantages over treatments used currently for these and other related disorders (M. F. Lokhandwala, Drug Development Research, 113:123-124 (1987)).

Certain compounds within the scope of the present invention are generically disclosed and claimed in U.S. Pat. No. 6,004,982, the entire disclosure of which is herein incorporated by reference. For example, certain (4-piperidinyl)-1H-2-benzopyrans) were disclosed therein to be useful as antipsychotics. The present invention represents single enatiomers of piperidinylisochromans as dopamine agonists.

SUMMARY OF THE INVENTION

A compound of formula I

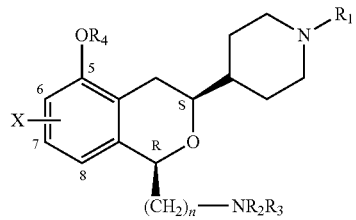

wherein
R$_1$ is selected from the group consisting of hydrogen, phenoxycarbonyl, C$_{1-6}$alkoxycarbonyl, benzyloxycarbonyl, naphthyloxycarbonyl, phenylcarbamoyl, phenylcarbamoylC$_{1-6}$alkyl, biphenylcarbamoyl, phenyl C$_{1-6}$alkylcarbamoyl, naphthylcarbamoylC$_{1-6}$alkyl, N-phenyl-N—C$_{1-6}$alkycarbamoyl, C$_{1-6}$alkyl and C$_{1-6}$dialkylcarbamoyl, C$_{2-6}$alkenyl and C$_{2-6}$dialkenylcarbamoyl, diphenylcarbamoyl, heteroarylcarbamoylC$_{1-6}$alkyl, phenylcarbonyl, biphenylcarbonyl, C$_{1-6}$alkylcarbonyl, morpholinylcarbonyl, piperidinylcarbonyl, pyrrolidinylcarbonyl, phenothiazinylcarbonyl, phenylsulfonyl, diphenylsulfonyl, naphthylsulfonyl, C$_{1-10}$alkylsulfonyl, naphthyl C$_{1-6}$alkylsulfonyl, C$_{1-6}$perfluoroalkylsulfonyl, diphenylC$_{1-6}$alkylsulfonyl, benzenesulfonyl, C$_{1-6}$dialkylaminosulfonyl, diphenylC$_{1-6}$alkyl, benzyl, phenylC$_{2-6}$alkyl, naphthyl C$_{1-6}$alkyl; C$_{3-6}$cycloalkylC$_{1-6}$alkyl, phenylC$_{1-6}$alkenyl, heteroarylC$_{1-6}$alkyl, α-carboxybenzyl, phenylcarbonylC$_{1-6}$alkyl, hydroxyC$_{1-6}$alkyl, biphenylC$_{1-6}$alkyl, C$_{1-6}$alkyl, phenoxyphenylC$_{1-6}$alkyl, phenylureaC$_{1-6}$alkyl, indanyl, wherein benzyl and phenyl are optionally substituted with one or two substituents each independently selected from the group consisting of C$_{1-6}$alkyl, C$_{1-6}$perfluoroalkyl, halogen, hydroxy, C$_{1-6}$alkoxy and nitro, and wherein heteroaryl is thiophenyl, benzothiophenyl, furanyl, benzofuranyl, tetrahydroquinolyl, tetrahydroisoquinolyl, indolyl, imidazolyl, benzimidazolyl, pyridinyl, isothiazolyl, benzisothiazolyl, isoxazolyl, benzisoxazolyl, isoquinolyl, or quinolyl wherein heteroaryl is optionally substituted with one or two substituents each independently selected from the group C$_{1-6}$alkyl, halogen, hydroxy, benzyl and C$_{1-6}$alkoxy,

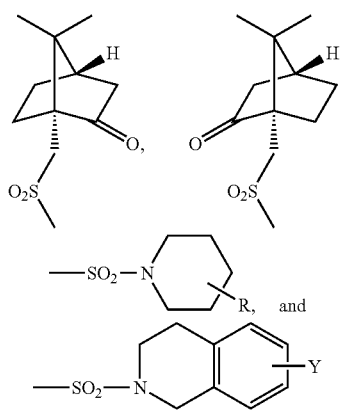

wherein
R is hydrogen or benzyl
Y is selected from the group consisting of hydrogen, C$_{1-6}$alkyl, C$_{1-6}$perfluoroalkyl, halogen, hydroxy, C$_{1-6}$alkoxy and nitro;
R$_2$ and R$_3$ are the same or different and independently selected from the group consisting of hydrogen, C$_{1-6}$alkyl, C$_{1-6}$alkylcarbonyl, formyl, C$_{2-6}$alkenyl, C$_{3-6}$cycloalkylC$_{1-6}$alkyl and R$_2$, R$_3$ taken together can form a ring of from 2-5 carbon atoms;
R$_4$ is selected from the group consisting of hydrogen, C$_{1-4}$alkyl, and C$_{1-6}$alkylcarbonyl;
X is selected from the group consisting of hydrogen and C$_{1-6}$alkyl; and
n is an integer 1, 2 or 3,
a stereoisomer or a pharmaceutically acceptable salt thereof, The present invention also comprises a pharmaceutical composition comprising the compound of formula I and a pharmaceutically acceptable carrier, a method of treating a patient for abnormal dopamine levels, in particular Parkinson's Disease, by administering to the patient a therapeutically effective amount of the compound formula I.

DETAILED DESCRIPTION OF THE INVENTION

The terms as used herein have the following meanings:

As used herein, the expression "C$_{1-6}$ alkyl" used alone or in combination with other terms means an alkyl (or alkylene as appropriate), straight or branched-chain and includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$alkoxy", "$C_{1-6}$alkoxyC$_{1-6}$alkyl", "hydroxyC$_{1-6}$alkyl", "$C_{1-6}$alkylcarbonyl", "$C_{1-6}$alkoxycarbonylC$_{1-6}$alkyl", "$C_{1-6}$alkoxycarbonyl", "aminoC$_{1-6}$alkyl", "$C_{1-6}$alkylcarbamoylC$_{1-6}$alkyl", "$C_{1-6}$dialkylcarbamoylC$_{1-6}$alkyl" "mono- or di-$C_{1-6}$alkylaminoC$_{1-6}$alkyl", aminoC$_{1-6}$alkylcarbonyl", "diphenylC$_{1-6}$alkyl", "phenylC$_{1-6}$alkyl", "phenylcarboylC$_{1-6}$alkyl" and "phenoxyC$_{1-6}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkylC$_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein "halogen" or "halo" means chloro, fluoro, bromo, and iodo.

As used herein the expression "carbamoyl" means an —NC(O)— group where the radical is bonded at two positions connecting two separate additional groups.

As used herein, "patient" means a warm blooded animal, such as for example rat, mice, dogs, cats, guinea pigs, and primates such as humans.

By a "therapeutically-effective amount" of a dopaminergic agent is meant a sufficient amount of the compound to treat dopamine-related disorders at a reasonable benefit/risk ratio applicable to any medical treatment. It will be understood, however, that the total daily usage of the compounds and compositions of the present invention will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient; the time of administration, route of administration, and rate of excretion of the specific compound employed; the duration of the treatment; drugs used in combination or coincidentally with the specific compound employed; and like factors well known in the medical arts. T The term "affective disorder" as used herein refers to disorders that are characterized by changes in mood as the primary clinical manifestation, for example, depression.

The term "antipsychotic agent", as used herein, refers to drugs used extensively in the symptomatic management of all forms of schizophrenia, organic psychosis, the manic phase of manic-depressive illness and other acute idiopathic illnesses, and occasionally used in the treatment of depression or in severe anxiety. The term "attention deficit disorder" as used herein refers to a neuropsychiatric disorder characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" refers to a deficiency in any of the aspects of the cognitive (information processing) functions of perceiving, thinking and remembering.

The term "dopamine-related cardiovascular disorders", as used herein, refers to conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents, which include, for example, use in renal failure.

The term "dopamine-related neurological and psychological disorders", as used herein, refers to behavioral disorders, such as psychoses and addictive behavior disorders; affective disorders, such as major depression; and movement disorders, such as Parkinson's disease, Huntington's disease and Gilles de la Tourette's syndrome, which have been linked, pharmacologically and/or clinically, to either insufficient or excessive functional dopaminergic activity in the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs, intractable hiccough and alcoholic hallucinosis. "Normal dopamine levels" are those levels of dopamine that are found in the brains of control subjects and are usually measured as levels of the dopamine metabolites homovanillic acid (3-methoxy-4-hydroxyphenylacetic acid) and 3,4-dihydroxyphenylacetic acid. Abnormal dopamine levels are those levels that are not within the range of dopamine levels found in the brains of control subjects.

The term "substance abuse", as used herein, refers to periodic or regular self-administration of psychoactive substances in the absence of medical indications and despite the presence of persistent or recurrent social, occupational, psychological or physical problems that the person knows are caused by or may be exacerbated by continued use of the substance.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

"Therapeutically effective amount" means an amount of the compound which is effective in treating the named disorder or condition.

As used in the examples and preparations that follow, the terms used therein shall have the meanings indicated: "kg" refers to kilograms, "g" refers to grams, "mg" refers to milligrams, "□g" refers to micrograms, "pg" refers to picograms, "mol" refers to moles, "mmol" refers to millimoles, "nmole" refers to nanomoles, "L" refers to liters, "mL" or "ml" refers to milliliters, "□L" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "$[□]^{20}{}_D$," refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "□M" refers to micromolar, "nM" refers to nanomolar, "TLC" refers to thin layer chromatography, "HPLC" refers to high performance liquid chromatography, "HRMS" refers to high resolution mass spectrum, "CIMS" refers to chemical ionization mass spectrometry, "$t_R$" refers to retention time, "lb" refers to pounds, "gal" refers to gallons, "L.O.D." refers to loss on drying, "□Ci" refers to microcuries, "i.p." refers to intraperitoneally, "i.v." refers to intravenously.

In one aspect of this invention there is disclosed novel compounds having the general shown in formula I:

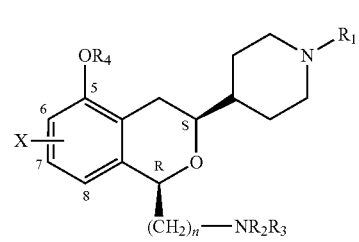

wherein $R_1$ is selected from the group consisting of hydrogen, phenoxycarbonyl, $C_{1-6}$alkoxycarbonyl, benzyloxycarbonyl, naphthyloxycarbonyl, phenylcarbamoyl, phenylcarbamoyl$C_{1-6}$alkyl, biphenylcarbamoyl, phenyl-$C_{1-6}$alkylcarbamoyl, naphthylcarbamoyl$C_{1-6}$alkyl, N-phenyl-N—$C_{1-6}$alkycarbamoyl, $C_{1-6}$alkyl and $C_{1-6}$dialkylcarbamoyl, $C_{2-6}$alkenyl and $C_{2-6}$dialkenylcarbamoyl, diphenylcarbamoyl, heteroarylcarbamoyl$C_{1-6}$alkyl, phenylcarbonyl, biphenylcarbonyl, $C_{1-6}$alkylcarbonyl, morpholinylcarbonyl, piperidinylcarbonyl, pyrrolidinylcarbonyl, phenothiazinylcarbonyl, phenylsulfonyl, diphenylsulfonyl, naphthylsulfonyl, $C_{1-10}$alkylsulfonyl, naphthyl $C_{1-6}$alkylsulfonyl, $C_{1-6}$perfluoroalkylsulfonyl, diphenyl$C_{1-6}$alkylsulfonyl, benzenesulfonyl, $C_{1-6}$dialkylaminosulfonyl, diphenyl$C_{1-6}$alkyl, benzyl, phenyl$C_{2-6}$alkyl, naphthy-$C_{1-6}$alkyl; $C_{3-6}$cycloalkyl$C_{1-6}$alkyl, phenyl$C_{1-6}$alkenyl, heteroaryl$C_{1-6}$alkyl, α-carboxybenzyl, phenylcarbonyl$C_{1-6}$alkyl, hydroxy$C_{1-6}$alkyl, biphenyl$C_{1-6}$alkyl, $C_{1-6}$alkyl, phenoxyphenyl$C_{1-6}$alkyl, phenylurea$C_{1-6}$alkyl, indanyl, wherein benzyl and phenyl are optionally substituted with one or two substituents each independently selected from the group consisting of $C_{1-6}$alkyl, $C_{1-6}$perfluoroalkyl, halogen, hydroxy, $C_{1-6}$alkoxy and nitro, and wherein heteroaryl is thiophenyl, benzothiophenyl, furanyl, benzofuranyl, tetrahydroquinolyl, tetrahydroisoquinolyl, indolyl, imidazolyl, benzimidazolyl, pyridinyl, isothiazolyl, benzisothiazolyl, isoxazolyl, benzisoxazolyl, isoquinolyl, or quinolyl wherein heteroaryl is optionally substituted with one or two substituents each independently selected from the group $C_{1-6}$alkyl, halogen, hydroxy, benzyl and $C_{1-6}$alkoxy,

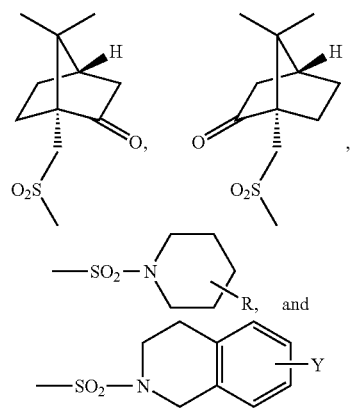

wherein
R is hydrogen or benzyl;
Y is selected from the group consisting of hydrogen, $C_{1-6}$alkyl, $C_{1-6}$perfluoroalkyl, halogen, hydroxy, $C_{1-6}$alkoxy and nitro;
$R_2$ and $R_3$ are the same or different and independently selected from the group consisting of hydrogen, $C_{1-6}$alkyl, $C_{1-6}$alkylcarbonyl, formyl, $C_{2-6}$alkenyl, and $C_{3-6}$cycloalkyl$C_{1-6}$alkyl and $R_2$, $R_3$ taken together can form a ring of from 2-5 carbon atoms;
$R_4$ is selected from the group consisting of hydrogen, $C_{1-4}$alkyl, and $C_{1-6}$alkylcarbonyl;
X is selected from the group consisting of hydrogen and $C_{1-6}$alkyl; and
n is an integer 1, 2 or 3,
a stereoisomer or a pharmaceutically acceptable salt thereof.

In a further aspect of this embodiment, a compound is disclosed wherein $R_4$ is selected from the group consisting of hydrogen and $C_{1-4}$alkyl.

In a further aspect of this embodiment, a compound is disclosed wherein $R_2$ and $R_3$ are the same or different and independently selected from the group consisting of hydrogen, $C_{1-3}$alkyl, $C_{2-4}$alkenyl, $C_{3-6}$cycloalkyl$C_{1-3}$alkyl and $R_2$, $R_3$ taken together can form a ring of from 2-5 carbon atoms, $R_4$ is selected from the group consisting of hydrogen and $C_{1-3}$alkyl, X is $C_{1-4}$alkyl, and n is 1.

In another aspect of this embodiment, is disclosed a compound wherein $R_2$ and $R_3$ are hydrogen, $R_4$ is hydrogen; and X is $C_{1-3}$alkyl.

In yet another aspect of this embodiment, is disclosed a compound wherein X is methyl.

In still another aspect of this embodiment, is disclosed a compound wherein X is substituted at the 6-position of the ring.

In another aspect of this embodiment, there is disclosed a compound of formula I wherein $R_1$ is selected from the group consisting of hydrogen, diphenyl$C_{1-6}$alkyl, benzyl, phenyl$C_{2-6}$alkyl, naphthyl$C_{1-6}$alkyl; $C_{3-6}$cycloalkyl$C_{1-6}$alkyl, phenyl$C_{1-6}$alkenyl, heteroaryl$C_{1-6}$alkyl, α-carboxybenzyl, phenylcarbonyl$C_{1-6}$alkyl, hydroxy$C_{1-6}$alkyl, biphenyl $C_{1-6}$alkyl, $C_{1-6}$alkyl, phenoxyphenyl$C_{1-6}$alkyl, phenylcarbamoyl$C_{1-6}$alkyl, naphthylcarbamoyl$C_{1-6}$alkyl, and phenylurea$C_{1-6}$alkyl; $R_2$ and $R_3$ are the same or different and independently selected from the group consisting of hydrogen, $C_{1-6}$alkyl, $C_{2-6}$alkenyl, $C_{3-6}$cycloalkyl$C_{1-6}$alkyl and $R_2$, $R_3$ taken together can form a ring of from 2-5 carbon atoms; $R_4$ is selected from the group consisting of hydrogen and $C_{1-4}$alkyl; X is $C_{1-6}$alkyl and n is 1.

Specific compounds of this aspect of the embodiment are selected from the group consisting of:
(1R,3S)-6-Methyl-1-methylaminomethyl-3-(1-methyl-piperidin-4-yl)-isochroman-5-ol,
(1R,3S)-1-Aminomethyl-6-methyl-3-(1-phenethyl-piperidin-4-yl)-isochroman-5-ol
(1R,3S)-1-Aminomethyl-3-{1-[2-(3-chloro-phenyl)-ethyl]-piperidin-4-yl}-6-methyl-isochroman-5-ol,
(1R,3S)-1-Aminomethyl-3-{1-[4,4-bis-(4-fluoro-phenyl)-butyl]-piperidin-4-yl}-6-methyl-isochroman-5-ol,
(1R,3S)-1-Aminomethyl-6-methyl-3-[1-(3-phenyl-butyl)-piperidin-4-yl]-isochroman-5-ol,
(1R,3S)-1-Aminomethyl-3-[1-(2,2-diphenyl-ethyl)-piperidin-4-yl]-6-methyl-isochroman-5-ol,
(1R,3S)-1-Aminomethyl-3-(1-benzyl-piperidin-4-yl)-6-methyl-isochroman-5-ol,
[4-((1R,3S)-1-Aminomethyl-5-hydroxy-6-methyl-isochroman-3-yl)-piperidin-1-yl]-phenylacetic acid,
(1R,3S)-1-Aminomethyl-6-methyl-3-[1-(2-phenyl-propyl)-piperidin-4-yl]-isochroman-5-ol,
(1R,3S)-1-Aminomethyl-6-methyl-3-[1-(1-methyl-2-phenyl-ethyl)-piperidin-4-yl]-isochroman-5-ol,
(1R,3S)-1-Aminomethyl-3-[1-(4-fluoro-benzyl)-piperidin-4-yl]-6-methyl-isochroman-5-ol,
(1R,3S)-1-Aminomethyl-3-[1-(2-fluoro-benzyl)-piperidin-4-yl]-6-methyl-isochroman-5-ol
(1R,3S)-1-Aminomethyl-6-methyl-3-[1-(3-phenyl-allyl)-piperidin-4-yl]-isochroman-5-ol,
(1R,3S)-1-Aminomethyl-3-[1-(3-methoxy-benzyl)-piperidin-4-yl]-6-methyl-isochroman-5-ol,
(1R,3S)-1-Aminomethyl-3-(1-indan-2-yl-piperidin-4-yl)-6-methyl-isochroman-5-ol,
(1R,3S)-1-Aminomethyl-3-(1-butyl-piperidin-4-yi)-6-methyl-isochroman-5-ol,
(1R,3S)-1-Aminomethyl-3-(1-cyclohexylmethyl-piperidin-4-yl)-6-methyl-isochroman-5-ol,
(1R,3S)-1-Aminomethyl-3-[1-(2-chloro-benzyl)-piperidin-4-yl]-6-methyl-isochroman-5-ol,
(1R,3S)-1-Aminomethyl-3-[1-(3-chloro-benzyl)-piperidin-4-yl]-6-methyl-isochroman-5-ol,
N-{2-[4-((1R,3S)-1-Aminomethyl-5-hydroxy-6-methyl-isochroman-3-yl)-piperidin-1-yl]-ethyl}-benzamide,
N-{2-[4-((1R,3S)-1-Aminomethyl-5-hydroxy-6-methyl-isochroman-3-yl)-piperidin-1-yl]-ethyl}-4-fluoro-benzamide,
(1R,3S)-1-Aminomethyl-3-{1-[3-(6-fluoro-benzo[d]isoxazol-3-yl)-2-methyl-propyl]-piperidin-4-yl}-6-methyl-isochroman-5-ol,
N-{2-[4-((1R,3S)-1-Aminomethyl-5-hydroxy-6-methyl-isochroman-3-yl)-piperidin-1-yl]-ethyl}-4-methyl-benzamide,
(1R,3S)-1-Aminomethyl-3-{1-[3-(6-fluoro-benzo[d]isoxazol-3-yl)-butyl]-piperidin-4-yl}-6-methyl-isochroman-5-ol,
(1R,3S)-1-Aminomethyl-3-(1-cyclopropylmethyl-piperidin-4-yl)-6-methyl-isochroman-5-ol,
(1R,3S)-6-Methyl-1-methylaminomethyl-3-[1-(2-phenyl-butyl)-piperidin-4-yl]-isochroman-5-ol,
1-{2-[4-((1R,3S)-1-Aminomethyl-5-hydroxy-6-methyl-isochroman-3-yl)-piperidin-1-yl]-ethyl}-3-(4-fluoro-phenyl)-urea,
1-{2-[4-((1R,3S)-1-Aminomethyl-5-hydroxy-6-methyl-isochroman-3-yl)-piperidin-1-yl]-ethyl}-3-phenyl-urea,
(1R,3S)-1-Aminomethyl-6-methyl-3-[1-(3-phenyl-propyl)-piperidin-4-yl]-isochroman-5-ol,
(1R,3S)-3-(1-Benzyl-piperidin-4-yl)-1-dimethylaminomethyl-6-methyl-isochroman-5-ol,
(1R,3S)-3-(1-Benzyl-piperidin-4-yl)-1-diethylaminomethyl-6-methyl-isochroman-5-ol,
(1R,3S)-3-(1-Benzyl-piperidin-4-yl)-6-methyl-1-methylaminomethyl-isochroman-5-ol,
(1R,3S)-3-(1-Benzyl-piperidin-4-yl)-1-ethylaminomethyl-6-methyl-isochroman-5-ol,
(1R,3S)-3-(1-Benzyl-piperidin-4-yl)-1-[(ethyl-methyl-amino)-methyl]-6-methyl-isochroman-5-ol,
(1R,3S)-3-(1-Benzyl-piperidin-4-yl)-6-methyl-1-propylaminomethyl-isochroman-5-ol,
(1R,3S)-3-(1-Benzyl-piperidin-4-yl)-6-methyl-1-[(methyl-propyl-amino)-methyl]-isochroman-5-ol,
(1R,3S)-1-[(Allyl-methyl-amino)-methyl]-3-(1-benzyl-piperidin-4-yl)-6-methyl-isochroman-5-ol,
(1R,3S)-3-(1-Benzyl-piperidin-4-yl)-1-cyclobutylaminomethyl-6-methyl-isochroman-5-ol,
(1R,3S)-3-(1-Benzyl-piperidin-4-yl)-6-methyl-1-pyrrolidin-1-ylmethyl-isochroman-5-ol, 2-[4-((1R,3S)-1-Ethylaminomethyl-5-hydroxy-6-methyl-isochroman-3-yl)-piperidin-1-yl]-1-phenyl-ethanone,
2-[4-((1R,3S)-1-Diallylaminomethyl-5-hydroxy-6-methyl-isochroman-3-yl)-piperidin-1-yl]-1-phenyl-ethanone,
(1R,3S)-1-Aminomethyl-6-methyl-3-[1-(4-trifluoromethyl-benzyl)-piperidin-4-yl]-isochroman-5-ol,
(1R,3S)-6-Methyl-1-methylaminomethyl-3-[1-(4-trifluoromethyl-benzyl)-piperidin-4-yl]-isochroman-5-ol,
(1R,3S)-1-Ethylaminomethyl-6-methyl-3-[1-(4-trifluoromethyl-benzyl)-piperidin-4-yl]-isochroman-5-ol,
(1R,3S)-1-Dimethylaminomethyl-6-methyl-3-[1-(4-trifluoromethyl-benzyl)-piperidin-4-yl]-isochroman-5-ol,
(1R,3S)-1-[(Ethyl-methyl-amino)-methyl]-6-methyl-3-[1-(4-trifluoromethyl-benzyl)-piperidin-4-yl]-isochroman-5-ol,
(1R,3S)-6-Methyl-1-[(methyl-propyl-amino)-methyl]-3-[1-(4-trifluoromethyl-benzyl)-piperidin-4-yl]-isochroman-5-ol,
(1R,3S)-1-Diallylaminomethyl-6-methyl-3-[1-(4-trifluoromethyl-benzyl)-piperidin-4-yl]-isochroman-5-ol,
(1R,3S)-1-Allylaminomethyl-3-(1-benzyl-piperidin-4-yl)-6-methyl-isochroman-5-ol,
(1R,3S)-3-(1-Benzyl-piperidin-4-yl)-1-diallylaminomethyl-6-methyl-isochroman-5-ol,
(1R,3S)-1-Aminomethyl-6-methyl-3-(1-naphthalen-1-ylmethyl-piperidin-4-yl)-isochroman-5-ol,
(1R,3S)-1-Aminomethyl-3-(1-isobutyl-piperidin-4-yl)-6-methyl-isochroman-5-ol,
(1R,3S)-1-Aminomethyl-6-methyl-3-[1-(3-methyl-butyl)-piperidin-4-yl]-isochroman-5-ol,
(1R,3S)-1-Aminomethyl-3-[1-(2,2-dimethyl-propyl)-piperidin-4-yl]-6-methyl-isochroman-5-ol,
(1R,3S)-1-Aminomethyl-3-[1-(2-hydroxy-ethyl)-piperidin-4-yl]-6-methyl-isochroman-5-ol,
(1R,3S)-1-Aminomethyl-3-(1-isopropyl-piperidin-4-yl)-6-methyl-isochroman-5-ol,
(1R,3S)-1-Aminomethyl-6-methyl-3-(1-naphthalen-2-ylmethyl-piperidin-4-yl)-isochroman-5-ol,
(1R,3S)-1-Aminomethyl-6-methyl-3-[1-(4-phenoxy-benzyl)-piperidin-4-yl]-isochroman-5-ol,
(1R,3S)-1-Aminomethyl-6-methyl-3-(1-thiophen-2-ylmethyl-piperidin-4-yl)-isochroman-5-ol,
(1R,3S)-1-Aminomethyl-3-[1-(4-isopropyl-benzyl)-piperidin-4-yl]-6-methyl-isochroman-5-ol,
(1R,3S)-1-Aminomethyl-3-(1-biphenyl-4-ylmethyl-piperidin-4-yl)-6-methyl-isochroman-5-ol,
(1R,3S)-1-Aminomethyl-3-[1-(2,4-difluoro-benzyl)-piperidin-4-yl]-6-methyl-isochroman-5-ol,
(1R,3S)-1-Aminomethyl-6-methyl-3-[1-(1-phenyl-ethyl)-piperidin-4-yl]-isochroman-5-ol,
(1R,3S)-1-Aminomethyl-6-methyl-3-(1-pyridin-2-ylmethyl-piperidin-4-yl)-isochroman-5-ol,
(1R,3S)-1-Aminomethyl-6-methyl-3-(1-pyridin-3-ylmethyl-piperidin-4-yl)-isochroman-5-ol,
(1R,3S)-1-Aminomethyl-6-methyl-3-(1-pyridin-4-ylmethyl-piperidin-4-yl)-isochroman-5-ol,
(1R,3S)-1-Aminomethyl-6-methyl-3-(1-quinolin-2-ylmethyl-piperidin-4-yl)-isochroman-5-ol,
(1R,3S)-1-Aminomethyl-6-methyl-3-(1-quinolin-3-ylmethyl-piperidin-4-yl)-isochroman-5-ol,
(1R,3S)-1-Aminomethyl-6-methyl-3-(1-quinolin-4-ylmethyl-piperidin-4-yl)-isochroman-5-ol,
(1R,3S)-1-Aminomethyl-3-[1-(4-chloro-benzyl)-piperidin-4-yl]-6-methyl-isochroman-5-ol,
(1R,3S)-1-Aminomethyl-3-[1-(2,4-dichloro-benzyl)-piperidin-4-yl]-6-methyl-isochroman-5-ol,
(1R,3S)-1-Aminomethyl-3-[1-(3,4-dichloro-benzyl)-piperidin-4-yl]-6-methyl-isochroman-5-ol,
(1R,3S)-1-Aminomethyl-3-[1-(4-methoxy-benzyl)-piperidin-4-yl]-6-methyl-isochroman-5-ol,
(1R,3S)-1-Aminomethyl-3-[1-(4-hydroxy-benzyl)-piperidin-4-yl]-6-methyl-isochroman-5-ol,
(1R,3S)-1-Aminomethyl-3-[1-(3,4-difluoro-benzyl)-piperidin-4-yl]-6-methyl-isochroman-5-ol,
(1R,3S)-1-Aminomethyl-6-methyl-3-[1-(2-methyl-benzyl)-piperidin-4-yl]-isochroman-5-ol,
(1R,3S)-1-Aminomethyl-6-methyl-3-[1-(3-methyl-benzyl)-piperidin-4-yl]-isochroman-5-ol,
(1R,3S)-1-Aminomethyl-6-methyl-3-[1-(4-methyl-benzyl)-piperidin-4-yl]-isochroman-5-ol,
(1R,3S)-1-Aminomethyl-6-methyl-3-(1-thiophen-3-ylmethyl-piperidin-4-yl)-isochroman-5-ol,
(1R,3S)-1-Aminomethyl-3-[1-(2-methoxy-benzyl)-piperidin-4-yl]-6-methyl-isochroman-5-ol,
(1R,3S)-1-Aminomethyl-3-[1-(3-fluoro-benzyl)-piperidin-4-yl]-6-methyl-isochroman-5-ol,
(1R,3S)-1-Aminomethyl-3-[1-(2-fluoro-4-trifluoromethyl-benzyl)-piperidin-4-yl]-6-methyl-isochroman-5-ol,
(1R,3S)-1-Aminomethyl-3-(1-furan-3-ylmethyl-piperidin-4-yl)-6-methyl-isochroman-5-ol,
(1R,3S)-1-Aminomethyl-6-methyl-3-[1-(2-trifluoromethyl-benzyl)-piperidin-4-yl]-isochroman-5-ol,
(1R,3S)-1-Aminomethyl-6-methyl-3-[1-(3-trifluoromethyl-benzyl)-piperidin-4-yl]-isochroman-5-ol,
(1R,3S)-1-Aminomethyl-3-[1-(3,5-bis-trifluoromethyl-benzyl)-piperidin-4-yl]-6-methyl-isochroman-5-ol,
(1R,3S)-1-Aminomethyl-3-[1-(2,5-bis-trifluoromethyl-benzyl)-piperidin-4-yl]-6-methyl-isochroman-5-ol,
(1R,3S)-1-Aminomethyl-3-[1-(2-chloro-5-trifluoromethyl-benzyl)-piperidin-4-yl]-6-methyl-isochroman-5-ol,
(1R,3S)-1-Aminomethyl-3-[1-(4-chloro-3-trifluoromethyl-benzyl)-piperidin-4-yl]-6-methyl-isochroman-5-ol,
(1R,3S)-1-Aminomethyl-3-[1-(2-chloro-3-trifluoromethyl-benzyl)-piperidin-4-yl]-6-methyl-isochroman-5-ol,
(1R,3S)-1-Aminomethyl-3-[1-(2-fluoro-3-trifluoromethyl-benzyl)-piperidin-4-yl]-6-methyl-isochroman-5-ol,
(1R,3S)-1-Aminomethyl-3-[1-(2-fluoro-5-trifluoromethyl-benzyl)-piperidin-4-yl]-6-methyl-isochroman-5-ol,
(1R,3S)-1-Aminomethyl-3-[1-(3-fluoro-4-trifluoromethyl-benzyl)-piperidin-4-yl]-6-methyl-isochroman-5-ol,
(1R,3S)-1-Aminomethyl-3-[1-(4-fluoro-3-trifluoromethyl-benzyl)-piperidin-4-yl]-6-methyl-isochroman-5-ol,
(1R,3S)-1-Aminomethyl-3-[1-(3-fluoro-5-trifluoromethyl-benzyl)-piperidin-4-yl]-6-methyl-isochroman-5-ol,
(1R,3S)-1-Aminomethyl-3-(1-benzofuran-2-ylmethyl-piperidin-4-yl)-6-methyl-isochroman-5-ol,
(1R,3S)-1-Aminomethyl-6-methyl-3-[1-(3-methyl-benzo[b]thiophen-2-ylmethyl)-piperidin-4-yl]-isochroman-5-ol,
(1R,3S)-1-Aminomethyl-3-(1-benzo[b]thiophen-3-ylmethyl-piperidin-4-yl)-6-methyl-isochroman-5-ol,
(1R,3S)-1-Aminomethyl-6-methyl-3-[1-(1-methyl-1H-indol-2-ylmethyl)-piperidin-4-yl]-isochroman-5-ol,
(1R,3S)-1-Aminomethyl-3-[1-(1H-indol-3-ylmethyl)-piperidin-4-yl]-6-methyl-isochroman-5-ol,
(1R,3S)-1-Aminomethyl-6-methyl-3-[1-(1-methyl-1H-indol-3-ylmethyl)-piperidin-4-yl]-isochroman-5-ol,
(1R,3S)-1-Aminomethyl-3-[1-(1-benzyl-1H-indol-3-ylmethyl)-piperidin-4-yl]-6-methyl-isochroman-5-ol,
(1R,3S)-1-Aminomethyl-6-methyl-3-[1-(1-methyl-1H-benzoimidazol-2-ylmethyl)-piperidin-4-yl]-isochroman-5-ol,
(1R,3S)-3-(1-Benzyl-piperidin-4-yl)-1-dipropylaminomethyl-6-methyl-isochroman-5-ol, (1R,3S)-6-Methyl-1-methylaminomethyl-3-(1-phenethyl-piperidin-4-yl)-isochroman-5-ol,
(1R,3S)-3-[1-(4-Fluoro-benzyl)-piperidin-4-yl]-6-methyl-1-methylaminomethyl-isochroman-5-ol,
(1R,3S)-3-(1-Cyclohexylmethyl-piperidin-4-yl)-6-methyl-1-methylaminomethyl-isochroman-5-ol,
(1R,3S)-3-[1-(4-Isopropyl-benzyl)-piperidin-4-yl]-6-methyl-1-methylaminomethyl-isochroman-5-ol,
(1R,3S)-3-(1-Biphenyl-4-ylmethyl-piperidin-4-yl)-6-methyl-1-methylaminomethyl-isochroman-5-ol,
(1R,3S)-3-[1-(3,4-Difluoro-benzyl)-piperidin-4-yl]-6-methyl-1-methylaminomethyl-isochroman-5-ol,
(1R,3S)-3-[1-(4-Methoxy-benzyl)-piperidin-4-yl]-6-methyl-1-methylaminomethyl-isochroman-5-ol,
(1R,3S)-6-Methyl-1-methylaminomethyl-3-[1-(4-methyl-benzyl)-piperidin-4-yl]-isochroman-5-ol,
N-{3-[4-((1R,3S)-1-Aminomethyl-5-hydroxy-6-methyl-isochroman-3-yl)-piperidin-1-yl]-1-methyl-propyl}-4-chloro-benzamide,
N-{3-[4-((1R,3S)-1-Aminomethyl-5-hydroxy-6-methyl-isochroman-3-yl)-piperidin-1-yl]-1-ethyl-2-methyl-propyl}-4-methyl-benzamide,
N-{3-[4-((1R,3S)-1-Aminomethyl-5-hydroxy-6-methyl-isochroman-3-yl)-piperidin-1-yl]-1-methyl-propyl}-4-methyl-benzamide,
N-{3-[4-((1R,3S)-1-Aminomethyl-5-hydroxy-6-methyl-isochroman-3-yl)-piperidin-1-y]-1-methyl-propyl}-4-trifluoromethyl-benzamide,
N-{3-[4-((1R,3S)-1-Aminomethyl-5-hydroxy-6-methyl-isochroman-3-yl)-piperidin-1-yl]-1-methyl-propyl}-2,4-dichloro-benzamide,
Biphenyl-4-carboxylic acid {3-[4-((1R,3S)-1-aminomethyl-5-hydroxy-6-methyl-isochroman-3-yl)-piperidin-1-yl]-1-methyl-propyl}-amide,
Benzo[b]thiophene-2-carboxylic acid {3-[4-((1R,3S)-1-aminomethyl-5-hydroxy-6-methyl-isochroman-3-yl)-piperidin-1-yl]-1-methyl-propyl}-amide,
N-{3-[4-((1R,3S)-1-Aminomethyl-5-hydroxy-6-methyl-isochroman-3-yl)-piperidin-1-yl]-1-methyl-propyl}-benzamide,
N-{3-[4-((1R,3S)-1-Aminomethyl-5-hydroxy-6-methyl-isochroman-3-yl)-piperidin-1-yl]-1-methyl-propyl}-4-fluoro-benzamide,
N-{3-[4-((1R,3S)-1-Aminomethyl-5-hydroxy-6-methyl-isochroman-3-yl)-piperidin-1-yl]-1-methyl-propyl}-4-bromo-benzamide,
N-{3-[4-((1R,3S)-1-Aminomethyl-5-hydroxy-6-methyl-isochroman-3-yl)-piperidin-1-yl]-1-methyl-propyl}-4-nitro-benzamide,
N-((1R,3S)-5-Isopropoxy-6-methyl-3-(4-piperidinyl)-1-isochromanyl-methyl)formamide,
N-((1R,3S)-5-methoxy-6-methyl-3-(4-piperidinyl)-1-isochromanyl-methyl)formamide,
Naphthalene-2-carboxylic acid {3-[4-((1R,3S)-1-aminomethyl-5-hydroxy-6-methyl-isochroman-3-yl)-piperidin-1-yl]-1-methyl-propyl}-amide dihydrochloride, and
Thiophene-2-carboxylic acid {3-[4-((1R,3S)-1-aminomethyl-5-hydroxy-6-methyl-isochroman-3-yl)-piperidin-1-yl]-1-methyl-propyl}-amide.

In yet another aspect of this embodiment, there is provided compounds of formula I wherein $R_1$ is selected from the group consisting of phenoxycarbonyl, $C_{1-6}$alkoxycarbonyl, benzyloxycarbonyl, naphthyloxycarbonyl, phenylcarbonyl, biphenylcarbonyl, $C_{1-6}$alkylcarbonyl phenylcarbamoyl, biphenylcarbamoyl, phenyl$C_{1-6}$alkylcarbamoyl, N-phenyl-N—$C_{1-6}$alkycarbamoyl, $C_{1-6}$alkyl and $C_{1-6}$dialkylcarbamoyl, $C_{2-6}$alkenyl and $C_{2-6}$dialkenylcarbamoyl, diphenylcarbamoyl, heteroarylcarbamoyl$C_{1-6}$alkyl, phenylcarbonyl, biphenylcarbonyl, $C_{1-6}$alkylcarbonyl, morpholinylcarbonyl, piperidinylcarbonyl, pyrrolidinylcarbonyl and phenothiazinylcarbonyl; $R_2$ and $R_3$ are the same or different and independently selected from the group consisting of hydrogen, $C_{1-6}$alkyl, $C_{2-6}$alkenyl, $C_{3-6}$cycloalkyl$C_{1-6}$alkyl and $R_2$, $R_3$ taken together can form a ring of from 2-5 carbon atoms; $R_4$ is selected from the group consisting of hydrogen and $C_{1-4}$alkyl, X is $C_{1-6}$alkyl; and n is 1.

Examples of this aspect of the embodiment include:
4-((1R,3S)-1-Aminomethyl-5-hydroxy-6-methyl-isochroman-3-yl)-piperidine-1-carboxylic acid isopropyl ester,
4-((1R,3S)-1-Aminomethyl-5-hydroxy-6-methyl-isochroman-3-yl)-piperidine-1-carboxylic acid methyl ester,
4-((1R,3S)-1-Aminomethyl-5-hydroxy-6-methyl-isochroman-3-yl)-piperidine-1-carboxylic acid phenyl ester,
4-((1R,3S)-1-Aminomethyl-5-hydroxy-6-methyl-isochroman-3-yl)-piperidine-1-carboxylic acid p-tolyl ester,
4-((1R,3S)-1-Aminomethyl-5-hydroxy-6-methyl-isochroman-3-yl)-piperidine-1-carboxylic acid 4-chloro-phenyl ester,
4-((1R,3S)-1-Aminomethyl-5-hydroxy-6-methyl-isochroman-3-yl)-piperidine-1-carboxylic acid 2-chloro-phenyl ester,
4-((1R,3S)-1-Aminomethyl-5-hydroxy-6-methyl-isochroman-3-yl)-piperidine-1-carboxylic acid 4-bromo-phenyl ester,
4-((1R,3S)-1-Aminomethyl-5-hydroxy-6-methyl-isochroman-3-yl)-piperidine-1-carboxylic acid 4-fluoro-phenyl ester,
4-((1R,3S)-1-Aminomethyl-5-hydroxy-6-methyl-isochroman-3-yl)-piperidine-1-carboxylic acid 2-trifluoromethyl-phenyl ester,
4-((1R,3S)-1-Aminomethyl-5-hydroxy-6-methyl-isochroman-3-yl)-piperidine-1-carboxylic acid 4-methoxy-phenyl ester,
4-((1R,3S)-1-Aminomethyl-5-hydroxy-6-methyl-isochroman-3-yl)-piperidine-1-carboxylic acid 2-hydroxy-phenyl ester,
4-((1R,3S)-1-Aminomethyl-5-hydroxy-6-methyl-isochroman-3-yl)-piperidine-1-carboxylic acid benzyl ester,
4-((1R,3S)-1-Aminomethyl-5-hydroxy-6-methyl-isochroman-3-yl)-piperidine-1-carboxylic acid naphthalen-2-yl ester,
[4-((1R,3S)-1-Aminomethyl-5-hydroxy-6-methyl-isochroman-3-yl)-piperidin-1-yl]-(4-fluoro-phenyl)-methanone,
[4-((1R,3S)-1-Aminomethyl-5-hydroxy-6-methyl-isochroman-3-yl)-piperidin-1-yl]-(4-methoxy-phenyl)-methanone,
[4-((1R,3S)-1-Aminomethyl-5-hydroxy-6-methyl-isochroman-3-yl)-piperidin-1-yl]-(2-hydroxy-phenyl)-methanone,
[4-((1R,3S)-1-Aminomethyl-5-hydroxy-6-methyl-isochroman-3-yl)-piperidin-1-yl]-(4-chloro-phenyl)-methanone,
[4-((1R,3S)-1-Aminomethyl-5-hydroxy-6-methyl-isochroman-3-yl)-piperidin-1-yl]-biphenyl-4-yl-methanone,
[4-((1R,3S)-1-Aminomethyl-5-hydroxy-6-methyl-isochroman-3-yl)-piperidin-1-yl]-phenyl-methanone,
[4-((1R,3S)-1-Aminomethyl-5-hydroxy-6-methyl-isochroman-3-yl)-piperidin-1-yl]-(4-bromo-phenyl)-methanone,
1-[4-((1R,3S)-1-Aminomethyl-5-hydroxy-6-methyl-isochroman-3-yl)-piperidin-1-yl]-2-phenyl-ethanone,
1-[4-((1R,3S)-1-Aminomethyl-5-hydroxy-6-methyl-isochroman-3-yl)-piperidin-1-yl]-ethanone,
1-[4-((1R,3S)-1-Aminomethyl-5-hydroxy-6-methyl-isochroman-3-yl)-piperidin-1-yl]-3-methyl-butan-1-one, 1-[4-((1R,3S)-1-Aminomethyl-5-hydroxy-6-methyl-isochroman-3-yl)-piperidin-1-yl]-3-phenyl-propan-1-one,
1-[4-((1R,3S)-1-Aminomethyl-5-hydroxy-6-methyl-isochroman-3-yl)-piperidin-1-yl]-butan-1-one,
4-((1R,3S)-1-Aminomethyl-5-hydroxy-6-methyl-isochroman-3-yl)-piperidine-1-carboxylic acid (2-fluoro-5-trifluoromethyl-phenyl)-amide,
4-((1R,3S)-1-Aminomethyl-5-hydroxy-6-methyl-isochroman-3-yl)-piperidine-1-carboxylic acid (3-methoxy-phenyl)-amide,
4-((1R,3S)-1-Aminomethyl-5-hydroxy-6-methyl-isochroman-3-yl)-piperidine-1-carboxylic acid (3-hydroxy-phenyl)-amide,
4-((1R,3S)-1-Aminomethyl-5-hydroxy-6-methyl-isochroman-3-yl)-piperidine-1-carboxylic acid (2-hydroxy-phenyl)-amide,
4-((1R,3S)-1-Aminomethyl-5-hydroxy-6-methyl-isochroman-3-yl)-piperidine-1-carboxylic acid (4-fluoro-phenyl)-amide,
4-((1R,3S)-1-Aminomethyl-5-hydroxy-6-methyl-isochroman-3-yl)-piperidine-1-carboxylic acid (2-fluoro-phenyl)-amide,
4-((1R,3S)-1-Aminomethyl-5-hydroxy-6-methyl-isochroman-3-yl)-piperidine-1-carboxylic acid diphenylamide,
4-((1R,3S)-1-Aminomethyl-5-hydroxy-6-methyl-isochroman-3-yl)-piperidine-1-carboxylic acid methyl-phenyl-amide,
4-((1R,3S)-1-Aminomethyl-5-hydroxy-6-methyl-isochroman-3-yl)-piperidine-1-carboxylic acid dimethylamide,
4-((1R,3S)-1-Aminomethyl-5-hydroxy-6-methyl-isochroman-3-yl)-piperidine-1-carboxylic acid diisopropylamide,
[4-((1R,3S)-1-Aminomethyl-5-hydroxy-6-methyl-isochroman-3-yl)-piperidin-1-yl]-morpholin-4-yl-methanone,
[4-((1R,3S)-1-Aminomethyl-5-hydroxy-6-methyl-isochroman-3-yl)-piperidin-1-yl]-pyrrolidin-1-yl-methanone,
4-((1R,3S)-1-Aminomethyl-5-hydroxy-6-methyl-isochroman-3-yl)-piperidine-1-carboxylic acid diethylamide,
[4-((1R,3S)-1-Aminomethyl-5-hydroxy-6-methyl-isochroman-3-yl)-piperidin-1-yl]-phenothiazin-10-yl-methanone,
[4-((1R,3S)-1-Aminomethyl-5-hydroxy-6-methyl-isochroman-3-yl)-piperidin-1-yl]-piperidin-1-yl-methanone,
4-((1R,3S)-1-Aminomethyl-5-hydroxy-6-methyl-isochroman-3-yl)-piperidine-1-carboxylic acid dibutylamide, and
4-((1R,3S)-1-Aminomethyl-5-hydroxy-6-methyl-isochroman-3-yl)-piperidine-1-carboxylic acid diallylamide.

In another aspect of this embodiment, there is provided compounds of formula I wherein $R_1$ is selected from the group consisting phenylsulfonyl, diphenylsulfonyl, naphthylsulfonyl, $C_{1-10}$alkylsulfonyl, naphthyl $C_{1-6}$alkylsulfonyl, $C_{1-6}$perfluoroalkylsulfonyl, diphenyl$C_{1-6}$alkylsulfonyl, benzenesulfonyl, $C_{1-6}$dialkylaminosulfonyl,

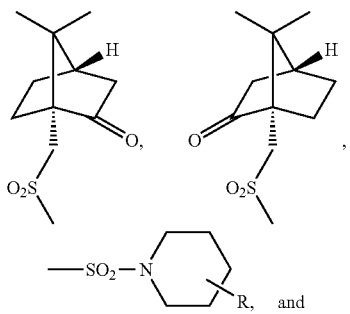

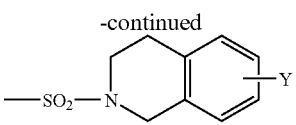

wherein R is hydrogen or benzyl, Y is selected from the group consisting of hydrogen, $C_{1-6}$alkyl, $C_{1-6}$perfluoroalkyl, halogen, hydroxy, $C_{1-6}$alkoxy and nitro, $R_2$ and $R_3$ are the same or different and independently selected from the group consisting of hydrogen, $C_{1-6}$alkyl, $C_{2-6}$alkenyl, $C_{3-6}$cycloalkyl and $C_{1-6}$alkyl, $R_2$, $R_3$ taken together can form ring of from 2-5 carbon atoms, $R_4$ is selected from the group consisting of hydrogen and $C_{1-4}$alkyl, X is $C_{1-6}$alkyl; and n is 1.

Representative examples within the scope of this aspect of the embodiment include:
(1R,3S)-1-Aminomethyl-3-(1-benzenesulfonyl-piperidin-4-yl)-6-methyl-isochroman-5-ol,
(1R,3S)-1-Aminomethyl-6-methyl-3-(1-phenylmethanesulfonyl-piperidin-4-yl)-isochroman-5-ol,
(1R,3S)-1-Aminomethyl-6-methyl-3-[1-(2-trifluoromethyl-benzenesulfonyl)-piperidin-4-yl]-isochroman-5-ol,
(1R,3S)-1-Aminomethyl-3-[1-(3,4-dimethoxy-benzenesulfonyl)-piperidin-4-yl]-6-methyl-isochroman-5-ol,
(1R,3S)-1-Aminomethyl-3-[1-(4-isopropyl-benzenesulfonyl)-piperidin-4-yl]-6-methyl-isochroman-5-ol,
(1R,3S)-1-Aminomethyl-3-[1-(4-tert-butyl-benzenesulfonyl)-piperidin-4-yl]-6-methyl-isochroman-5-ol,
(1R,3S)-1-Aminomethyl-6-methyl-3-[1-(naphthalene-2-sulfonyl)-piperidin-4-yl]-isochroman-5-ol,
(1R,3S)-1-Aminomethyl-3-[1-(4-chloro-benzenesulfonyl)-piperidin-4-yl]-6-methyl-isochroman-5-ol,
(1R,3S)-1-Aminomethyl-3-[1-(2,4-dichloro-benzenesulfonyl)-piperidin-4-yl]-6-methyl-isochroman-5-ol,
(1R,3S)-1-Aminomethyl-3-[1-(3,4-dichloro-benzenesulfonyl)-piperidin-4-yl]-6-methyl-isochroman-5-ol,
(1R,3S)-1-Aminomethyl-3-[1-(2,5-dichloro-benzenesulfonyl)-piperidin-4-yl]-6-methyl-isochroman-5-ol,
(1R,3S)-1-Aminomethyl-3-[1-(biphenyl-4-sulfonyl)-piperidin-4-yl]-6-methyl-isochroman-5-ol,
(1R,3S)-1-Aminomethyl-3-(1-ethanesulfonyl-piperidin-4-yl)-6-methyl-isochroman-5-ol,
(1R,3S)-1-Aminomethyl-3-[1-(butane-1-sulfonyl)-piperidin-4-yl]-6-methyl-isochroman-5-ol,
(1R,3S)-1-Aminomethyl-6-methyl-3-[1-(propane-2-sulfonyl)-piperidin-4-yl]-isochroman-5-ol,
(1R,3S)-1-Aminomethyl-6-methyl-3-[1-(octane-1-sulfonyl)-piperidin-4-yl]-isochroman-5-ol,
(1R,3S)-1-Aminomethyl-6-methyl-3-[1-(2,2,2-trifluoro-ethanesulfonyl)-piperidin-4-yl]-isochroman-5-ol,
(1R,3S)-1-Aminomethyl-6-methyl-3-[1-(2-nitro-phenylmethanesulfonyl)-piperidin-4-yl]-isochroman-5-ol,
(1R,3S)-1-Aminomethyl-6-methyl-3-[1-(2-naphthalen-1-yl-ethanesulfonyl)-piperidin-4-yl]-isochroman-5-ol,
(1R,3S)-1-Aminomethyl-3-[1-(3,4-dichloro-phenylmethanesulfonyl)-piperidin-4-yl]-6-methyl-isochroman-5-ol,
(1R,3S)-1-Aminomethyl-3-[1-(2,2-diphenyl-ethanesulfonyl)-piperidin-4-yl]-6-methyl-isochroman-5-ol,
1(R)-[4-((1R,3S)-1-Aminomethyl-5-hydroxy-6-methyl-isochroman-3-yl)-piperidine-1-sulfonylmethyl]-7,7-dimethyl-bicyclo[2.2.1]heptan-2-one,
1(S)-[4-((1R,3S)-1-Aminomethyl-5-hydroxy-6-methyl-isochroman-3-yl)-piperidine-1-sulfonylmethyl]-7,7-dimethyl-bicyclo[2.2.1]heptan-2-one, 4-((1R,3S)-1-Aminomethyl-5-hydroxy-6-methyl-isochroman-3-yl)-piperidine-1-sulfonic acid dimethylamide,
(1R,3S)-1-Aminomethyl-6-methyl-3-[1-(piperidine-1-sulfonyl)-piperidin-4-yl]-isochroman-5-ol,
(1R,3S)-1-Aminomethyl-3-[1-(4-benzyl-piperidine-1-sulfonyl)-piperidin-4-yl]-6-methyl-isochroman-5-ol, and
(1R,3S)-1-Aminomethyl-3-[1-(3,4-dihydro-1H-isoquinoline-2-sulfonyl)-piperidin-4-yl]-6-methyl-isochroman-5-ol.

In another embodiment, the present invention is directed to a pharmaceutical composition for selectively binding to and activating dopaminergic receptors comprising a pharmaceutically acceptable carrier and a therapeutically effective amount of a compound of formula I.

ders or substance abuse and addictive behavior, or a combination thereof, comprising administering to a patient in need of such treatment a therapeutically effective amount of a compound formula I.

In a further aspect of this embodiment of the invention, the neurological disorder is Parkinson's disease.

Finally in another embodiment of this invention, there is disclosed a method of treatment for the extrapyramidal side effects associated with the use of neuroleptic agents, comprising administering to a patient in need of such treatment a therapeutically effective amount of a compound of formula I.

The compounds of the invention may be prepared by the synthetic routes described below in the Schemes or by other methods, which may be apparent to those skilled in the art.

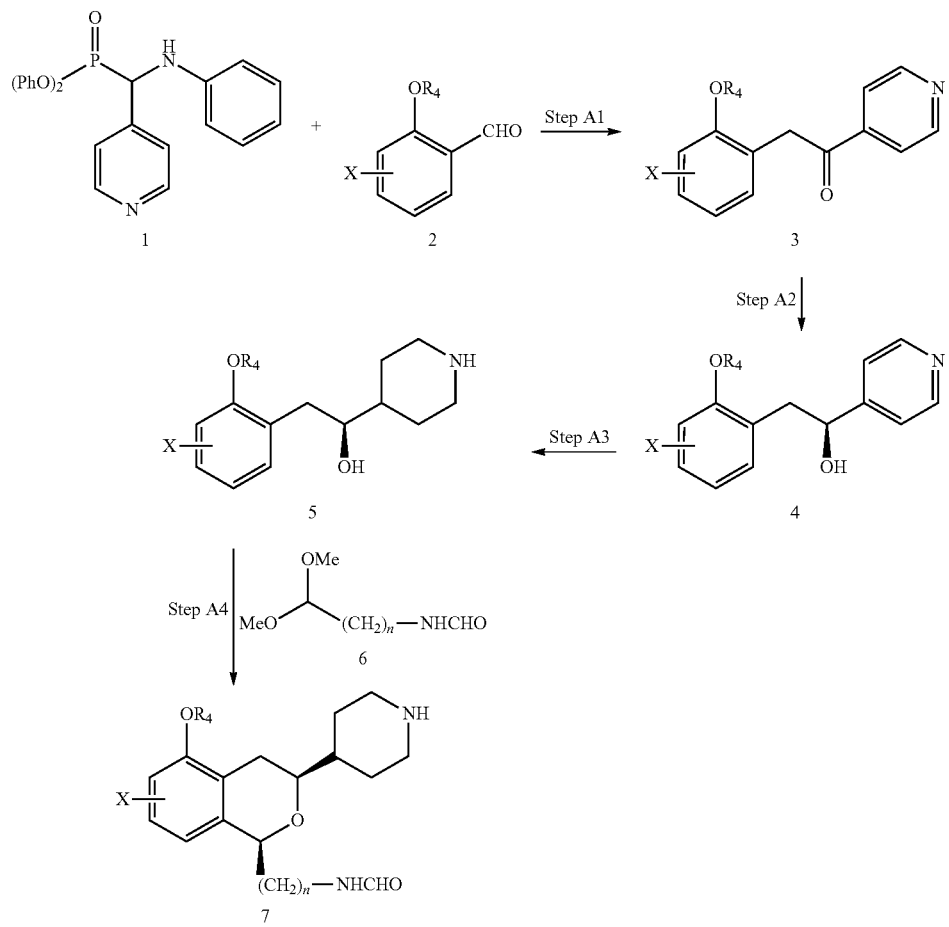

Scheme A

In yet another embodiment, the present invention is also directed to pharmaceutical composition for treating dopamine-related neurological disorders selected form the group consisting of neurological, psychological, cardiovascular, cognitive or attention disorders, substance abuse and addictive behavior, or a combination thereof, comprising a pharmaceutically acceptable carrier and a therapeutically effective amount of a compound formula I.

In another embodiment, the present invention is directed to a method of for treating dopamine-related neurological disorders selected form the group consisting of neurological, psychological, cardiovascular, cognitive or attention disor- In Scheme A the synthesis of the key intermediate of formula 7 is depicted. In step A1 the N,P-acetal of formula 1 formation of which is described by M. Journet, et al., *Tetrahedron Letters*, (1998), 39, 1717-1720, is reacted in a Horner-Emmons type reaction with a base in the presence of an appropriately substituted aromatic aldehyde of the formula 2 in a suitable solvent followed by acidic workup to produce the pyridinyl ketone of formula 3. The reaction is typically run in alcoholic solvents or mixtures of alcohols and ethereal solvents. Alcohols such as ethanol, isopropanol or methanol may be used optionally with ethereal solvents such as tetrahydrofuran or diethyl ether. Suitable bases, for example, would be alkali metal carbonates such as $Na_2CO_3$, $K_2CO_3$ and $Cs_2CO_3$.

In Scheme A step A2 the stereoselective reduction of compound of the formula 3 to give the chiral alcohol of the compound of the formula 4 is accomplished by reaction of the ketone 3 with an suitable chiral reducing reagent. Reduction of the ketone 3 stereoselectively to the desired (S) pyridyl alcohol 4 may be effected by methods well known to those skilled in the art, for instance, optically active reducing agents such a diisopinocampheylchloroborane, (DIP-Chloride™), β-isopinocampheyl-9-borabicyclo[3.3.1]nonane, (Alpine-Borane™) and aluminum complexes derived from 1,1'-binaphthyl-2,2'-diol (BINAL-H), constitute one class. Another approach utilizes an optically active catalyst such as 2,2'-bis(diphenylphosphino)-1,1'-binaphthyl-ruthenium acetate with hydrogen or oxazaborolidines in the presence of borane-tetrahydrofuran (THF) complex or catecholborane. A discussion of enatioselective reduction of ketones can be found in Smith, M. B. and March, J., *March's Advanced Organic Chemistry*, John Wiley and Sons, Inc., 2001, pp. 1200-1201. The reduction can be accomplished in a variety of organic solvents with or without the addition of a Lewis acid such as $BF_3.Et_2O$, which may complex with the pyridine nitrogen and thus require less reducing agent. Suitable organic solvents are ethereal solvents such as ether or THF, hydrocarbon solvents such as pentane, hexane and the like or chlorinated hydrocarbons such as dichloromethane, chloroform or 1,2-dichloroethane. The reaction can be carried out at ambient or below ambient temperatures, for example, −60° C. to 25° C.

In step A4 the chiral pyridinyl alcohol of formula 4 is reduced to the piperidinyl alcohol of compound of the formula 5 by catalytic hydrogenation, a method that is well-known in the art. Suitable catalysts are platinum oxide, palladium, ruthenium, rhodium and nickel. The reaction is normally performed in an alcoholic solvent such as methanol, ethanol, propanol and isopropanol with the optional addition of a mineral acid such as HCl, or in an organic acid such as acetic or propionic acid or mixtures thereof. The reaction can be run at a temperature of between room temperature and 175° C. and at pressures of between 30-2000 p.s.i. of hydrogen.

In step A5 reaction of the alcohol 19 with the formamide acetal 6 results in the formation of the isochroman intermediate 7. The reaction is run in the presence of a Lewis acid as catalyst in a suitable organic solvent at from about −10° C. to. Examples of suitable Lewis acids are boron trifluoride etherate and trimethylsilyl triflate. Suitable organic solvents include ethereal solvents such as ether and tetrahydrofuran or chlorinated hydrocarbons such as dichloromethane, chloroform and 1,2-dichloroethane. The reaction can be carried out at ambient or below ambient temperatures, for example, −10° C. to 25° C. See U.S. Pat. No. 6,004,982, issued Dec. 21, 1999, incorporated herein by reference.

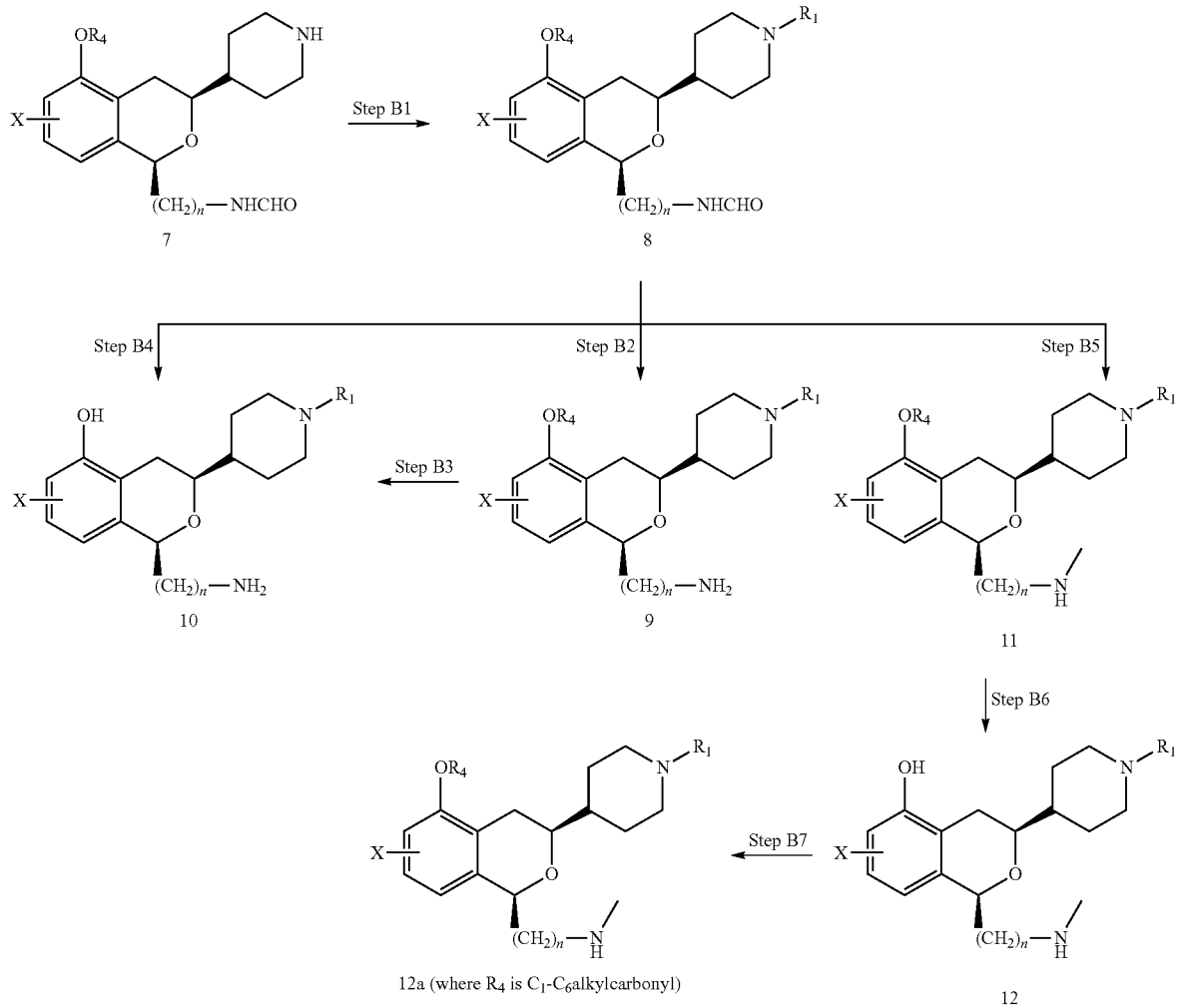

Scheme B

Compounds of formula I wherein $R_1$ is diphenyl$C_{1-6}$alkyl, benzyl, phenyl$C_{2-6}$alkyl, $C_{3-6}$cycloalkyl$C_{1-6}$alkyl, phenyl$C_{1-6}$alkylene heteroaryl$C_{1-6}$alkyl, phenylcarbonyl$C_{1-6}$alkyl, phenylcarbamoyl$C_{1-6}$alkyl, biphenyl$C_{1-6}$alkyl, $C_{1-6}$alkyl and indanyl may be prepared according to the sequence illustrated in Scheme B. Accordingly, in step B1 compound of formula 7 is reacted with an aldehyde in the presence of a suitable borohydride and a suitable solvent to effect a reductive amination resulting in the compound of formula 8. Suitable borohydrides are for example sodium borohydride, sodium triacetoxy borohydride, sodium cyanoborohydride and sodium borohydride in conjunction with titanium isopropoxide may be used. Suitable solvents for the reaction are halogen containing solvents such dichloromethane, chloroform and dichloroethane, alcoholic solvents such as methanol, ethanol and isopropanol, ethereal solvents such as diethyl ether and tetrahydrofuran and acetonitrile. The reaction temperature is not critical but typically the reaction is run at from 0° C. to ambient temperature.

As further illustrated in Scheme B compound 8 can undergo further reactions to give other desired derivatives. In step B2 the formyl group of compound 8 may be cleaved to produce the primary amine, the compound of formula 9. The cleavage can be effected by acid or base hydrolysis, methods well known to those skilled in the art. For instance, the formyl group may be removed by refluxing with dilute hydrochloric acid a water miscible organic solvent, or hydrolysis effected by heating in the presence of an aqueous alkaline metal hydroxide solution with a water miscible cosolvent.

In step B3 cleavage of the phenol ether compound 9 (where $R_4$ is $C_1$-$C_4$alkyl) to the compound of formula 10, can be readily accomplished by reaction of compound 9 with a suitable Lewis acid in a suitable organic solvent. Suitable Lewis acids are boron trihalides and aluminum trihalides, for instance boron tribromide, boron trichloride, aluminum tribromide and aluminum trichloride. Suitable organic solvents are alkylhalides such as dichloromethane, chloroform and dichloroethane, and aromatic solvents such as benzene, toluene and xylenes. Typically, the reaction can be run from $-10°$ C. to the reflux temperature of the organic solvent Alternatively, in step B4 compound 10 can also be obtained from the compound 8 directly by concomitant cleavage of the arylalkyl ether, and the formyl group by the reaction of compound 10 with a suitable mineral acid optionally with a quantity of a suitable organic acid. Suitable mineral acids are concentrated hydrochloric acid, hydrobromic acid and hydroiodic acid and suitable organic acids are acetic, trifluoroacetic and propionic acid. The reaction temperature may vary from about ambient to reflux temperature of the reaction medium.

In step B5 preparation of the methylamino compound of formula 11 may be conveniently accomplished by reduction of the formamide group of the compound of the formula 8. Reduction can be readily accomplished by treatment of the formamide with an appropriate metal hydride or borohydride in a suitable organic solvent. Appropriate metal hydrides are lithium aluminum hydride, aluminum hydride or bis(2-methoxyethoxy)aluminum hydride. Appropriate borohydrides are, for example, borane and borane-methyl sulfide complex. Suitable organic solvents are diethyl ether, tetrahydrofuran, diglyme and ethylene glycol dimethyl ether or aromatic solvents such as, for example, benzene or toluene. The reduction can be performed at a temperature of between 0° C. and the reflux temperature of the organic solvents.

In step B6 the compound of formula 11 can be converted to the methylamino phenol, the compound of formula 12 by the same methods that were described above for the transformation of compound 9 to compound 10.

In step B7, if it is desired, the hydroxy group of the compound of the formula 12 may be acylated with R—C(═O) halogen or $(RCO)_2O$ where R is $C1$-$C_6$alkyl, by procedures well known in the art, to produce a compound of the formula 12a.

Scheme B'

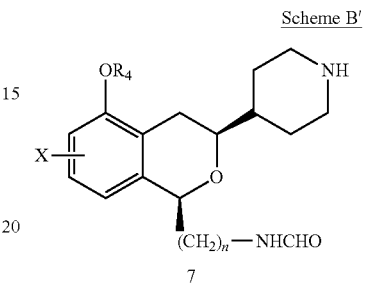

7

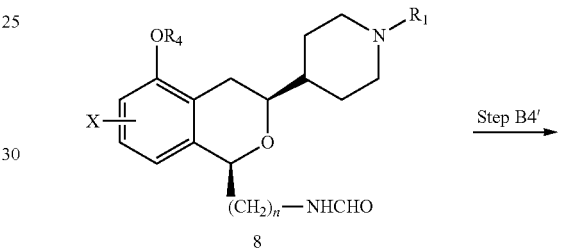

8

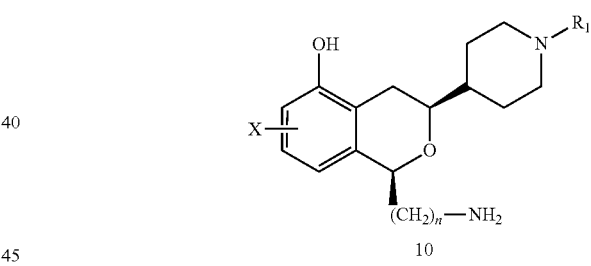

10

As a further alternative, compounds of formula I wherein $R_1$ is diphenyl$C_{1-6}$alkyl, benzyl, phenyl$C_{2-6}$alkyl, $C_{3-6}$cycloalkyl$C_{1-6}$alkyl, phenyl$C_{1-6}$alkylene heteroaryl$C_{1-6}$alkyl, phenylcarbonyl$C_{1-6}$alkyl, biphenyl$C_{1-6}$alkyl, and $C_{1-6}$alkyl may be prepared according to the sequence illustrated in Scheme B'. Accordingly, in step B1' compound of formula 7 is reacted with an alkyl halide or sulfonate in the presence of a suitable base and a suitable solvent to effect an alkylation resulting in the compound of formula 8. Suitable alkyl halides are for example chlorides, bromides or iodides and suitable sulfonates are mesylates or tosylates. Suitable bases for the reaction are triethylamine, diisopropylethylamine and potassium carbonate. Suitable solvents for the reaction are polar, aprotic solvents such DMSO, DMF, tetrahydrofuran and acetonitrile. The reaction temperature is not critical but typically the reaction is run at from ambient temperature to 75° C. The compounds thus obtained may be further modified as in step B4', analogous to step B4, to give compounds of formula 10.

Scheme C

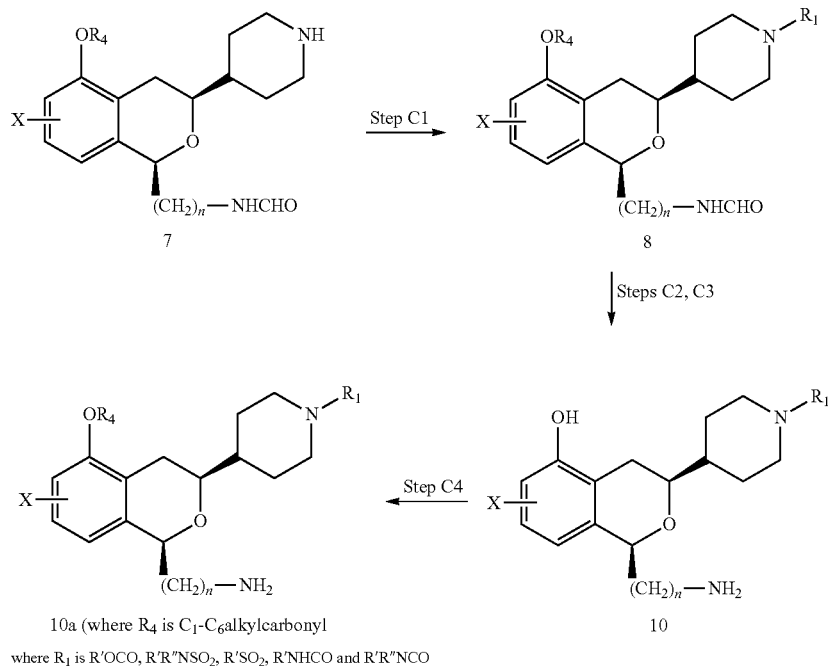

10a (where R₄ is $C_1$-$C_6$alkylcarbonyl where $R_1$ is R'OCO, R'R''NSO₂, R'SO₂, R'NHCO and R'R''NCO Scheme C depicts the synthesis of compounds wherein $R_1$ is phenoxycarbonyl, $C_{1-6}$alkoxycarbonyl, benzyloxycarbonyl, naphthyloxycarbonyl, phenylcarbamoyl, biphenylcarbamoyl, phenyl$C_{1-6}$alkylcarbamoyl $C_{1-6}$alkyl and $C_{1-6}$dialkylcarbamoyl, $C_{2-6}$alkenyl and $C_{2-6}$dialkenylcarbamoyl, diphenylcarbamoyl, heteroarylcarbamoyl, phenylcarbonyl, $C_{1-6}$alkylcarbonyl, 4-morpholinylcarbonyl, 1-piperidinylcarbonyl, pyrrolidinylcarbonyl, 10-phenothiazinylcarbonyl, phenylsulfonyl, diphenylsulfonyl, naphthylsulfonyl, $C_{1-10}$alkylsulfonyl, naphthyl $C_{1-6}$alkylsulfonyl, $C_{1-6}$perfluoroalkylsulfonyl, diphenyl$C_{1-6}$alkylsulfonyl, benzenesulfonyl, $C_{1-6}$dialkylaminosulfonyl. Thus, in step C1 compound of the formula 7 may be reacted with phenyl haloformates, alkylhaloformates, benzylhaloformates, naphthylhaloformates, phenylcarbamoyl halides, biphenylcarbamoyl halides, phenylalkylcarbamoyl halides, biphenylcarbamoyl halides, heteroarylcarbamoyl halides, phenylalkylcarbamoyl halides, alkyl and dialkylcarbamoyl halides, alkenyl and dialkenylcarbamoyl halides, diphenylcarbamoyl, phenyl isocyanates, biphenylisocyanates, alkenyl isocyanates, phenylcarbonyl halides, alkylcarbonyl halides, 4-morpholinylcarbonyl halides, 1-piperidinylcarbonyl halides, pyrrolidinylcarbonyl halides, 10-phenothiazinylcarbonyl halides, phenylsulfonyl halides, diphenylsulfonyl halides, naphthylsulfonyl halides, 1-alkylsulfonyl, naphthylalkylsulfonyl halides, perfluoroalkylsulfonyl halides, diphenylalkylsulfonyl halides, benzenesulfonyl halides, and dialkylaminosulfonyl halides in the presence of suitable base in a suitable organic solvent to produce the compound of the formula 8. Suitable bases are tertiary amines such as diisopropylethylamine, triethylamine and triisopropylamine suitable solvents are alkylhalides such as dichloromethane, chloroform and dichloroethane, aromatic solvents such as benzene, toluene and xylenes and ethereal solvents such as diethyl ether, tetrahydrofuran diglyme and ethylene glycol dimethyl ether. The reactions are typically run from 0° C. to the boiling point of the organic solvent.

In steps C2 and C3 the primary amine compound 10 can then obtained by hydrolysis of compound 8 by methods previously described for the transformation of compound 8 to compound 10 as shown in Scheme B, step B2 and B3.

In step C4, if it is desired, the hydroxy group of the compound of the formula 10 may be acylated with R—C(=O) halogen or (RCO)₂O where R is C1-$C_6$alkyl, by procedures well known in the art, to produce a compound of the formula 10a.

Scheme D

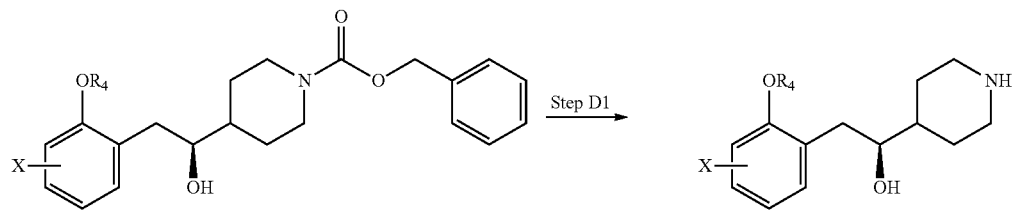

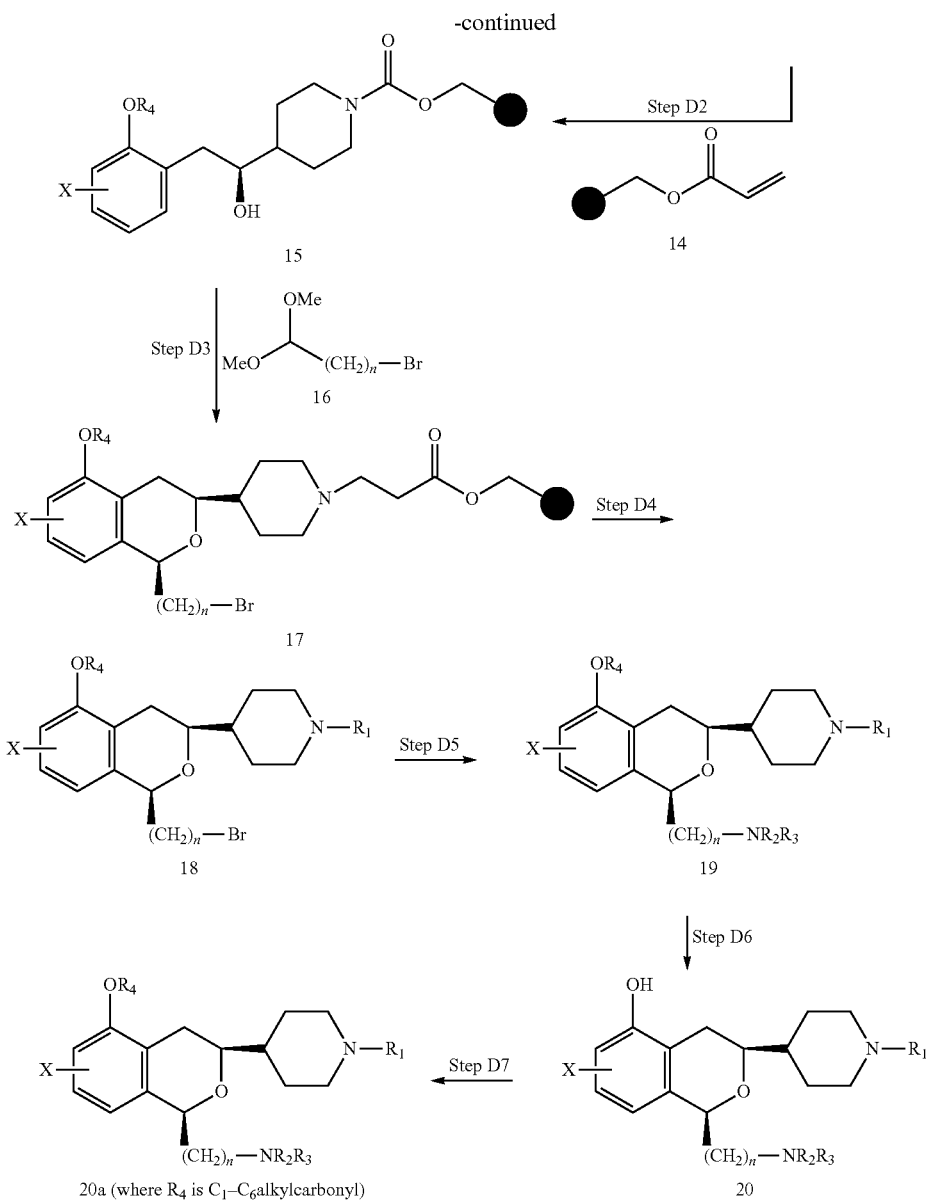

Scheme D depicts the use of solid phase methodology for the preparation of compounds of the instant invention.

The compound of formula 13, which is generated from compound 5 (see Scheme A), by reaction with benzyl chloroformate under conditions well known in the art (see T. W. Greene, et al. *Protective Groups in Organic Chemistry*, 2$^{nd}$ Edition, John Wiley & Sons, Inc. New York, 1991, p 335) and is prepared as a readily purified, easily stored intermediate to compound 5. As shown in step D1 the intermediate hydroxy piperidine of formula 5 can be regenerated for further elaboration from compound 13 by hydrogenation to cleave the benzyloxycarbonyl group. The hydrogenation step can be accomplished in a suitable organic solvent in the presence of a suitable catalyst. Suitable organic solvents are alcohols and organic acids, for example alcohols such as methanol, ethanol, isopropanol and the like or organic acids such as formic acid, acetic acid, propionic acid and the like. Suitable catalysts are palladium on carbon, palladium hydroxide, palladium chloride, palladium oxide platinum oxide, platinum on carbon and ruthenium on carbon. The hydrogenation is typically carried out at a temperature of ambient or above, but below the boiling point of the organic solvent.

In step D2 the formation of the resin-bond piperidine of formula 15 maybe accomplished by reaction of the compound of formula 8 with REM resin, 14 in a suitable organic solvent. Suitable organic solvents are aprotic polar organic solvents such as dimethylformamide (DMF), N-methylpyrrolidine (NMP) and dimethylsulfoxide (DMSO), and typically the reaction can be achieved at a temperature of between ambient temperature and the reflux temperature of the solvent.

In step D3 the resin bound reagent of formula 15 is then reacted with a bromoalkylaldehyde dimethyl acetal of formula 16, with a suitable Lewis acid catalyst in a suitable inert organic solvent to effect the cyclization to the resin bound bromoalkylisochroman of formula 17 (see M. R. Michaelides, et al. *J. Med. Chem.*, 1991, 34 2946-2953). Examples of suitable Lewis acid catalysts are trimethylsilyl triflate, borontrifluoride diethyl etherate, titanium tetrachloride and zinc triflate. Suitable inert organic solvents are hydrohalocarbon solvents such as dichloromethane, aromatic hydrocarbons such as benzene, toluene and the like and acetonitrile. The reaction may be carried out at a suitable temperature such as within the range of 0° C. to room temperature.

In step D4 concomitant displacement of the resin and functionalization of the piperidine nitrogen is effected to produce the compound of the formula 18. In a two-step procedure, the resin bound isochroman of formula 17 is first reacted with a diphenylalkyl halide, benzyl halide, phenylalkyl halide, alkylcycloalkylalkyl, halide, phenylalkylenealkyl halide, heteroarylalkyl halide, phenylcarbonylalkyl halide, hydroxyalkyl halide, biphenylalkyl halide, alkyl halide, indanyl halide in the presence of a suitable solvent followed by treatment of the intermediate quaternized salt with a suitable base in a suitable solvent to produce the N-substituted intermediate 18. Suitable reaction solvents for the first step are aprotic polar solvents such as NMP, DMF and DMSO. For the second step suitable solvents are alkylhalides such as dichloromethane, chloroform and dichloroethane, aromatic solvents such as benzene, toluene and xylenes and ethereal solvents such as diethyl ether and tetrahydrofuran. Suitable bases are tertiary amines such as diisopropylethylamine, triethylamine and triisopropylamine The reactions may be carried out at a suitable temperature such as within the range of 0° C. to room temperature.

In step D5 reaction of the bromo intermediate formula 18 with a secondary amine produces the tertiary amine compound of the formula 19. The reaction is typically run in a suitable inert organic solvent such as alcohols or aromatic hydrocarbons with an excess of the appropriate secondary amine. The reaction may be run in an open or closed vessel at a temperature within the range of ambient to reflux temperature of the reaction medium.

In step D6 the cleavage of the O-alkoxy group of compound 19 can be readily accomplished by standard methods well known in the art and described above in Scheme B step B3 and step B4 to afford the 5-hydroxyisochroman of formula 20.

In step D7 if it is desired, the hydroxy group of the compound of the formula 20 may be acylated with R—C(═O) halogen or (RCO)$_2$O where R is C1-C$_6$alkyl, by procedures well known in the art, to produce a compound of the formula 20a.

Scheme E

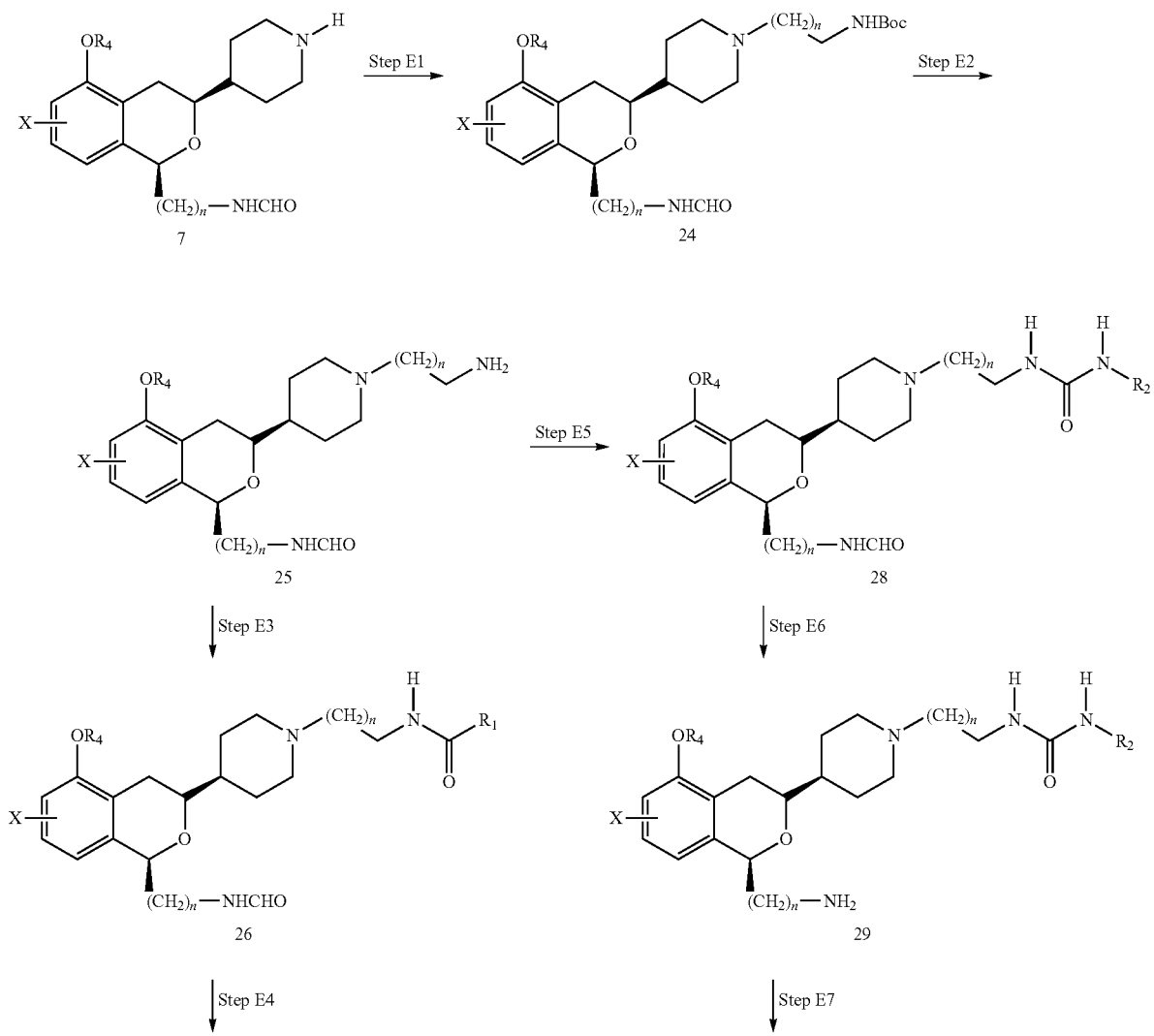

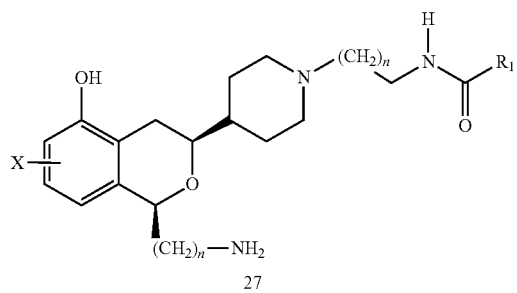

27

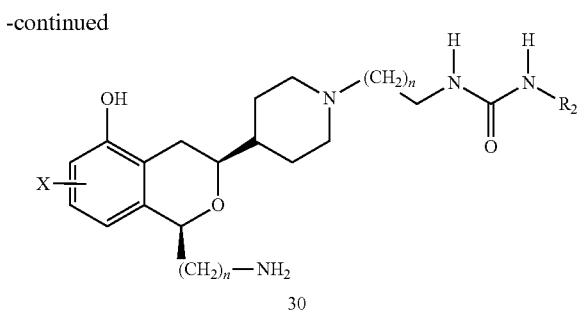

30

Compounds of formula I wherein $R_1$ is arylcarbonylamino$C_{1-6}$alkyl or arylcarbamoylamino$C_{1-6}$alkyl may be prepared according to the sequence illustrated in Scheme E. Accordingly, in step E1 compound of formula 7 is reacted with a protected aminoaldehyde such as t-butyl N-(2-oxoethyl)carbamate in the presence of a suitable borohydride and a suitable solvent to effect a reductive amination resulting in the compound of formula 24. Suitable borohydrides are, for example, sodium borohydride, sodium triacetoxy borohydride, sodium cyanoborohydride and sodium borohydride in conjunction with titanium isopropoxide may be used. Suitable solvents for the reaction are halogen containing solvents such dichloromethane, chloroform and dichloroethane, alcoholic solvents such as methanol, ethanol and isopropanol, ethereal solvents such as diethyl ether and tetrahydrofuran and acetonitrile. The reaction temperature is not critical but typically the reaction is run at from 0° C. to ambient temperature.

As further illustrated in Scheme E, step E2, the Boc group of compound 24 can be readily cleaved to produce the primary amine, compound 25, which can undergo further reactions to give other desired derivatives. The cleavage can be effected under acidic conditions, methods well known to those skilled in the art. For instance, the Boc group may be removed by treatment with hydrogen chloride in ethyl acetate or trifluoroacetic acid in dichloromethane.

In step E3 compound 25 may be reacted with benzoyl chlorides in the manner described in Scheme C, step C1 to give compounds of formula 26. Concomitant cleavage of the arylalkyl ether and the formyl group to yield compounds of formula 27 may be accomplished as described in Scheme B, step B4.

Alternatively, in step E5, compound 25 may be reacted with isocyanates in the manner described in Scheme C, step C1 to give compounds of formula 28. The arylalkyl ether and the formyl group of such compounds may then be cleaved in a two step process (steps E6 and E7) as described in Scheme B, steps B2 and B3 to yield compounds of formulas 29 and 30.

Scheme F

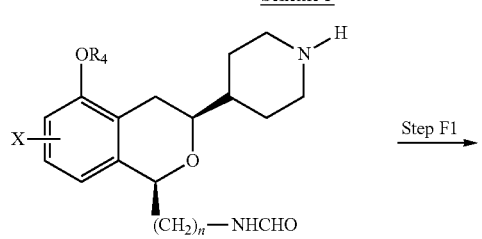

7

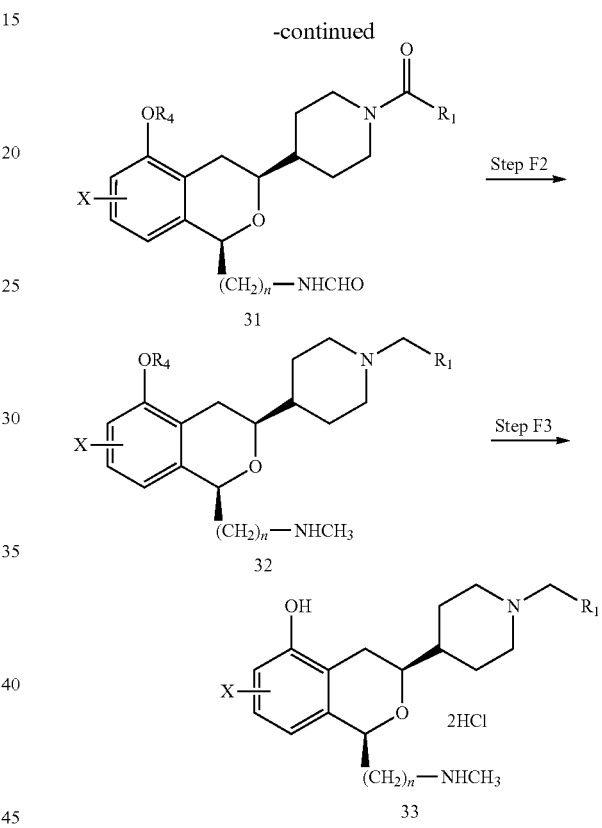

Compounds of formula I wherein $R_1$ is diphenyl$C_{1-6}$alkyl, benzyl, phenyl$C_{2-6}$alkyl, $C_{3-6}$cycloalkyl$C_{1-6}$alkyl, heteroaryl$C_{1-6}$alkyl, biphenyl$C_{1-6}$alkyl and $C_{1-6}$alkyl may be prepared according to the sequence illustrated in Scheme F. Accordingly, in step F1 compound of formula 7 is reacted with an acylating agent in the presence of a suitable base resulting in the compound of formula 31. Suitable acylating agents are for example acid halides, anhydrides or mixed anhydrides. Suitable bases are triethylamine, diisopropylethylamine and pyridine. Suitable solvents for the reaction are halogen-containing solvents such as dichloromethane, chloroform and dichloroethane, ethereal solvents such as diethyl ether and tetrahydrofuran, and acetonitrile. The reaction temperature is not critical but typically the reaction is run at from 0° C. to ambient temperature.

As further illustrated in Scheme F, step F2, treatment of compound 31 with a reducing agent reduces both carbonyl groups to give the compound of formula 32. Suitable reducing agents are lithium aluminum hydride, sodium bis(2-methoxyethoxy) aluminum hydride, and diborane. Suitable solvents for the reaction are ethereal solvents such as diethyl ether and tetrahydrofuran and aromatic hydrocarbons such as benzene and toluene. Typically the reaction is run at from 0° to the boiling point of the solvent. Cleavage of the arylalkyl ether to yield compounds of formula 33 may be accomplished as described in Scheme B, step B4.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

BIOLOGICAL EXAMPLES

The following test protocols are used to ascertain the biological properties of the compounds of this invention.

[$^3$H]-SCH-23390 Binding to Cloned Human Dopamine $D_1$ Receptors

Purpose:

Determination of relative binding affinity of potential neuropsychiatric and other agents for the human dopamine $D_1$ receptor.

Procedure:

A. Cloning

The human D, cDNA was obtained from the laboratory of Dr. Marc Caron in the vector pCMV5. A 1.4 Kb Hind III to Xho I fragment was subcloned into the vector pMMLV. The plasmid pHD1MMLV was then sequenced completely. Transient transfections in COS-7 cells were performed and $D_1$ specific binding was obtained. The construct pHD1MMLV was then transfected stably into CHO cells and 72 G418-resistant clones were isolated. High expressors were identified by mRNA dot blot analysis. Six high expressors were further characterized by binding and then clone CHO-$D_1$M#9 was chosen for detailed pharmacological characterization. This clone was then grown in suspension culture for the purpose of obtaining enough protein to accommodate several months of screening.

B. Cell Culture Conditions
  1. Medium for adherent CHO cultures:
     Ham's F12+10% fetal bovine serum (FBS)+400 µg/ml geneticin
     (G418)+10 ml/L penicillin-streptomycin (P/S).
  2. Cells are transferred to suspension culture when at least 1.5 million cells are available (this allows for 300,000 cells/ml in a 50 ml spinner flask; this is the ideal suspension density). Cells are removed from flasks with trypsin, spun down at 1000×G and resuspended the pellet in fresh medium:
     50% CHO-SFM-II+50% Ham's F12 w/10% FBS (final FBS conc. 5%)+400 µg/ml G418+1% P/S.
  3. After the transfer to suspension culture, growth is monitored and cell viability is assessed using trypan blue exclusion. Total and viable cell count on 5 sectors of the hemocytometer are recorded. When the viable cell density reaches 600,000 cell/ml, the volume is doubled.
  4. After 1 week of growth in the 50/50 medium, the cells are spun down and transferred to a new spinner flask and replaced with 75% CHO-SFM II/25% Ham's F12+10% FBS plus the pen-strep and G418. Thereafter every 3 days, the medium is replaced with new medium containing a decreasing amount of FBS as follows:

| ml of CHO SFM:ml of Ham'S F12 | Final % FBS conc. |
|---|---|
| 87.50:12.5 | 1.25 |
| 93.75:6.25 | 0.625 |
| 99.00:1.00 | 0.1 |

5. The final maintenance culturing medium is made up as follows:
     A stock mixture of 10 ml of pen-strep, 0.5 ml of 400 µg/ml (active; final concentration: 200 µg/ml) G418 and 1 ml of FBS are mixed and filtered and refrigerated. A volume (11.5 ml) of this mixture is added to a freshly opened 1 L bottle of CHO-SFM II.

C. Membrane Preparation

Cells are harvested into 250 ml centrifuge tubes and spun down at 1200×G. The medium is removed and 100 ml PBS (phosphate-buffered saline) is added to each centrifuge tube; cells are resuspended and spun down again. The PBS is removed and the final pellet is homogenized with a polytron on ice at a medium setting.

D. Lowry Protein Assay

The membrane suspension is diluted in water and samples (10, 50 and 100 µl; q.s. to 100 µl with water) are diluted with 100 µl of 1% SDS. The sample is vortexed and allowed to stand for 5 min. Two aliquots each of the solubilized protein sample are placed in clean 13×100 test tubes for the assay. Instructions are followed as outlined in the BioRad DC protein determination kit (Catalog # 500-0112). OD readings that fall between 0.1-0.5 (mid-range of standard curve) should typically be used for calculations. Protein concentrations are calculated from a standard curve using bovine serum albumin as standard by linear regression and interpolation.

E. Freezing/Storage

Following cell harvesting and protein determination, the homogenate is diluted with 10% DMSO to the correct volume based on $B_{max}$ and relative size of individual experiments to be conducted. The concentrated protein is stored in cryogenic vials in aliquots of 1-1.5 ml. Samples may be stored in −80° C. freezer or in liquid nitrogen.

F. Binding Reagents 1. a) 0.5M Tris Buffer, pH 7.7
   57.2 g Tris HCl
   16.2 g Tris Base
   q.s. to 1 L with distilled water
   b) 0.05M Tris Buffer, pH 7.7
   make a 1:10 dilution of (a) in distilled water
2. a) Tris Buffer Containing Physiological Ions
   NaCl 7.014 g
   KCl 0.372 g
   $CaCl_2$ 0.222 g
   $MgCl_2$ 0.204 g
   q.s. to 1 L with 0.5M Tris buffer, pH 7.7
   b) Dilute buffer (a) 1:10 in distilled water
   This yields 0.05M Tris buffer, pH 7.7 containing 120 mM NaCl, 5 mM, KCl, 2 mM $CaCl_2$ and 1 mM $MgCl_2$.
3. a) 3% polyethyleneimine stock in 0.5M Tris (reagent 1.a)
   b) Dilute (a) 1:10 in 0.05M Tris (reagent 1.b) for final concentration of 0.3% polyethyleneimine.
4. [N-methyl-$^3$H]-SCH-23390 (67-73 Ci/mmol) is obtained from New England Nuclear (Catalog# Net-930).
   For $IC_{50}$ and $K_i$ determinations: [$^3$H]-SCH-23390 is made up to a concentration of 6.7 nM in Tris buffer 2b and 150 µl is added to each tube. This addition yields a final concentration of 1 nM [$^3$H]-SCH-23390 in the 1 ml assay.
5. d-Butaclamol is obtained from Research Biochemicals, Inc.
   A 100 µM stock is made in distilled water and diluted 1:3.3 in Tris buffer 2b. 100 µl of diluted stock is added to 3 test tubes for the determination of nonspecific binding. (This addition yields a final concentration of 3 µM d-butaclamol in the 1 ml assay).
6. Test Compounds
   For most assays, a 1 mM stock solution is made up in a suitable solvent (usually <0.1% glacial acetic acid) and serially diluted, such that the final concentration in the assay ranges from $10^{-5}$ to $10^{-9}$ M. Higher or lower concentrations may be used depending on the potency of the drug.

G. Tissue Preparation

Samples of cell membranes (previously prepared and frozen) are removed from the freezer and allowed to thaw. Membranes are diluted to the appropriate concentration (between 50-500 µg protein/assay point depending on expression levels) in Tris buffer 2b and homogenized with a polytron at a medium setting.

H. Assay

750 µl cell membrane suspension
150 µl [$^3$H]-SCH-23390
100 µl vehicle (total binding), butaclamol (NSB) or appropriate drug concentration 96-Well Method:

The 96-Well Packard Unifilters GF/B are incubated for >1 h at 25° C. in 0.1% polyethylamine (from 3.b). The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min under a heat lamp or incubated for 15 min in a 60° C. oven) and a bottom seal is applied. Then 40 µl of Packard Microscint 20 scintillation cocktail is added and a permanent topseal (Type P) is applied and heat sealed. The plates are then shaken on an orbital shaker for 1 h and placed in the Packard Topcount and counted for at least 5 minutes for each point.

Test Tube Method:

The tubes are incubated at 37° C. for 30 minutes in a shaking water bath. The assay is stopped by rapid filtration through Whatman GF/B filters (presoaked in 0.3% polyethyleneimine, reagent 3b) using a Brandel Cell Harvester. The filter strips are then washed three times with 5 ml ice-cold 0.05M Tris buffer, pH 7.7, and counted in 5 ml of Ecoscint scintillation cocktail. Specific binding is defined as the difference between total binding and binding in the presence of 3 µM d-butaclamol. $IC_{50}$ calculations are performed using GraphPad Prism software; nonlinear regression, one-site competition analysis with top and bottom limits held constant at 0% and 100% inhibition, respectively. The percent inhibition at each drug concentration is the average of duplicate determinations. $K_i$ values are also calculated using Prism software, or by the following formula:

$$K_i = \frac{IC_{50}}{1 + L/K_d},$$

where L=ligand concentration in experiment and $K_d$=dissociation constant of the ligand The experimental ligand concentration (L) is determined by the average CPMs obtained from two samples of the [$^3$H]-SCH-23390 stock added in the assay.

[N-Methyl-$^3$H]Spiroperidol Binding to Cloned Human Dopamine D2Long Receptors

This assay measures the in vitro activity of drugs on cloned human dopamine D2Long ($D_{2L}$) receptors and predicts the direct dopamine-displacing properties of neuropsychiatric, cardiovascular and renal agents at human dopamine $D_2$ receptors.

Human $D_{2L}$ Cone:

The $D_{2L}$ gene was isolated from a human striatal (caudate/putamen) cDNA library. The gene was sequenced and subcloned into the expression vector pRC/RSV (Invitrogen). CHO (Chinese Hamster Ovary) cells were stably transfected and 72 clones that were geneticin (G418) resistant were isolated. Using mRNA and binding data a single high expressing cell line was identified (#44). A clone expressing high levels of the receptor (as determined by mRNA and receptor binding data) was chosen and pharmacologically characterized.

Cell Culture:
1. CHO cells expressing the human dopamine $D_2$ receptor were maintained by splitting at a ratio of 1:10. Cells were maintained in Ham's F12+10% Fetal Bovine Serum+Penicillin/Streptomycin (100 U/ml/100 µg/ml)+G418 (400 µg/ml) medium and were split using Trypsin-EDTA (1 ml/plate, room temperature for ~2 min. or until cells have lifted off plates).
2. Stock plates were subcultured into 90 large plates over 2 weeks, and 1.5 large plates were split into one roller bottle (90 ml of culture medium per roller bottle).
3. Plates are incubated at 37° C.+5% $CO_2$ for ~3 days or until cells were confluent. Cells are spun at 30-40% motor speed in the Forma incubator.

Storage

Cells are harvested by mechanical scraping, washed using PBS collected in 250 ml Corning polypropylene centrifuge tubes, spun down and resuspended in $dH_2O$ (final volume per harvest approximately 60 ml). Protein determination is made according to the method of Lowry (Biorad DC Assay Kit). Following the determination of the protein concentration, the protein is diluted into distilled water with 10% DMSO to the appropriate volume based on expression levels ($B_{max}$). The concentrated protein is aliquoted into 1.5 ml screw top eppendorf tubes and placed into a −80° C. freezer.

Assay Requirement: 1 cryovial per two 96 well plates
[$^3$H]-Ligand: [N-methyl-$^3$H]-Spiroperidol (60-90 Ci/mmol) at 0.4 nM (NEN-856)
$K_D$=0.08 nM
Materials: S(−)-Eticlopride (Research Biochemicals Int. E-101)
   96 well 2.2 ml Cubestubes (BelArt)
   Unifilter GF/B Plate (Packard)
   Polyethylenimine (Sigma #P-3134)
   TomTec Cell Harvesters
   Packard TopCount Scintillation Counter
Buffers: Binding Assay Reagents
1. 0.5M Tris Wash Buffer, pH 7.7
   a) 44.4 g Tris HCl
      26.5 g Tris Base
      q.s. to 1 Liter (0.5 M Tris buffer, pH 7.7 at 37° C.)
   b) make a 1:10 dilution in distilled $H_2O$ (0.05 M. Tris buffer, pH 7.7)
2. Tris Buffer containing physiological salts
   a) Stock buffer
      NaCl 7.014 g
      KCl 0.372 g
      $CaCl_2$ 0.222 g
      $MgCl_2$ 0.204 g
      q.s. To 100 ml with 0.5 M. Tris Buffer
   b) Dilute 1:10 in distilled $H_2O$
      This yields 0.05 M. Tris HCl, pH 7.7, containing NaCl (120 mM), KCl (5 mM), $CaCl_2$ (2 mM) and $MgCl_2$ (1 mM)
      Optional: add 0.1% ascorbic acid and check pH (in assays with compounds that may oxidize.
   c) 1.0% polyethyleneimine stock in 0.5M Tris (reagent 1.a)
      Dilute 1:10 in distilled $H_2O$ Binding Assay
   750 µl Tissue
   150 µl [$^3$H]NMSP
   100 µl vehicle (for total binding) or 30 µM (−) eticlopride (for nonspecific binding) or appropriate drug concentration.

The 96-Well Packard Unifilters GF/B are incubated for >1 h at 25° C. in 0.1% polyethylenimine. The cold tissue is added last and mixed on a orbital shaker for a few seconds and is then incubated at 37° C. for 30 min in a shaking water bath. The assay is stopped by rapid filtration through Packard Unifilter plates. The filter membranes are then washed with 15 ml of ice-cold 0.05 M Tris buffer. The filters are then dried (~15 min. under a heat lamp or incubated for 15 min. in a 60° C. oven) and a bottom seal is applied. Then 40 µl of Packard Microscint 20 scintillation cocktail are added and a permanent topseal (Type P) is applied and heat sealed. The plates are placed in a Packard Topcount.

Analysis of Results:

Specific binding is defined as the difference between total binding and the binding in the presence of 3 µM S-(−)-eticlopride. Total binding is approximately 10% of the total added ligand. Cheng-Prusoff determination ($K_i$'s) are performed using Prism software using a one-site competition curve analysis where the top and the bottom of the non-linear regression are held constant at 0% and 100% percent inhibition. The percent inhibition at each drug concentration is the mean of duplicate determinations.

Variants: Beckman 1000 Robotic assay (200 µl assay volume)
Assay Requirement: 1 cryovial per four 96 well plates
[$^3$H]-Ligand: [$^3$H] [N-methyl-3H]-Spiroperidol (60-90 Ci/mmol) at 1.5 nM (NEN-856)
$K_D$=0.6 nM
Materials: S(−)-Eticlopride (Research Biochemicals Int. E-101)
   96 well polystyrene plate (Beckman)
   Unifilter GF/B Plate (Packard)
   Polyethylenimine (Sigma #P-3134)
   TomTec Cell Harvesters
   Packard TopCount Scintillation Counter
Binding Assay
   100 µl Tissue
   50 µl [$^3$H]NMSP
   50 µl vehicle (for total binding) or 50 µM (−)eticlopride (for nonspecific binding) or appropriate drug concentration.

The 96-Well Packard Unifilters GF/B are incubated for >1 h at 25° C. in 0.1% polyethylamine. The room temperature tissue is added last and is then incubated at 37° C. for 60 min. in a Beckman SL incubator. The assay is stopped by rapid filtration through Packard Unifilter plates. The filter membranes are then washed with ~7 ml of ice-cold 0.05 M Tris buffer. The filters are then dried (~15 min. under a heat lamp or incubated for 15 min. in a 60° C. oven) and a bottom seal is applied. Then 40 µl of Packard Microscint 20 scintillation cocktail is added and a permanent topseal (Type P) is applied and heat sealed. The plates are then placed in the Packard Topcount and counted for 2 min for each point.

Analysis of Results:

Specific binding is defined as the difference between total binding and the binding in the presence of 5 µM S-(−)-eticlopride. Total binding is approximately 10% of the total added ligand. Cheng-Prusoff determination ($K_i$'s) are performed using Excel Fit software using a one-site competition curve analysis where the top and the bottom of the non-linear regression are held constant at 0% and 100% percent inhibition. The percent inhibition at each drug concentration is the mean of duplicate determinations.

The results for the competitive binding assay, reported as $K_i$, values for the $D_1$ and $D_2$ receptor are shown in Table 1

TABLE 1

Competitive Binding for D1 and D2 Receptors

| Example | R1 | R2 | R3 | D1 affinity Ki (nM) | D2 affinity Ki (nM) |
|---|---|---|---|---|---|
| 111 | —(CO)OC(CH₃)₂ | H | H | 165 | 794 |
| 112 | —(CO)OCH₃ | H | H | 101 | ≧100,000 |
| 113 | phenyl carbonate | H | H | 30.5 | ≧100,000 |
| 114 | 4-methylphenyl carbonate | H | H | 64.6 | 511 |
| 115 | 4-chlorophenyl carbonate | H | H | 39 | 506 |
| 116 | 2-chlorophenyl carbonate | H | H | 32.6 | ≧100,000 |
| 117 | 4-bromophenyl carbonate | H | H | 59 | 404 |
| 118 | 4-fluorophenyl carbonate | H | H | 40 | 10,000 |
| 119 | 2-trifluoromethylphenyl carbonate | H | H | 54 | 649 |
| 120 | 4-methoxyphenyl carbonate | H | H | 45 | 767 |

TABLE 1-continued
Competitive Binding for D1 and D2 Receptors
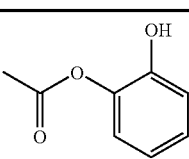
| Example | R1 | R2 | R3 | D1 affinity Ki (nM) | D2 affinity Ki (nM) |
|---|---|---|---|---|---|
| 121 | 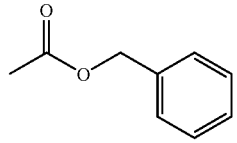 | H | H | 31 | 613 |
| 122 | 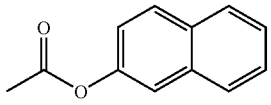 | H | H | 92 | 751 |
| 123 | 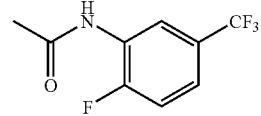 | H | H | 37 | 154 |
| 124 | 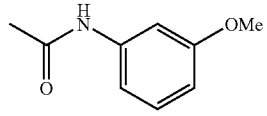 | H | H | 486 | 10,000 |
| 125 | 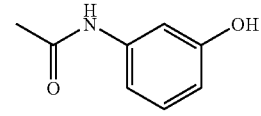 | H | H | 79 | 10,000 |
| 126 | 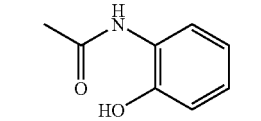 | H | H | 21 | 328 |
| 127 | 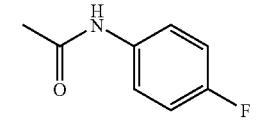 | H | H | 105 | 10,000 |
| 128 | 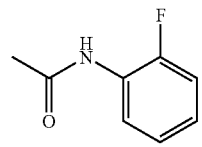 | H | H | 106 | 10,000 |
| 129 |  | H | H | 113 | 10,000 |

TABLE 1-continued
Competitive Binding for D1 and D2 Receptors
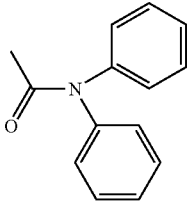
| Example | R1 | R2 | R3 | D1 affinity Ki (nM) | D2 affinity Ki (nM) |
|---|---|---|---|---|---|
| 130 | 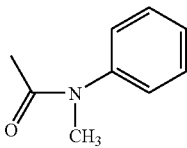 | H | H | 156 | 536 |
| 131 | 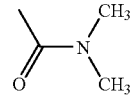 | H | H | 51 | 10,000 |
| 132 | 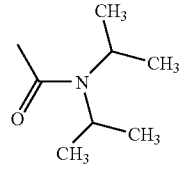 | H | H | 256 | ≧100,000 |
| 133 | 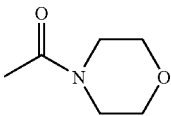 | H | H | 241 | ≧100,000 |
| 134 | 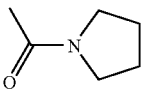 | H | H | 240 | ≧100,000 |
| 135 | 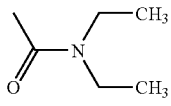 | H | H | 61.5 | ≧100,000 |
| 136 | 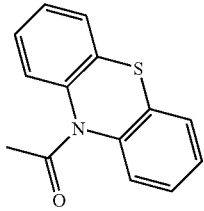 | H | H | 162 | ≧100,000 |
| 137 |  | H | H | 412 | 163 |

TABLE 1-continued

Competitive Binding for D1 and D2 Receptors

[Structure: isochroman with OH, CH3, S and R stereocenters, piperidine with N-R1, and CH2-N(R2)(R3) substituent]

| Example | R1 | R2 | R3 | D1 affinity Ki (nM) | D2 affinity Ki (nM) |
|---|---|---|---|---|---|
| 138 | acetyl-piperidine | H | H | 198 | ≥100,000 |
| 139 | C(O)N((CH2)3CH3)2 | H | H | 137 | 204 |
| 140 | C(O)N(CH=CHCH3)2 | H | H | 125 | ≥100,000 |
| 141 | —SO2—C6H5 | H | H | 193 | ≥100,000 |
| 142 | —SO2—CH2—C6H5 | H | H | 18 | ≥100,000 |
| 143 | —SO2—(2-CF3-C6H4) | H | H | 167 | 777 |
| 144 | —SO2—(3,4-(OMe)2-C6H3) | H | H | 91 | 602 |
| 145 | —SO2—(4-iPr-C6H4) | H | H | 146 | 288 |
| 146 | —SO2—(4-tBu-C6H4) | H | H | 89 | 531 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 147 | —SO₂-(2-naphthyl) | H | H | 108 | 623 |
| 148 | —SO₂-(4-chlorophenyl) | H | H | 183 | ≥100,000 |
| 149 | —SO₂-(2,4-dichlorophenyl) | H | H | 213 | 589 |
| 150 | —SO₂-(3,4-dichlorophenyl) | H | H | 256 | ≥100,000 |
| 151 | —SO₂-(2,5-dichlorophenyl) | H | H | 82 | ≥100,000 |
| 152 | —SO₂-(4-biphenyl) | H | H | 169 | ≥100,000 |
| 153 | —SO₂-CH₂CH₃ | H | H | 250 | ≥100,000 |
| 154 | —SO₂-(CH₂)₃CH₃ | H | H | 270 | ≥100,000 |
| 155 | —SO₂-CH(CH₃)₂ | H | H | 217 | ≥100,000 |
| 156 | —SO₂-(CH₂)₇CH₃ | H | H | 139 | ≥100,000 |
| 157 | —SO₂-CH₂CF₃ | H | H | 2.07 | 434 |

TABLE 1-continued
Competitive Binding for D1 and D2 Receptors
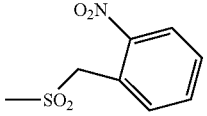
| Example | R1 | R2 | R3 | D1 affinity Ki (nM) | D2 affinity Ki (nM) |
|---|---|---|---|---|---|
| 158 | 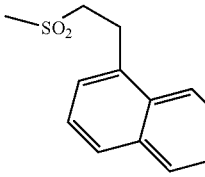 | H | H | 95.2 | ≧100,000 |
| 159 | 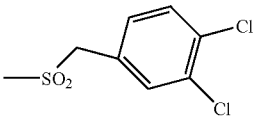 | H | H | 64.5 | ≧100,000 |
| 160 | 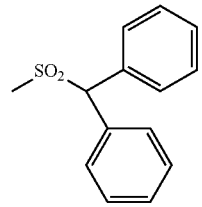 | H | H | 264 | ≧100,000 |
| 161 | 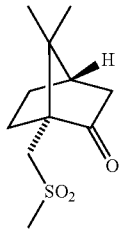 | H | H | 3.6 | 1.85 |
| 162 | 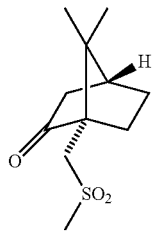 | H | H | 382 | ≧100,000 |
| 163 | 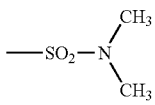 | H | H | 320 | ≧100,000 |
| 164 | —SO$_2$—N(CH$_3$)(CH$_3$) | H | H | 400 | ≧100,000 |

TABLE 1-continued
Competitive Binding for D1 and D2 Receptors
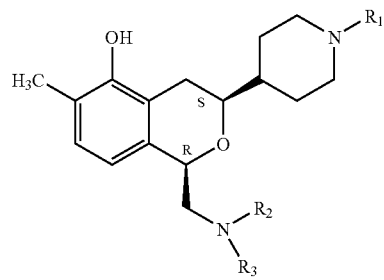
| Example | R1 | R2 | R3 | D1 affinity Ki (nM) | D2 affinity Ki (nM) |
| --- | --- | --- | --- | --- | --- |
| 165 | —SO$_2$—N(piperidine) | H | H | 227 | 10,000 |
| 166 | 4-benzylpiperidine-1-sulfonyl | H | H | 207 | 246 |
| 167 | 1,2,3,4-tetrahydroisoquinoline-2-sulfonyl | H | H | 74 | 528 |
| 102 | —CH$_3$ | —CH$_3$ | H | 147 | |
| 106 | —CH$_2$CH$_2$CH$_2$-phenyl | H | H | 45 | 278 |
| 107 | —CH$_2$CH$_2$CH$_2$-(3-chlorophenyl) | H | H | 926 | 10,000 |
| 108 | —CH$_2$CH(4-F-phenyl)$_2$ with butyl | H | H | 110 | |
| 28 | —CH(CH$_2$CH$_3$)(diphenyl) •HBr | H | H | 82 | 180 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 29 | CH(CH3)-phenyl | H | H | 64 | 10,000 |
| 30 | CH2CH(CH3)-phenyl (isobutyl-phenyl) | H | H | 55.2 | 10,000 |
| 26 | CH2CH2-(4-F-phenyl) | H | H | 33 | 10,000 |
| 105 | CH2CH=CH-phenyl (propenyl-phenyl) | H | H | 108 | 212 |
| 31 | CH2CH2-(3-OMe-phenyl) | H | H | 12 | 575 |
| 32 | 2-indanyl methyl · HBr | H | H | 22 | 127 |
| 33 | —(CH2)3CH3 | H | H | 70 | 10,000 |
| 34 | CH2-cyclohexyl | H | H | 47 | 10,000 |
| 35 | CH2CH2-(2-Cl-phenyl) | H | H | 42 | 96 |
| 36 | CH2CH2-(2-F-phenyl) | H | H | 42.8 | 749 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 37 | 3-chlorophenethyl | H | H | 17.9 | 356 |
| 105 | (2-methylbutyl)-6-fluorobenzisoxazole | H | H | 26 | 415 |
| 104 | (sec-pentyl)-6-fluorobenzisoxazole | H | H | 70 | 122 |
| 38 | cyclopropylmethyl | H | H | 53 | 10,000 |
| 194 | 1-phenyl-1-ethylpropyl (pentan-3-yl phenyl) | CH₃ | H | 54 | 639 |
| 169 | phenethyl | CH₃ | CH₃ | 158 | 172 |
| 170 | phenethyl | C₂H₅ | C₂H₅ | 1670 | 377 |
| 171 | phenethyl | CH₃ | H | 98 | 317 |
| 172 | phenethyl | C₂H₅ | H | 522 | 279 |
| 173 | phenethyl | CH₃ | C₂H₅ | 425 | 241 |
| 174 | phenethyl | (CH₂)₂CH₃ | H | 510 | 248 |

TABLE 1-continued

Competitive Binding for D1 and D2 Receptors

| Example | R1 | R2 | R3 | D1 affinity Ki (nM) | D2 affinity Ki (nM) |
|---------|----|----|----|---------------------|---------------------|
| 175 | CH2-phenyl | (CH2)2CH3 | CH3 | 3070 | 10,000 |
| 176 | CH2-phenyl | CH2CH=CHCH2 (but-2-enyl) | CH3 | 1700 | 124 |
| 177 | CH2-phenyl | c-C4H7 | H | 10,000 | 305 |
| 178 | CH2-phenyl | —(CH2)4— | | 10,000 | 181 |
| 179 | C(O)CH2CH2-phenyl | C2H5 | H | 139 | 215 |
| 180 | C(O)CH2CH2-phenyl | CH2CH=CHCH2 | CH2CH=CHCH2 | 642 | 86 |
| 181 | CH2CH2-(4-CF3-phenyl) | H | H | 57 | 655 |
| 182 | CH2CH2-(4-CF3-phenyl) | CH3 | H | 21 | |
| 183 | CH2CH2-(4-CF3-phenyl) | CH2CH3 | H | 255 | |
| 168 | CH2CH2-(4-CF3-phenyl) | CH3 | CH3 | 45 | |
| 183 | CH2CH2-(4-CF3-phenyl) | C2H5 | CH3 | 123 | |

TABLE 1-continued

Competitive Binding for D1 and D2 Receptors

[Structure: chromane scaffold with OH, H3C, S and R stereocenters, O, piperidine with N-R1, and CH2-N(R2)(R3) substituent]

| Example | R1 | R2 | R3 | D1 affinity Ki (nM) | D2 affinity Ki (nM) |
|---|---|---|---|---|---|
| 184 | 4-(CF3)-phenylethyl | (CH2)2CH3 | CH3 | 110 | |
| 185 | 4-(CF3)-phenylethyl | CH2CH=CH2 | CH2CH=CH2 | 3100 | |
| 186 | phenylethyl | CH2CH=CH2 | H | 1910 | |
| 187 | phenylethyl | CH2CH=CH2 | CH2CH=CH2 | 2640 | |
| 39 | 1-naphthylethyl | H | H | 113 | 10,000 |
| 40 | isobutyl (CH2CH(CH3)2 with extra CH3) — 2-methylbutyl | H | H | 361 | 10,000 |
| 41 | 2-methylpentyl | H | H | 114 | 10,000 |
| 42 | 2,2-dimethylbutyl | H | H | 398 | 10,000 |
| 43 | (CH2)3OH | H | H | 86.1 | 10,000 |
| 44 | isobutyl | H | H | 289 | 10,000 |
| 45 | 2-naphthylethyl | H | H | 96.4 | 10,000 |
| 46 | 4-phenoxyphenylethyl | H | H | 49 | 215 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 47 | 2-thienylethyl | H | H | 66.4 | 10,000 |
| 48 | 4-isopropylphenylethyl | H | H | 37.4 | 10,000 |
| 49 | 4-biphenylethyl | H | H | 48.2 | 310 |
| 50 | 2,4-difluorophenylethyl | H | H | 47.3 | 367 |
| 51 | 2-phenylpropyl | H | H | 156 | 5,000 |
| 52 | 2-(2-pyridyl)ethyl | H | H | 113 | 10,000 |
| 53 | 2-(3-pyridyl)ethyl | H | H | 60.7 | 10,000 |
| 54 | 2-(4-pyridyl)ethyl | H | H | 153 | 5,000 |
| 55 | 2-(2-quinolinyl)ethyl | H | H | 53.6 | 449 |
| 56 | 2-(3-quinolinyl)ethyl | H | H | 30.5 | 10,000 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 57 | 4-ethylquinoline | H | H | 59.6 | 10,000 |
| 58 | 4-chlorophenethyl | H | H | 52 | 5,000 |
| 59 | 2,4-dichlorophenethyl | H | H | 46.2 | 443 |
| 60 | 3,4-dichlorophenethyl | H | H | 11.8 | 364 |
| 61 | 4-methoxyphenethyl | H | H | 19.8 | 5,000 |
| 62 | 4-hydroxyphenethyl | H | H | 46.1 | 5,000 |
| 63 | 3,4-difluorophenethyl | H | H | 6.8 | 5,000 |
| 64 | 2-methylphenethyl | H | H | 198 | 576 |
| 65 | 3-methylphenethyl | H | H | 34 | 288 |
| 66 | 4-methylphenethyl | H | H | 75.7 | 5,000 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 67 | 3-ethylthiophene | H | H | 62.6 | 5,000 |
| 68 | 2-ethyl-methoxybenzene (MeO) | H | H | 96.7 | 232 |
| 69 | 3-fluoro-ethylbenzene | H | H | 32.5 | 5,000 |
| 70 | 2-fluoro-4-trifluoromethyl-ethylbenzene | H | H | 19.4 | 5,000 |
| 71 | 3-ethylfuran | H | H | 94.2 | 5,000 |
| 72 | 2-trifluoromethyl-ethylbenzene | H | H | 159 | 266 |
| 73 | 3-trifluoromethyl-ethylbenzene | H | H | 63.5 | 431 |
| 75 | 3,5-bis(trifluoromethyl)-ethylbenzene | H | H | 42 | 120 |

TABLE 1-continued
Competitive Binding for D1 and D2 Receptors
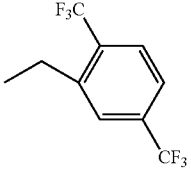
| Example | R1 | R2 | R3 | D1 affinity Ki (nM) | D2 affinity Ki (nM) |
|---|---|---|---|---|---|
| 76 | 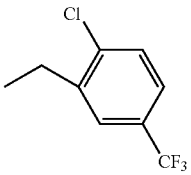 | H | H | 92 | 41 |
| 77 | 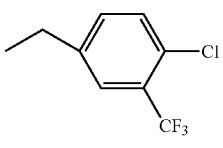 | H | H | 36 | 40 |
| 78 | 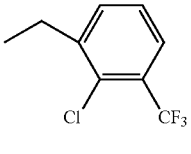 | H | H | 14 | 197 |
| 79 | 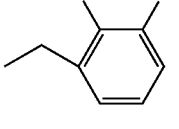 | H | H | 81 | 310 |
| 80 | 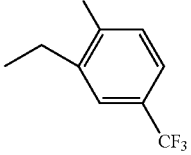 | H | H | 48.7 | 565 |
| 81 | 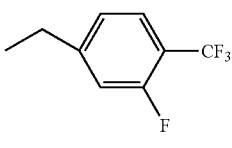 | H | H | 28.7 | 343 |
| 82 | 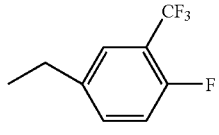 | H | H | 15.6 | 10,000 |
| 83 |  | H | H | 15.9 | 611 |

TABLE 1-continued

Competitive Binding for D1 and D2 Receptors

| Example | R1 | R2 | R3 | D1 affinity Ki (nM) | D2 affinity Ki (nM) |
|---|---|---|---|---|---|
| 84 | 3-fluoro-5-(trifluoromethyl)phenethyl | H | H | 33 | 450 |
| 85 | 2-(benzofuran-2-yl)ethyl | H | H | 25.6 | 389 |
| 86 | 2-(3-methylbenzothiophen-2-yl)ethyl | H | H | 39.9 | 97.6 |
| 87 | 2-(benzothiophen-3-yl)ethyl | H | H | 23.9 | 23.8 |
| 88 | 2-(1-methyl-1H-indol-2-yl)ethyl | H | H | 66.5 | 109 |
| 89 | 2-(1H-indol-3-yl)ethyl | H | H | 18.9 | 199 |
| 90 | 2-(1-methyl-1H-indol-3-yl)ethyl | H | H | 42.3 | 2.4 |

TABLE 1-continued
Competitive Binding for D1 and D2 Receptors
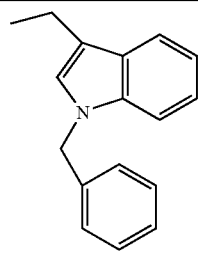
| Example | R1 | R2 | R3 | D1 affinity Ki (nM) | D2 affinity Ki (nM) |
|---|---|---|---|---|---|
| 91 | 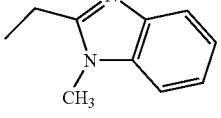 | H | H | 40.7 | 43.4 |
| 92 | 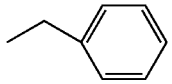 | H | H | 29.2 | 93.4 |
| 188 | 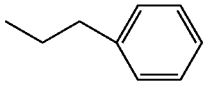 | $(CH_2)_2CH_3$ | $(CH_2)_2CH_3$ | 586 | 140 |
| 94 | 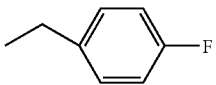 | $CH_3$ | H | 113 | 285 |
| 95 | 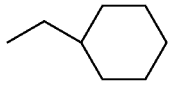 | $CH_3$ | H | 121 | 456 |
| 96 | 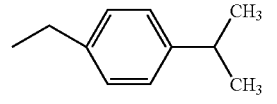 | $CH_3$ | H | 265 | 552 |
| 97 | 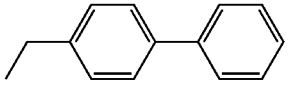 | $CH_3$ | H | 53.1 | 357 |
| 98 | 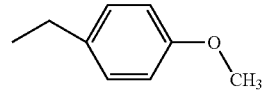 | $CH_3$ | H | 60.3 | 239 |
| 99 | 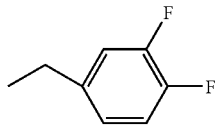 | $CH_3$ | H | 53.1 | 307 |
| 100 |  | $CH_3$ | H | 43.1 | ≧100,000 | ns
TABLE 1-continued
Competitive Binding for D1 and D2 Receptors
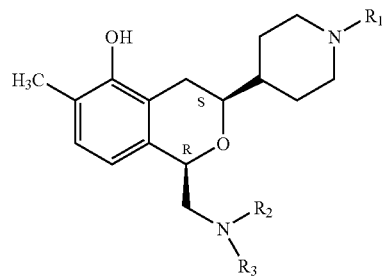
| Example | R1 | R2 | R3 | D1 affinity Ki (nM) | D2 affinity Ki (nM) |
|---|---|---|---|---|---|
| 101 | ethyl-phenyl-CH3 | CH3 | H | 92.2 | 322 |
| 191 | propyl-NH-C(=O)-phenyl ·HBr | H | H | 276 | 415 |
| 189 | propyl-NH-C(=O)-phenyl-F ·HBr | H | H | 312 | 61 |
| 190 | propyl-NH-C(=O)-phenyl-CH3 ·HBr | H | H | 46 | 361 |
| 192 | propyl-NH-C(=O)-NH-phenyl-F ·HBr | H | H | 77 | 477 |
| 193 | propyl-NH-C(=O)-NH-phenyl ·HBr | H | H | 50 | 284 |
| 13 | HN(CH(CH3)CH2CH3)-C(=O)-phenyl-Cl | H | H | 128 | 361 |

TABLE 1-continued
Competitive Binding for D1 and D2 Receptors
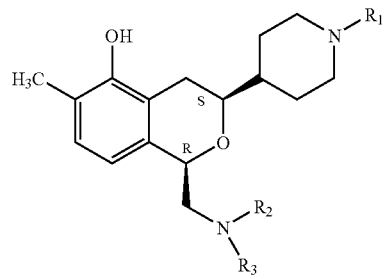
| Example | R1 | R2 | R3 | D1 affinity Ki (nM) | D2 affinity Ki (nM) |
|---------|----|----|----|---------------------|---------------------|
| 14 | *N-(pentan-3-yl with ethyl)-4-methylbenzamide group* | H | H | 274 | ≧100,000 |
| 15 | *N-(butan-2-yl)-4-methylbenzamide group* | H | H | 126 | 523 |
| 16 | *N-(pentan-2-yl)-4-trifluoromethylbenzamide group* | H | H | 149 | 379 |
| 17 | *N-(pentan-2-yl)-2,4-dichlorobenzamide group* | H | H | 138 | ≧100,000 |
| 18 | *N-(pentan-2-yl)-4-biphenylcarboxamide group* | H | H | 244 | 389 |
| 19 | *N-(pentan-2-yl)-2-naphthamide group* | H | H | 158 | 310 |

TABLE 1-continued

Competitive Binding for D1 and D2 Receptors

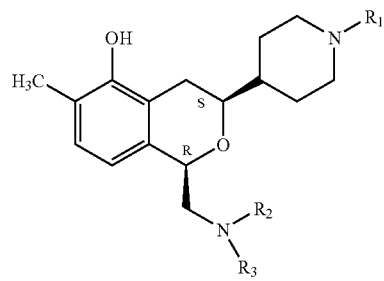

| Example | R1 | R2 | R3 | D1 affinity Ki (nM) | D2 affinity Ki (nM) |
|---|---|---|---|---|---|
| 20 | N-sec-butyl benzo[b]thiophene-2-carboxamide group | H | H | 52.4 | 265 |
| 21 | N-sec-butyl benzamide group | H | H | 120 | ≧100,000 |
| 22 | N-sec-butyl 4-fluorobenzamide group | H | H | 114 | 564 |
| 23 | N-sec-butyl 4-bromobenzamide group | H | H | 91.8 | 526 |
| 24 | N-sec-butyl 4-nitrobenzamide group | H | H | 240 | 638 |
| 25 | N-sec-butyl thiophene-2-carboxamide group | H | H | 56.1 | 218 |
| 195 | 2-phenylpropanoic acid group | H | H | 1700 | |

D1 Activation Adenylyl Cyclase Assay

Purpose: To measure D1-agonist activity compounds using an Adenylyl Cyclase Activation Flash Plate Assay from NEN.
Buffers: Activation and Detection buffers are provided from NEN: Catalog # SMP004A.
Procedure:
Maintenance of D1 transfected CHO cell line:
1. Cells are grown in a 150 cc flask in an incubator at 37° C. with 5% $CO_2$ for 2-3 days (4 maximum) until confluent.
2. Aspirate off old media (Cells adhere to the plastic flask), wash 2× with sterile PBS.
3. Add ~5 mL of Trypsin EDTA (enough to cover bottom of the flask) for 5 min. at RT.
4. Stop digestion with 15 mL of Media (Ham's F12 plus 10% FBS, 1% P/S, 400 µg/mL G418).
Bang flask on counter to release them from the flask.
5. Add 2 mL of this to 30 mL of Media in a fresh flask. Return to incubator.

Preparation of Cells for Assay:
1. Loosen the cells with 5 mL Vercine (EDTA)/flask for 10 minutes in incubator.
2. Add 20 mL of Serum-free media/flask. Transfer to 50-mL Falcon tube.
3. Spin down cells at 1000 RPM for 5 minutes at 4° C.
4. Aspirate off old media and resuspend in 5 mL of Serum-free media/plate to be done.
5. Dilute 10 µL 1/10 in 90 µL Trypan Blue solution and count with a hemocytometer.
Count (live cells only) all four areas and average them.
Count X $10^5$ equals cells/mL (including accounting for dilution in Trypan).
6. Dilute to 50,000 cells/50 µL (1,000,000 cells/mL) in Serum-free media.
7. Put 50 µL/well in Rows 3-12 of a cAMP FlashPlate.
8. Put in incubator at 37° C. for 2-4 hours, to allow cells to recover and attach.

Adenylyl Cyclase Activation Assay:
1. Prepare the cAMP standards:
Add 130 µL/well of stimulation buffer to each row of a separate 96-well "standard" plate, 2 columns/plate.
Dilute stock cAMP standard 1/5 with stimulation buffer (final concentration is 1000 pmol/mL). Add 130 µL of this to row A.
Make 1/2 serial dilutions by adding 130 µL from each well to the next (A-G), mixing between each.
Final concentrations are:
A: 500, B: 250, C: 125, D: 62.5, E: 31.25, F: 15.6, G: 7.8, H: 0 pmol/mL.
Place 100 µL from each row from 2 columns of the standard plate into columns 1 and 2 of each "reaction" plate.
2. Prepare the negative and positive control in the "reaction" plate:
Column 3, rows A-D, add 100 µL stimulation buffer (negative control).
Column 3, rows E-H, add 90 µL of stimulation buffer plus 10 µL of 200 µM APO (positive control, 10 µM final). (10 µL 10 mM APO, plus 490 µL stim. buffer=1/50 dilution.)
3. Prepare the agonist compound dilutions in the "compound" plate:
Add 80 µL of stimulation buffer to row A (One column for each compound), and 90 µL of stimulation buffer to rows B—H.
Add 20 µL of 10 mM of each compound to appropriate row A.
Make 1/10 serial dilutions by adding 10 µL from each well to the next (A-H), mixing between each.
4. Add inhibitors to the Reaction plate in triplicate:
Add 90 µL of stimulation buffer to each row (columns 4-12).
Transfer 10 µL from each inhibitor in "compound" plate to the "reaction" plate, as follows:
Plate 1: Compound 1, Columns 4-6, Compound 2, Columns 7-9, Compound 3, Columns 10-12.
Plate 2: Compound 4, Columns 4-6, Compound 5, Columns 7-9, Compound 6, Columns 10-12.
Plate 3: Compound 7, Columns 4-6, Compound 8, Columns 7-9, Compound 9, Columns 10-12.
Plate 4: Compound 10, Columns 4-6, Compound 11, Columns 7-9, Compound 12, Columns 10-12
Plate 5: Compound 13, Columns 4-6, Compound 14, Columns 7-9, Compound 15, Columns 10-12.
Plate 6: Compound 16, Columns 4-6, Compound 17, Columns 7-9, Compound 18, Columns 10-12.
Final concentrations (once it is added to the cells) are:
A: 100 µM, B: 10 µM, C: 1 µM, D: 100 nM, E: 10 nM, F: 1 nM, G: 100 pM, H: 10 pM.
5. Prepare Detection/Stop buffer by adding 90 µL/plate of cAMP-$^{125}$I to 10 mL/plate plus 6 mL (for dead volume) of detection buffer.
Steps 6-8 performed with the Multi-Mek.
6. Add 50 µL to each well of the FlashPlate with CHO cells set up earlier.
7. Incubate at RT for 8 minutes.
8. Stop reaction by adding 100 µL of detection/stop buffer to each well.
9. Cover with plastic film and incubate at RT for 16-24 hours (don't wait more than 24 hours).
10. Count in a Packard Top-Count.

Calculations:
1. Raw signals generated by cAMP standard wells, without cells, are averaged at each cAMP concentration and converted to % $B/B_o$ by dividing the raw signal at each cAMP concentration by the raw signal with no cAMP added.
2. These values are used to generate a standard curve by plotting cAMP concentration versus % $B/B_o$.
3. Raw data for each compound at each concentration is also converted to % B/B. by the same method.
4. These values are then converted to pmol cAMP/mL using the standard curve.
5. These cAMP values are then averaged across the three replicates for each compound concentration.
6. This value is then take as a percentage between the basal stimulated cells (cells alone), and stimulated cells (cells with a saturating amount of a known D1 agonist.) This generates a percent stimulation for each compound at each concentration.
7. This data is plotted as compound concentration versus percent stimulation, and a line is fit to the data points.
8. The concentration at which half-maximal stimulation occurs is reported as the $EC_{50}$.

The percent stimulation at which the curve plateaus is compared to the maximum stimulation of the natural agonist Dopamine, and reported as the % Maximal Dopamine stimulation.

Table 2 describes the intrinsic activity in the adenylate cyclase assay, indicating the compounds act as agonists at the $D_1$ receptor.

TABLE 2

Agonist Activity at the D₁ Receptor

| Example | R1 | R2 | R3 | D₁ EC₅₀ (nM) | D₁ max Ki (nM) |
|---|---|---|---|---|---|
| 111 | —(CO)OC(CH₃)₂ | H | H | 49 | 51 |
| 112 | —(CO)OCH₃ | H | H | 0.6 | 42 |
| 113 | —(CO)O-phenyl | H | H | 4.2 | 46 |
| 114 | —(CO)O-(4-methylphenyl) | H | H | 0.85 | 30 |
| 115 | —(CO)O-(4-chlorophenyl) | H | H | 48 | 63 |
| 116 | —(CO)O-(2-chlorophenyl) | H | H | 4.6 | 79 |
| 117 | —(CO)O-(4-bromophenyl) | H | H | 4.3 | 66 |
| 118 | —(CO)O-(4-fluorophenyl) | H | H | 8.5 | 66 |
| 119 | —(CO)O-(2-trifluoromethylphenyl) | H | H | 3.1 | 79 |
| 120 | —(CO)O-(4-methoxyphenyl) | H | H | 36 | 93 |
| 121 | —(CO)O-(2-hydroxyphenyl) | H | H | 2.5 | 64 |

TABLE 2-continued

Agonist Activity at the D₁ Receptor

| Example | R1 | R2 | R3 | D₁ EC₅₀ (nM) | D₁ max Ki (nM) |
|---|---|---|---|---|---|
| 123 | 2-naphthyl acetate | H | H | 10 | 53 |
| 124 | N-(2-fluoro-5-trifluoromethylphenyl)acetamide | H | H | 20 | 40 |
| 125 | N-(3-methoxyphenyl)acetamide | H | H | 60 | 42 |
| 126 | N-(3-hydroxyphenyl)acetamide | H | H | 1.7 | 19 |
| 128 | N-(4-fluorophenyl)acetamide | H | H | 6,000 | 85 |
| 129 | N-(2-fluorophenyl)acetamide | H | H | 2,000 | 66 |
| 131 | N-methyl-N-phenylacetamide | H | H | 6.4 | 18 |
| 135 | 1-(pyrrolidin-1-yl)ethanone | H | H | 2.8 | 50 |
| 139 | N,N-dibutylacetamide [(CH₂)₃CH₃] | H | H | 0.11 | 23 |

TABLE 2-continued

Agonist Activity at the D₁ Receptor

| Example | R1 | R2 | R3 | D₁ EC₅₀ (nM) | D₁ max Ki (nM) |
|---|---|---|---|---|---|
| 140 | N-acetyl-N,N-di(propenyl) group | H | H | 9 | 32 |
| 142 | —SO₂—CH₂—phenyl | H | H | 1.9 | 42 |
| 144 | —SO₂—(2,3-dimethoxyphenyl) | H | H | 3.6 | 76 |
| 146 | —SO₂—(4-tert-butylphenyl) | H | H | 79 | 87 |
| 147 | —SO₂—(2-naphthyl) | H | H | 394 | 100 |
| 150 | —SO₂—(3,4-dichlorophenyl) | H | H | 256 | |
| 151 | —SO₂—(2,5-dichlorophenyl) | H | H | 58 | 64 |
| 157 | —SO₂—CH₂—CF₃ (2,2,2-trifluoroethyl) | H | H | 460 | 74 |
| 158 | —SO₂—CH₂—(2-nitrophenyl) | H | H | 11 | 31 |

TABLE 2-continued

Agonist Activity at the $D_1$ Receptor

| Example | R1 | R2 | R3 | $D_1$ EC$_{50}$ (nM) | $D_1$ max Ki (nM) |
|---|---|---|---|---|---|
| 159 | —SO$_2$CH$_2$CH$_2$-(1-naphthyl) | H | H | 35 | 44 |
| 161 | —SO$_2$CH(phenyl)$_2$ | H | H | 40 | 50 |
|  | —CH$_3$ | —CH$_3$ | H | 1500 | 40 |
| 167 | —SO$_2$-(1,2,3,4-tetrahydroisoquinolin-2-yl) | H | H | 77 | 62 |
| 106 | —CH$_2$CH$_2$CH$_2$-phenyl | H | H | 29 | 45 |
| 107 | —CH$_2$CH$_2$CH$_2$-(3-chlorophenyl) | H | H | 140 | 42 |
| 108 | —CH$_2$CH$_2$CH$_2$CH$_2$CH(4-F-phenyl)$_2$ | H | H | 36 |  |
| 27 | —CH$_2$CH$_2$CH(CH$_3$)-phenyl | H | H | 280 | 49 |

TABLE 2-continued
Agonist Activity at the D₁ Receptor
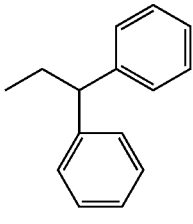
| Example | R1 | R2 | R3 | $D_1$ $EC_{50}$ (nM) | $D_1$ max Ki (nM) |
|---|---|---|---|---|---|
| 28 | 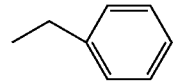 | H | H | 131 | 54 |
| 93 | 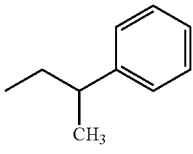 | H | H | 45 | 34 |
| 29 | 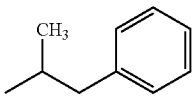 | H | H | 40 | 50 |
| 30 | 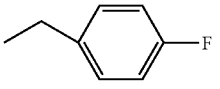 | H | H | 60 | 49 |
| 26 | 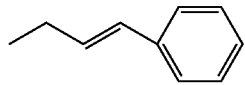 | H | H | 11 | 56 |
| 105 | 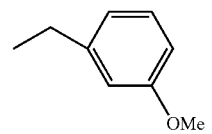 | H | H | 102 | 69 |
| 31 | 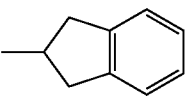 | H | H | 13 | 47 |
| 32 | 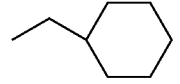 | H | H | 12 | 32 |
| 33 | —(CH₂)₃CH₃ | H | H | 13 | 44 |
| 34 |  | H | H | 66 | 33 |

TABLE 2-continued

Agonist Activity at the $D_1$ Receptor

| Example | R1 | R2 | R3 | $D_1$ $EC_{50}$ (nM) | $D_1$ max Ki (nM) |
|---|---|---|---|---|---|
| 35 | 2-Cl-phenethyl | H | H | 44 | 30 |
| 36 | 2-F-phenethyl | H | H | 62 | 51 |
| 37 | 3-Cl-phenethyl | H | H | 110 | 53 |
| 105 | 3-(2-methylbutyl)-6-fluoro-benzisoxazole | H | H | 100 | 63 |
| 104 | 3-(2-pentyl)-6-fluoro-benzisoxazole | H | H | 116 | 84 |
| 38 | cyclopropylmethyl | H | H | 10 | 31 |
| 194 | 3-pentyl-phenyl | $CH_3$ | H | 34 | 56 |
| 110 | 3-phenylpropyl-CH_2 | H | H | 6 | 58 |
| 177 | phenethyl | c-$C_4H_7$ | H | 10,000 | 305 |
| 178 | phenethyl | —$(CH_2)_4$— | | 10,000 | 181 |

TABLE 2-continued
Agonist Activity at the $D_1$ Receptor
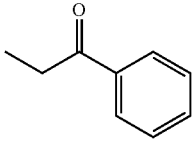
| Example | R1 | R2 | R3 | $D_1$ $EC_{50}$ (nM) | $D_1$ max Ki (nM) |
|---|---|---|---|---|---|
| 179 | 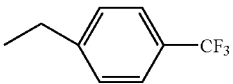 | $C_2H_5$ | H | 810 | 60 |
| 181 | 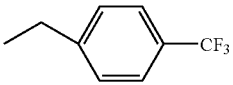 | H | H | 6 | 66 |
| 182 | 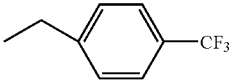 | $CH_3$ | H | 220 | 50 |
| 183 | 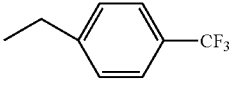 | $CH_2CH_3$ | H | 1300 | 60 |
| 168 | 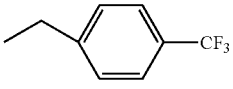 | $CH_3$ | $CH_3$ | 31000 | 95 |
| 183 | 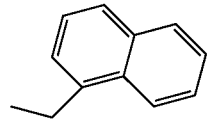 | $C_2H_5$ | $CH_3$ | 7000 | 57 |
| 39 | 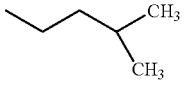 | H | H | 750 | 39 |
| 41 | 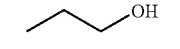 | H | H | 250 | 32 |
| 43 | 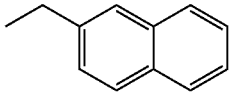 | H | H | 110 | 45 |
| 45 | 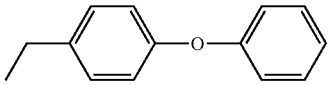 | H | H | 110 | 36 |
| 46 | 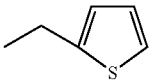 | H | H | 100 | 74 |
| 47 |  | H | H | 170 | 39 |

TABLE 2-continued
Agonist Activity at the D₁ Receptor
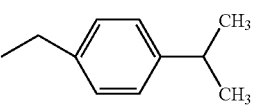
| Example | R1 | R2 | R3 | D₁ EC₅₀ (nM) | D₁ max Ki (nM) |
|---|---|---|---|---|---|
| 48 | 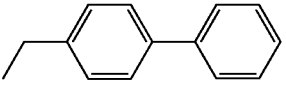 | H | H | 26 | 50 |
| 49 | 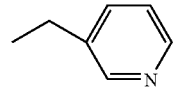 | H | H | 78 | 92 |
| 53 | 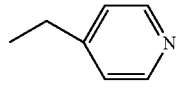 | H | H | 15 | 45 |
| 54 | 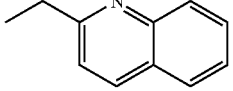 | H | H | 45 | 49 |
| 55 | 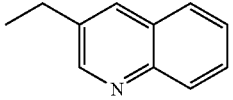 | H | H | 16 | 35 |
| 56 | 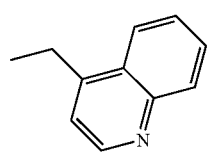 | H | H | 12 | 60 |
| 57 | 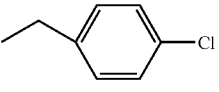 | H | H | 12 | 46 |
| 58 | 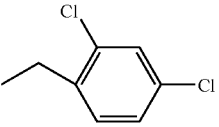 | H | H | 10 | 46 |
| 59 | 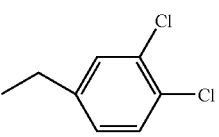 | H | H | 12 | 32 |
| 60 |  | H | H | 160 | 77 |

TABLE 2-continued
Agonist Activity at the D₁ Receptor
| Example | R1 | R2 | R3 | D₁ EC₅₀ (nM) | D₁ max Ki (nM) |
|---|---|---|---|---|---|
| 61 | 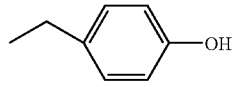 | H | H | 47 | 45 |
| 62 | 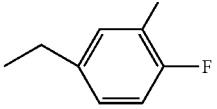 | H | H | 14 | 25 |
| 63 | 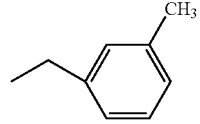 | H | H | 9 | 58 |
| 65 | 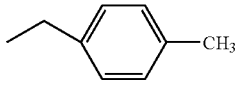 | H | H | 11 | 43 |
| 66 | 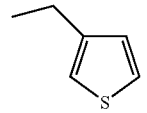 | H | H | 6 | 44 |
| 67 | 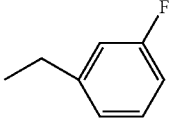 | H | H | 9 | 33 |
| 69 | 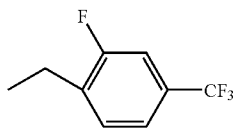 | H | H | 10 | 34 |
| 70 | 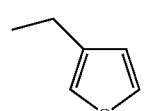 | H | H | 77 | 62 |
| 71 | 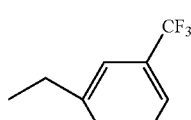 | H | H | 420 | 88 |
| 73 |  | H | H | 15 | 54 |

TABLE 2-continued
Agonist Activity at the $D_1$ Receptor
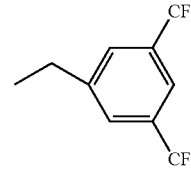
| Example | R1 | R2 | R3 | $D_1$ $EC_{50}$ (nM) | $D_1$ max Ki (nM) |
|---|---|---|---|---|---|
| 75 | 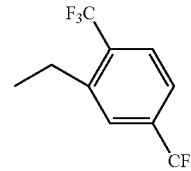 | H | H | 220 | 70 |
| 76 | 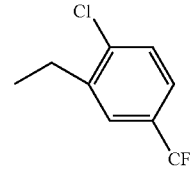 | H | H | 580 | 77 |
| 77 | 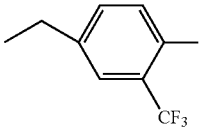 | H | H | 80 | 62 |
| 78 | 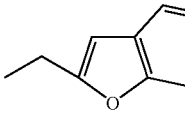 | H | H | 2 | 51 |
| 85 | 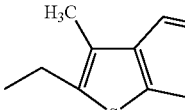 | H | H | 16 | 74 |
| 86 | 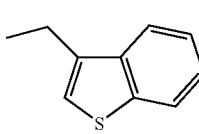 | H | H | 77 | 50 |
| 87 | 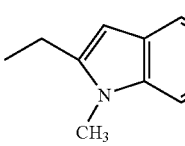 | H | H | 27 | 37 |
| 88 |  | H | H | 29 | 48 |

TABLE 2-continued
Agonist Activity at the D₁ Receptor
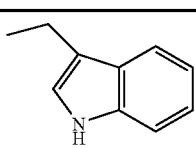
| Example | R1 | R2 | R3 | D₁ EC₅₀ (nM) | D₁ max Ki (nM) |
|---|---|---|---|---|---|
| 89 | 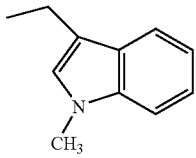 | H | H | 8 | 38 |
| 90 | 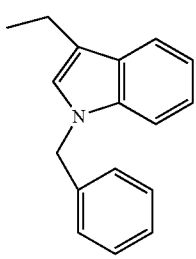 | H | H | 9 | 46 |
| 91 | 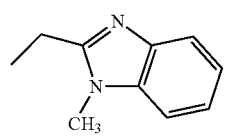 | H | H | 12 | 63 |
| 92 | 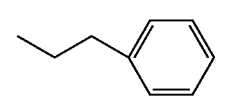 | H | H | 0.98 | 61 |
| 94 | 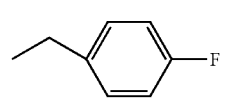 | CH₃ | H | 35 | 59 |
| 95 | 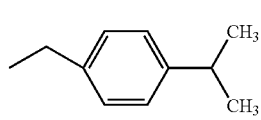 | CH₃ | H | 250 | 63 |
| 97 | 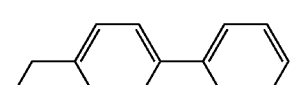 | CH₃ | H | 66 | 30 |
| 98 | 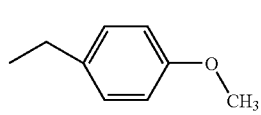 | CH₃ | H | 15 | 29 |
| 99 |  | CH₃ | H | 22 | 54 |

TABLE 2-continued
Agonist Activity at the D₁ Receptor
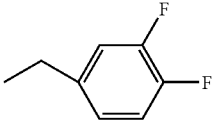
| Example | R1 | R2 | R3 | D₁ EC₅₀ (nM) | D₁ max Ki (nM) |
|---|---|---|---|---|---|
| 100 |  | CH₃ | H | 60 | 27 |
| 101 | 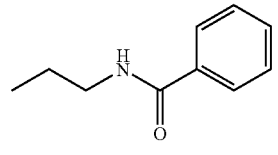 | CH₃ | H | 33 | 62 |
| 191 | 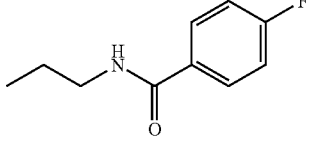 | H | H | 180 | 51 |
| 189 | 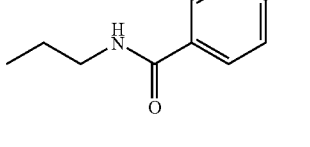 | H | H | 270 | 26 |
| 190 | 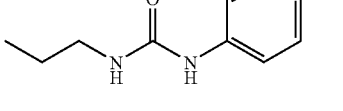 | H | H | 11 | 42 |
| 192 | 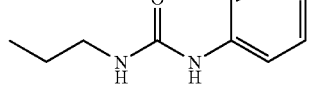 | H | H | 11 | |
| 193 | 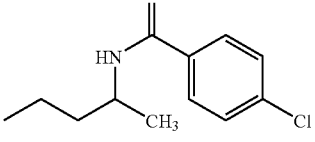 | H | H | 43 | 42 |
| 13 |  | H | H | 30 | 86 |

TABLE 2-continued

Agonist Activity at the $D_1$ Receptor

| Example | R1 | R2 | R3 | $D_1$ $EC_{50}$ (nM) | $D_1$ max Ki (nM) |
|---|---|---|---|---|---|
| 15 | N-(pentan-2-yl) 4-methylbenzamide | H | H | 11 | 35 |
| 16 | N-(pentan-2-yl) 4-(trifluoromethyl)benzamide | H | H | 56 | 41 |
| 17 | N-(pentan-2-yl) 2,4-dichlorobenzamide | H | H | 18 | 36 |
| 19 | N-(pentan-2-yl) 2-naphthamide | H | H | 6.1 | 35.6 |
| 20 | N-(pentan-2-yl) benzothiophene-2-carboxamide | H | H | 61 | 46 |
| 21 | N-(pentan-2-yl) benzamide | H | H | 14 | 50 |
| 22 | N-(pentan-2-yl) 4-fluorobenzamide | H | H | 24 | 39 |

TABLE 2-continued

Agonist Activity at the $D_1$ Receptor

| Example | R1 | R2 | R3 | $D_1$ $EC_{50}$ (nM) | $D_1$ max Ki (nM) |
|---|---|---|---|---|---|
| 23 | 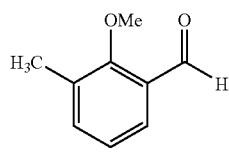 | H | H | 59 | 47 |
| 25 | 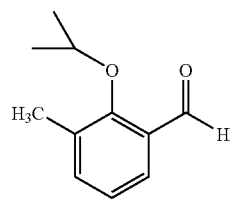 | H | H | 54 | 68 |

SYNTHETIC EXAMPLES

General Procedures

For High Performance Liquid Chromatography (HPLC) use the following conditions: Synergi 2u Hydro-RP 20×4.0 mm column, Gradient: 5% B to 90% B in 3 min. to 100% B in 2 min. 1 ml/min flow; A=0.1% formic acid in water, B=0.1% formic acid in acetonitrile.

For general SCX column purifications: Load the sample on a methanol pretreated SCX column and wash with methanol. Elute the product with 2N $NH_3$ in methanol.

Aldehydes and ketones used in the synthetic methods described below that were commercially available except where noted. Aldehydes for Examples 14-25 were synthesized according to the procedure described in Marson C. and Fallah, H., Chem. Commun. 83-84 (1998).

Example 1

2-Methoxy-3-methylbenzaldehyde

Scheme A, Starting Material

Dissolve 2-hydroxy-3-methylbenzaldehyde (80 g, 0.588 mol) in 350 mL DMF and warm at 50°. Add potassium carbonate (97.4 g, 0.705 mol), follow it by the dropwise addition of iodomethane (125 g, 0.881 mol). After one hour at 50° C. the reaction mixture was allow to cool to room temperature and add 700 mL of water. Adjust the pH to 7 with 3N HCl and then extract the mixture two times with 350 mL of ethyl acetate. Wash the combined organic layers with brine and dry ($Na_2SO_4$).

Remove the solvent to give 87.9 g (99.9%) of 2-methoxy-3-methylbenzaldehyde: $^1$H NMR (DMSO-d6) δ 10.25 (s, 1H), 7.60 (m, 1H), 7.20 (m, 1H), 3.85 (s, 3H), 2.28 (s, 3H).

Example 2

3-Methyl-2-isopropoxybenzaldehyde

Scheme A, Starting Material

Stir a mixture of 3-methylsalicylaldehyde (100 g, 0.73 mol), isopropyl iodide (187 g, 1.1 mol) and $K_2CO_3$ (141 g, 1.0 mol) in DMF (400 mL) for 20 hr at room temperature. TLC shows partial reaction; thus, add more isopropyl iodide (43 g, 0.25 mol) and heat the reaction to 45° C. with stirring for an additional 10 hr. Dilute the reaction mixture with $H_2O$ (1 L) and extract the resulting mixture with EtOAc. Wash the organic layer with 0.25 M. aqueous NaOH and then with $H_2O$. Dry over $MgSO_4$ and evaporate the solvent to give 3-methyl-2-isopropoxybenzaldehyde, 122 g (94%); ¹H-NMR (CDCl₃) δ 7.7-7.1 (m, 3H), 4.2 (m, 1H), 2.3 (s, 3H), 1.4 (d, 6H).

Example 3

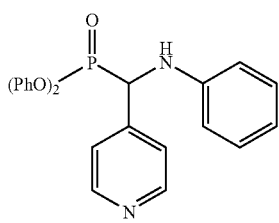

[(Phenylamino)-4-pyridinylmethyl]phosphonic acid diphenyl ester

Scheme A, Starting Material

Treat a solution of 4-pyridinecarboxyaldehyde (16.8 g, 0.16 mol) in TBME (225 mL) and IPA (75 mL) with aniline (17.6 g, 0.19 mol) and diphenyl phosphite (58.8 g, 0.25 mol). Stir the solution for 3 hr at room temperature during which time the product crystallizes from the solution. Store the mixture at 4° C. for 15 hr and then collect the solid that forms and wash with cold IPA and heptane to give [(phenylamino)-4-pyridinylmethyl]phosphonic acid diphenyl ester, 59 g (91%); ¹H-NMR (CDCl₃) δ 8.6-6.6 (m, 19H), 5.1 (m, 1H), 5.0 (m, 1H).

Example 4

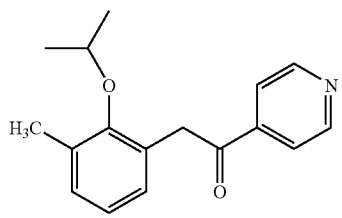

2-(2-isopropoxy-3-methylphenyl)-1-(4-pyridinyl)ethanone

Scheme A, Step A1

Combine [(phenylamino)-4-pyridinylmethyl]phosphonic acid diphenyl ester (29.4 g, 0.071 mol), 3-methyl-2-isopropoxybenzaldehyde (13.0 g, 0.073 mol) and Cs₂CO₃ (29.9 g, 0.092 mol) in THF (225 mL) and IPA (75 mL). Stir the mixture under nitrogen for 48 hr before adding to 3M aqueous HCl under nitrogen. Allowed the red solution to stand for 3 hr during which time the red color fades to yellow. Cool the solution was to 10° before neutralizing to pH 12 by the slow addition of 50% aqueous NaOH. Extract the mixture with EtOAc and then wash the organic layer with H₂O. Dry over MgSO₄, and evaporate the solvent to give a residue. Purify the residue by chromatography over SiO₂ using EtOAc:heptane (1:1). Receive fractions containing pure product and some fractions containing a mixture of product and the aniline Schiff's base of the product. Dissolve the latter mixture in 3M aqueous HCl and allow to stand for 6 hr, at which time the red color discharges. Neutralize the acid solution with NaHCO₃ and extract with EtOAc, wash the extract with H₂O and dry over MgSO₄. Evaporate the solvent to obtain 4.6 g of 2-(2-isopropoxy-3-methylphenyl)-1-(4-pyridinyl)ethanone which when blended with the pure product from the column gives a total yield of 16.9 g (89%); ¹H-NMR (CDCl₃) δ 8.8-6.9 (m, 7H), 4.3 (s, 2H), 4.2 (m, 1H), 2.3 (s, 3H), 1.3 (d, 6H).

Example 5

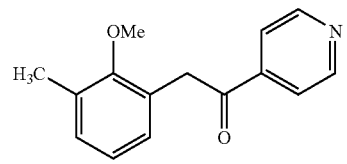

2-(2-Methoxy-3-methylphenyl)-1-(4-pyridinyl)ethanone

Scheme A, Step A1

Prepare in analogous fashion as above starting from 2-methoxy-3-methylbenzaldehyde; ¹H-NMR (CDCl₃) δ 8.8 (d, 2H), 7.8 (d, 2H), 7.1-7.0 (m, 3H), 4.3 (s, 2H), 3.7 (s, 3H), 2.3 (s, 3H).

Example 6

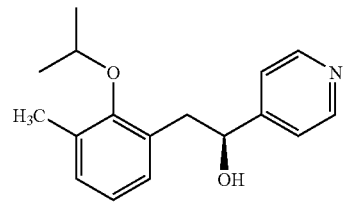

(S)-2-(2-Isopropoxy-3-methylphenyl)-1-(4-pyridinyl)ethanol

Scheme A, Step A2

Under nitrogen, at −30° C. slowly add BF₃·Et₂O (1.7 g, 12 mmol) to a solution of (−)-B-chlorodiisopinocampheylborane (6.1 g, 19 mmol) in THF (40 mL). Cool the solution to −40° and add 2-(2-isopropoxy-3-methylphenyl)-1-(4-pyridinyl)ethanone (3.2 g, 12 mmol). Allow the solution to slowly come to room temperature and stir for 15 hr. Add MeOH and 3M aqueous HCl to the reaction mixture and stir for an additional 45 min. Evaporate the solvent and dissolve the residue in 3M aqueous HCl and wash with heptane. Neutralize the aqueous fraction with 50% aqueous NaOH to pH 12 and extract with EtOAc. Wash the organic phase was with brine and dry over MgSO₄. Evaporate the solvent to afford a yellow oil. Purify the oil by chromatography over SiO₂ using EtOAc: heptane (1:1). Evaporate the product-containing fraction to give (S)-2-(2-isopropoxy-3-methylphenyl)-1-(4-pyridinyl)

ethanol as an oil, 1.16 g (36%); $^1$H-NMR (CDCl$_3$) δ 8.5-6.8 (m, 7H), 4.9 (m, 1H), 4.3 (m, 1H), 3.1-2.9 (m, 2H), 2.3 (s, 3H), 1.3 (d, 6H).

Example 7

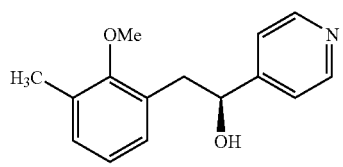

(S)-2-(2-Methoxy-3-methylphenyl)-1-(4-pyridinyl)ethanol

Scheme A, Step A2

Prepare in analogous fashion to above Example from 2-(2-methoxy-3-methylphenyl)-1-(4-pyridinyl)ethanone; $^1$H-NMR (DMSO-d$_6$) δ 8.5 (d, 2H), 7.3 (d, 2H), 7.1-6.9 (m, 3H), 5.5 (d, 1H), 4.9 (m, 1H), 3.7 (s, 3H), 3.3 (s, 1H), 2.9 (d, 2H), 2.2 (s, 3H).

Example 8

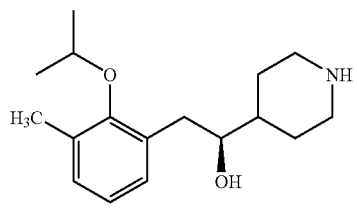

(S)-2-(2-Isopropoxy-3-methylphenyl)-1-(4-piperidinyl)ethanol

Scheme A, Step A3

Shake a mixture of (S)-2-(2-isopropoxy-3-methylphenyl)-1-(4-pyridinyl)ethanol (21.1 g, 78 mmol), HOAc (400 mL) and PtO$_2$ (370 mg) with H$_2$ (50 psi) for 15 hr. Filter the mixture through celite and evaporate the solvent to give (S)-2-(2-isopropoxy-3-methylphenyl)-1-(4-piperidinyl)ethanol as the acetate salt; $^1$H-NMR (CDCl$_3$) δ 7.1-6.9 (m, 2H), 4.2 (m, 1H), 3.6 (m, 1H), 3.4 (m, 2H), 2.9-2.7 (m, 4H), 2.3 (s, 3H), 2.0 (s, 3H), 2.1-1.5 (m, 5H), 1.3 (d, 6H).

Example 9

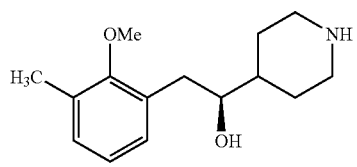

(S)-2-(2-Methoxy-3-methylphenyl)-1-(4-piperidinyl)ethanol

Scheme A, Step A3

Prepare in an analogous fashion from (S)-2-(2-methoxy-3-methylphenyl)-1-(4-pyridinyl)ethanol, $^1$H-NMR (DMSO-d$_6$) δ 8.3 (broad s, 2H), 7.1-6.9 (m, 3H), 5.8 (s, 1H), 3.7 (s, 3H), 3.5 (m, 1H), 3.2 (m, 2H), 2.7 (m, 2H), 2.5 (m, 2H), 2.2 (s, 3H), 1.8 (s, 3H), 1.7-1.5 (m, 4H).

Example 10

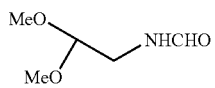

N-(2,2,-dimethoxyethyl)formamide

Scheme A, Starting Material for Step A4

Heat at reflux for 2.5 hr Aminoacetaldehyde dimethylacetal (200 g, 1.9 mol) and ethyl formate (172 mL). Cool, and remove excess ethanol and ethyl formate were at 40-70° C./7 torr. Distill the residue in Kugelrohr apparatus to give 212.1 g (83.7%) of product; $^1$H-NMR (CDCl$_3$) δ 8.2, 8.0 (s, d, 1H), 6.1 (broad s, 1H), 4.4, 4.3 (2×m, 1H), 3.4, 3.3 (2×m, 2H), 3.4 (2×s, 6H).

Example 11

N-((1R,3S)-5-Isopropoxy-6-methyl-3-(4-piperidinyl)-1-isochromanylmethyl)formamide Scheme A, Step A4

Dissolve (S)-2-(2-Isopropoxy-3-methylphenyl)-1-(4-piperidinyl)ethanol (21.5 g, 78 mmol), N-(2,2,-dimethoxyethyl)formamide (15.5 g, 117 mmol) and BF$_3$·Et$_2$O (66.1 g, 466 mmol) in CH$_2$Cl$_2$ (350 mL). Heat the solution to reflux for 3 hr and then allow to stand 15 hr at room temperature. Evaporate the solvent and dissolve the residue in CH$_2$Cl$_2$. Treat the resulting solution with 50% aqueous NaOH to obtain a pH of 13. Separate the phases and extract the aqueous phase with CH$_2$Cl$_2$. Combine the organic phases, wash with brine and dry over MgSO$_4$. Evaporate the solvent to afford a residue. Purify the residue by chromatography over SiO$_2$ using CHCl$_3$:2M NH$_3$/MeOH (8:2). Evaporate the product-containing fractions and triturate with 1:1 Et$_2$O:heptane to afford a crystalline solid; $^1$H-NMR (CDCl$_3$) δ 8.2, 7.9 (2s, 1H), 7.0-6.7 (m, 2H), 6.2 (m, 1H), 4.8 (m, 1H). 4.2 (m, 1H), 4.1 (m, 1H), 3.3 (m, 2H), 3.2 (m, 2H), 2.9 (m, 1H), 2.7, (m, 2H), 2.5 (m, 2H), 2.2 (s, 3H), 2.0-1.4 (m, 5H), 1.3-1.2 (2d, 6H).

Example 12

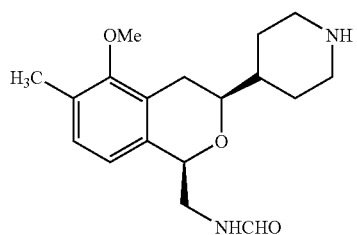

N-((1R,3S)-5-methoxy-6-methyl-3-(4-piperidinyl)-1-isochromanylmethyl)formamide

Scheme A, Step A4

Prepare in an analogous fashion from (S)-2-(2-Methoxy-3-methylphenyl)-1-4-piperidinyl)ethanol, $^1$H-NMR (CDCl$_3$) δ 8.2, 8.0 (s and d, 1H), 7.0 (d, 1H), 6.9 (d, 1H), 4.8 (m, 1H), 4.2 (m, 1H), 3.7, (s, 3H), 3.4 (m, 2H), 3.1 (m, 2H), 2.9 (m, 2H), 2.7 (m, 1H), 2.5 (m, 1H), 2.2 (s, 3H), 2.2-1.8 (m, 5H).

Example 13

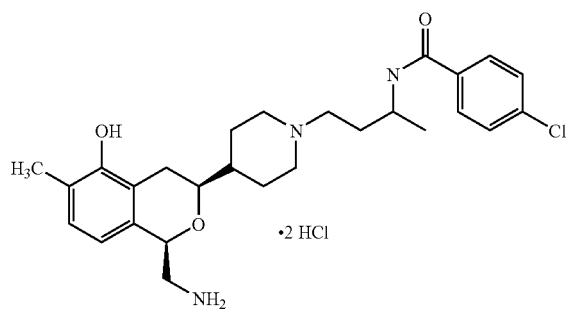

N-{3-[4-((1R,3S)-1-Aminomethyl-5-hydroxy-6-methyl-isochroman-3-yl)-piperidin-1-yl]-1-methyl-propyl}-4-chloro-benzamide dihydrochloride Scheme B, Step B1 4-Chloro-N-{3-[4-((1R,3S)1-formylaminomethyl-5-methoxy-6-methyl-isochroman-3-yl)-piperidin-1-yl]-1-methylpropyl}-benzamide Stir a suspension of N-((1R,3S)-5-methoxy-6-methyl-3-(4-piperidinyl)-1-isochromanylmethyl)formamide (1.0 mmol) with 4-Chloro-N-(1-methyl-3-oxo-propyl)-benzamide (3.0 mmol) and sodium triacetoxyborohydride (3.0 mmol) in dichloromethane (5 mL) at room temperature overnight. Apply the reaction mixture directly to a 5 g SCX column and elute and concentrate the appropriate fractions to obtain the title compound. Use the compound directly for the next step.

Scheme B, Step B2 N-{3-[4-((1R,3S)-1-Aminomethyl-5-methoxy-6-methyl-isochroman-3-yl)-piperidin-1-yl]-1-methyl-propyl}-4-chloro-benzamide Stir and heat at 70° C. a solution of 4-chloro-N-{3-[4-(1-formylaminomethyl-5-methoxy-6-methyl-isochroman-3-yl)-piperidin-1-yl]-1-methylpropyl}-benzamide in CH$_3$OH/THF (10 mL of 1:1 solution) and of 15% NaOH solution (2 mL) for 4 hours. Concentrate the reaction mixture, and extract three times with EtOAc (2 mL). Wash the combined organic phase sequentially with H$_2$O (2 mL), brine (2 mL), and then dry over MgSO$_4$. Concentrate and purify the crude product on a 2 g SCX column.

Scheme B, Step B3 N-{3-[4-((1R,3S)-1-Aminomethyl-5-hydroxy-6-methyl-isochroman-3-yl)-piperidin-1-yl]-1-methyl-propyl}-4-chloro-benzamide dihydrochloride Cool a solution of N-{3-[4-((1R,3S)-1-aminomethyl-5-methoxy-6-methyl-isochroman-3-yl)-piperidin-1-yl]-1-methyl-propyl}-4-chloro-benzamide in anhydrous dichloromethane (4 mL) to −20° C., and add 6 equivalents of BCl$_3$ (using 1M BCl$_3$ in dichloromethane) slowly into the solution. Following complete addition, stir the reaction mixture at −20° C. for 2 hours and 0° C. for 1 hour. Cool again to −20° C. and quench with anhydrous CH$_3$OH (0.5 mL). Allow the resulting solution to warm to room temperature and concentrate. Purify the crude product on a 2 g SCX column and then by chromatography on a 1 g silica gel column (eluted by 7N NH$_3$ in methanol:ethyl acetate=1:10). Collect the appropriate fractions, concentrate and convert to the title compound with 2M HCl in diethyl ether. CIMS 486.2, $t_R$ (min)=2.30.

The following examples 14-25 were synthesized similarly to Example 13 with different aldehydes used as reactants the in first step for the reductive amination.

Example 14

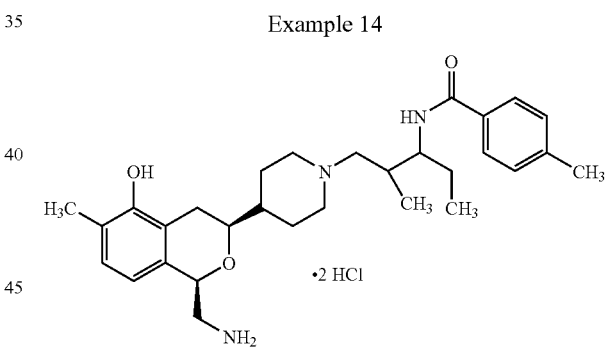

N-{3-[4-((1R,3S)-1-Aminomethyl-5-hydroxy-6-methyl-isochroman-3-yl)-piperidin-1-yl]-1-ethyl-2-methyl-propyl}-4-methyl-benzamide dihydrochloride

| Reactant | Retention time $t_R$ (min) of product | CIMS (MH$^+$) of product |
|---|---|---|
|  | 2.44 | 494.3 |

Example 15

N-{3-[4-((1R,3S)-1-Aminomethyl-5-hydroxy-6-methyl-isochroman-3-yl)-piperidin-1-yl]-1-methyl-propyl}-4-methyl-benzamide dihydrochloride

| Reactant | Retention time $t_R$ (min) of product | CIMS (MH$^+$) of product |
|---|---|---|
|  | 2.25 | 466.3 |

Example 16

N-{3-[4-((1R,3S)-1-Aminomethyl-5-hydroxy-6-methyl-isochroman-3-yl)-piperidin-1-yl]-1-methyl-propyl}-4-trifluoromethyl-benzamide dihydrochloride

| Reactant aldehyde | Retentiom time $t_R$ (min) of product | CIMS (MH$^+$) of product |
|---|---|---|
|  | 2.40 | 520.3 |

Example 17

N-{3-[4-((1R,3S)-1-Aminomethyl-5-hydroxy-6-methyl-isochroman-3-yl)-piperidin-1-yl]-1-methyl-propyl}-2,4-dichloro-benzamide dihydrochloride

| Reactant aldehyde | Retention time $t_R$ (min) of product | CIMS (MH$^+$) of product |
|---|---|---|
|  | 2.30 | 520.2 |

Example 18

Biphenyl-4-carboxylic acid {3-[4-((1R,3S)-1-aminomethyl-5-hydroxy-6-methyl-isochroman-3-yl)-piperidin-1-yl]-1-methyl-propyl}-amide dihydrochloride

| Reactant aldehyde | Retention time $t_R$ (min) of product | CIMS (MH$^+$) of product |
|---|---|---|
|  | 2.54 | 528.3 |

Example 19

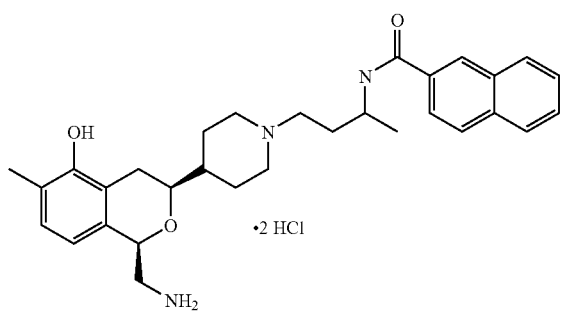

Naphthalene-2-carboxylic acid {3-[4-((1R,3S)-1-aminomethyl-5-hydroxy-6-methyl-isochroman-3-yl)-piperidin-1-yl]-1-methyl-propyl}-amide dihydrochloride

| Reactant aldehyde | Retention time $t_R$ (min) of product | CIMS (MH+) of product |
|---|---|---|
|  | 2.24 | 502.3 |

Example 20

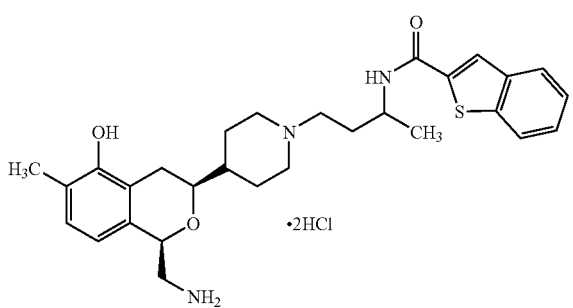

Benzo[b]thiophene-2-carboxylic acid {3-[4-((1R,3S)-1-aminomethyl-5-hydroxy-6-methyl-isochroman-3-yl)-piperidin-1-yl]-1-methyl-propyl}-amide dihydrochloride

| Reactant aldehyde | Retention time $t_R$ (min) of product | CIMS (MH+) of product |
|---|---|---|
|  | 2.39 | 508.3 |

Example 21

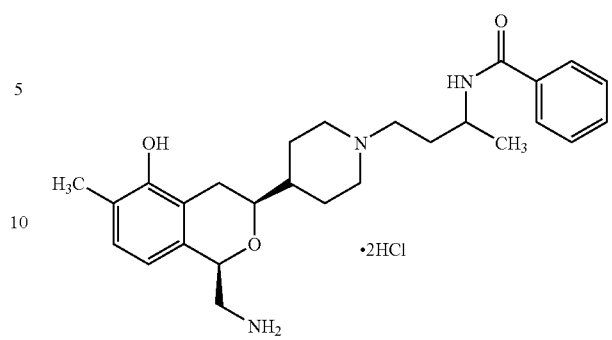

N-{3-[4-((1R,3S)-1-Aminomethyl-5-hydroxy-6-methyl-isochroman-3-yl)-piperidin-1-yl]-1-methyl-propyl}-benzamide dihydrochloride

| Reactant aldehyde | Retention time $t_R$ (min) of product | CIMS (MH+) of product |
|---|---|---|
|  | 2.15 | 452.4 |

Example 22

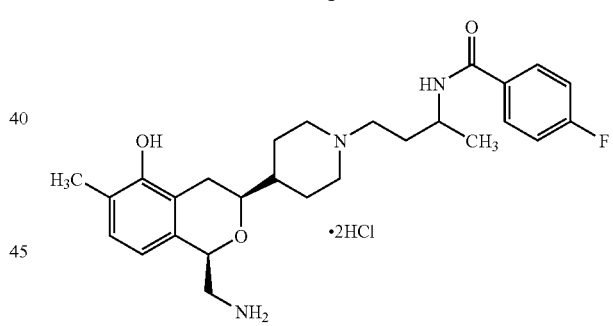

N-{3-[4-((1R,3S)-1-Aminomethyl-5-hydroxy-6-methyl-isochroman-3-yl)-piperidin-1-yl]-1-methyl-propyl}-4-fluoro-benzamide dihydrochloride

| Reactant aldehyde | Retention time $t_R$ (min) of product | CIMS (MH+) of product |
|---|---|---|
|  | 2.19 | 470.3 |

Example 23

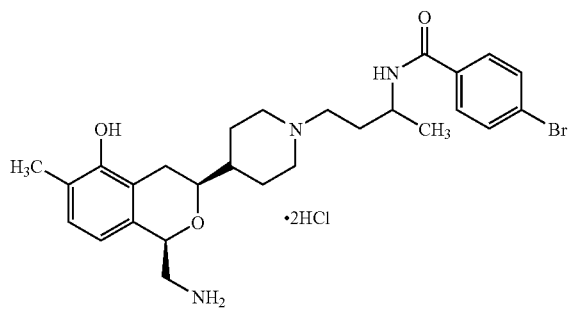

N-{3-[4-((1R,3S)-1-Aminomethyl-5-hydroxy-6-methyl-isochroman-3-yl)-piperidin-1-yl]-1-methyl-propyl}-4-bromo-benzamide dihydrochloride

| Reactant aldehyde | Retention time $t_R$ (min) of product | CIMS (MH$^+$) of product |
|---|---|---|
| (structure shown) | 2.34 | 530.2 |

Example 24

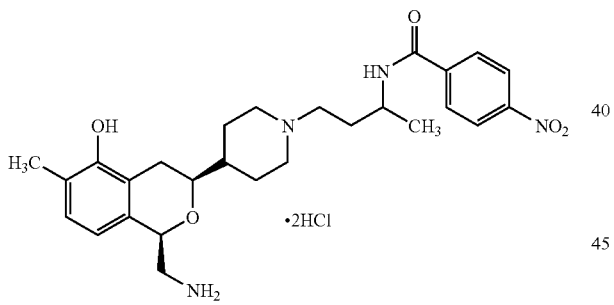

N-{3-[4-((1R,3S)-1-Aminomethyl-5-hydroxy-6-methyl-isochroman-3-yl)-piperidin-1-yl]-1-methyl-propyl}-4-nitro-benzamide dihydrochloride

| Reactant aldehyde | Retention time $t_R$ (min) of product | CIMS (MH$^+$) of product |
|---|---|---|
| (structure shown) | 2.19 | 497.3 |

Example 25

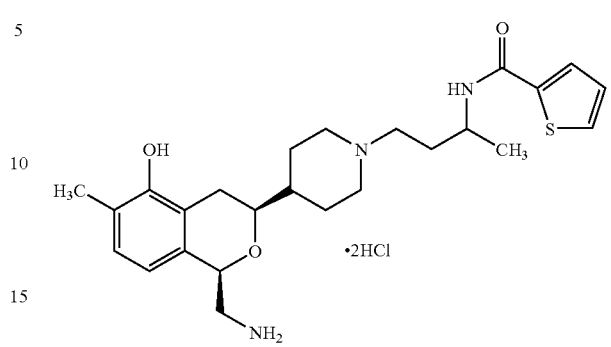

Thiophene-2-carboxylic acid {3-[4-((1R,3S)-1-aminomethyl-5-hydroxy-6-methyl-isochroman-3-yl)-piperidin-1-yl]-1-methyl-propyl}-amide dihydrochloride

| Reactant aldehyde | Retention time $t_R$ (min) of product | CIMS (MH$^+$) of product |
|---|---|---|
| (structure shown) | 2.10 | 458.2 |

Example 26

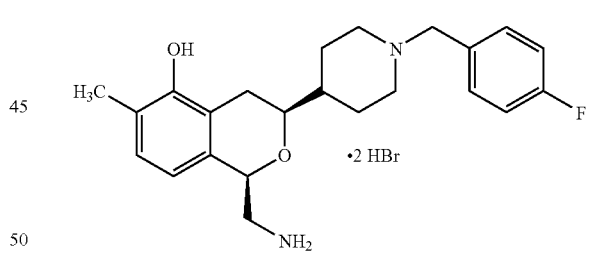

(1R,3S)-1-Aminomethyl-3-[1-(4-fluoro-benzyl)-piperidin-4-yl]-6-methyl-isochroman-5-ol dihydrobromide Scheme B, Step B1: N-[3-[1-(4-fluoro-benzyl)-piperidin-4-yl]-5-isopropoxy-6-methyl-isochroman-1-ylmethyl]-formamide Stir a suspension of N-((1R,3S)-5-Isopropoxy-6-methyl-3-(4-piperidinyl)-1-isochromanylmethyl)formamide (1.0 mmol) with 4-fluorobenzaldehyde (3.0 mmol) and sodium triacetoxyborohydride (3.0 mmol) in dichloromethane (5 mL) at room temperature overnight. Apply the reaction mixture directly to a 5 g SCX column and elute and concentrate the appropriate fractions to obtain N-[3-[1-(4-fluoro-benzyl)-piperidin-4-yl]-5-isopropoxy-6-methyl-isochroman-1-ylmethyl]-formamide. Use the compound directly for the next step.

Scheme B, step B4: (1R,3S)-1-Aminomethyl-3-[1-(4-fluoro-benzyl)-piperidin-4-yl]-6-methyl-isochroman-5-ol dihydrobromide To compound N-[3-[1-(4-fluoro-benzyl)-piperidin-4-yl]-5-isopropoxy-6-methyl-isochroman-1-ylmethyl]-formamide from the previous step in an 8 mL vial add 48% HBr (0.34 mL) and of acetic acid (0.34 mL). Heat and stir the reaction mixture at 85° C. overnight. Concentrate the reaction mixture and purify the crude product on a 2 g SCX column and then by a 2 g silica gel column (7N $NH_3$ in methanol:ethyl acetate=1:10). Concentrate the appropriate fractions and convert to the title compound dihydrobromide by treatment with HBr-saturated methanol. CIMS 385.3 (MH$^+$).

The following examples 27-92 were synthesized similarly to Example 26 with different aldehydes or ketones used as reactants in the first step for the reductive amination. In some examples, compounds were converted to hydrochloride salts instead of hydrobromides, by using saturated HCl in an alcoholic or ethereal solvent instead of HBr-saturated methanol.

Example 27

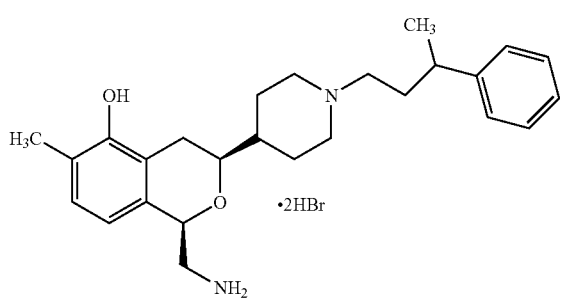

(1R,3S)-1-Aminomethyl-6-methyl-3-[1-(3-phenyl-butyl)-piperidin-4-yl]-isochroman-5-ol dihydrobromide

| Reactant aldehyde | Retention time $t_R$ (min) of product | CIMS (MH$^+$) of product |
|---|---|---|
| ![aldehyde] | 1.20 | 409.3 |

Example 28

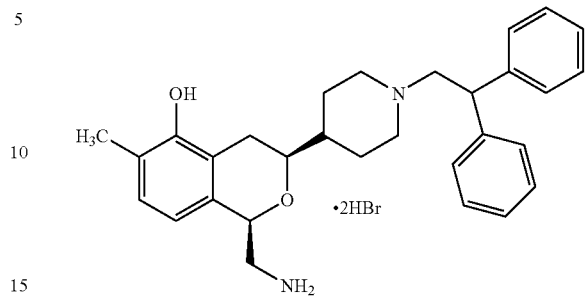

(1R,3S)-1-Aminomethyl-3-[1-(2,2-diphenyl-ethyl)-piperidin-4-yl]-6-methyl-isochroman-5-ol dihydrobromide

| Reactant aldehyde | Retention time $t_R$ (min) of product | CIMS (MH$^+$) of product |
|---|---|---|
| ![aldehyde] | 1.19 | 457.3 |

Example 29

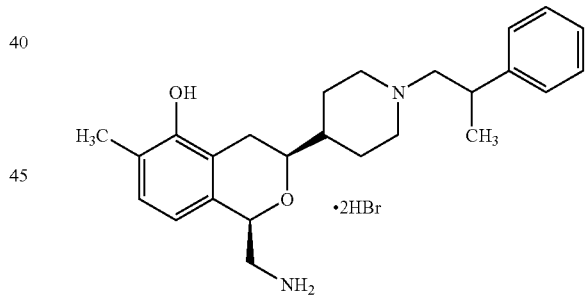

(1R,3S)-1-Aminomethyl-3-[1-(2-phenyl-propyl)-piperidin-4-yl]-6-methyl-isochroman-5-ol dihydrobromide

| Reactant aldehyde | Retention time $t_R$ (min) of product | CIMS (MH$^+$) of product |
|---|---|---|
| ![aldehyde] | 1.20 | 409.3 |

Example 30

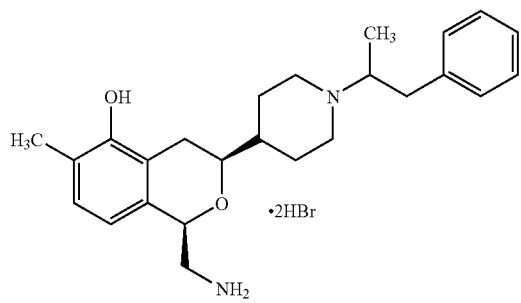

(1R,3S)-1-Aminomethyl-6-methyl-3-[1-(1-methyl-2-phenyl-ethyl)-piperidin-4-yl]-isochroman-5-ol dihydrobromide

| Reactant ketone | Retention time $t_R$ (min) of product | CIMS (MH$^+$) of product |
|---|---|---|
| ![ketone] | 1.14 | 395.3 |

Example 31

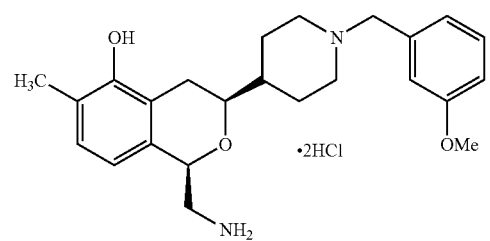

(1R,3S)-1-Aminomethyl-3-[1-(3-methoxy-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| ![aldehyde] | 1.08 | 397.3 |

Example 32

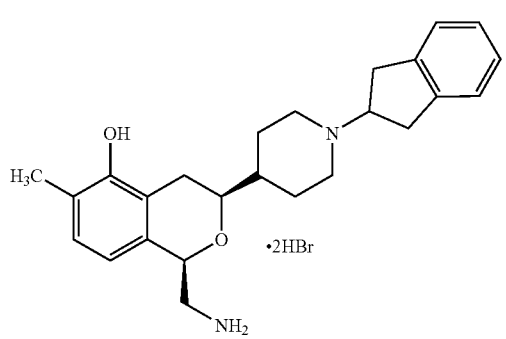

(1R,3S)-1-Aminomethyl-3-(1-indan-2-yl-piperidin-4-yl)-6-methyl-isochroman-5-ol dihydrobromide

| Reactant ketone | Retention time $t_R$ (min) of product | CIMS (MH$^+$) of product |
|---|---|---|
| ![indanone] | 1.07 | 393.2 |

Example 33

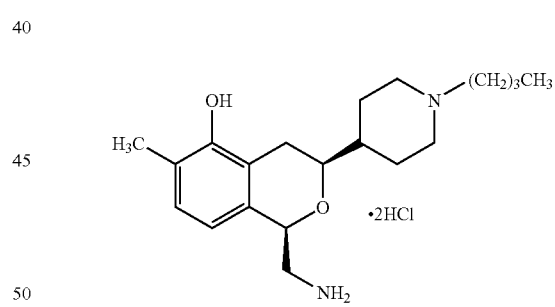

(1R,3S)-1-Aminomethyl-3-(1-butyl-piperidin-4-yl)-6-methyl-isochroman-5-ol dihydrochloride

| Reactant aldehyde | Retention time $t_R$ (min) of product | CIMS (MH$^+$) of product |
|---|---|---|
| H-CO-(CH$_2$)$_2$CH$_3$ | 0.96 | 333.2 |

Example 34

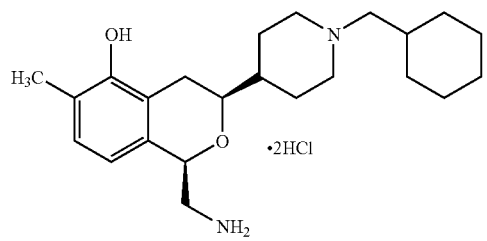

(1R,3S)-1-Aminomethyl-3-(1-cyclohexylmethyl-piperidin-4-yl)-6-methyl-isochroman-5-ol dihydrochloride

| Reactant aldehyde | Retention time $t_R$ (min) of product | CIMS (MH$^+$) of product |
|---|---|---|
|  | 1.08 | 373.2 |

Example 35

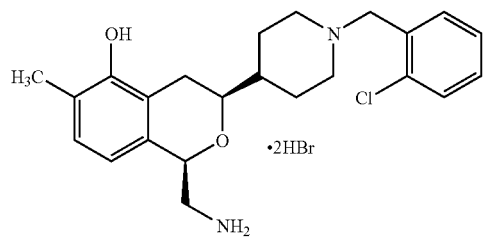

(1R,3S)-1-Aminomethyl-3-[1-(2-chloro-benzyl)-piperidin-4-yl]-6-methyl-isochroman-5-ol dihydrobromide

| Reactant aldehyde | Retention time $t_R$ (min) of product | CIMS (MH$^+$) of product |
|---|---|---|
|  | 2.01 | 401.2 |

Example 36

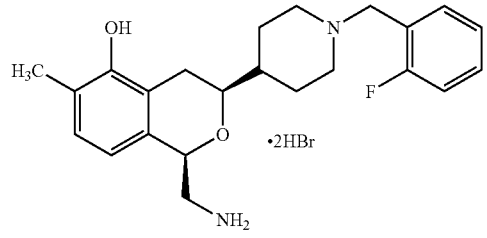

(1R,3S)-1-Aminomethyl-3-[1-(2-fluoro-benzyl)-piperidin-4-yl]-6-methyl-isochroman-5-ol dihydrobromide

| Reactant aldehyde | Retention time $t_R$ (min) of product | CIMS (MH$^+$) of product |
|---|---|---|
|  | 1.32 | 385.2 |

Example 37

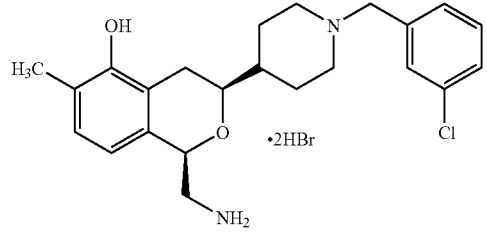

(1R,3S)-1-Aminomethyl-3-[1-(3-chloro-benzyl)-piperidin-4-yl]-6-methyl-isochroman-5-ol dihydrobromide

| Reactant aldehyde | Retention time $t_R$ (min) of product | CIMS (MH$^+$) of product |
|---|---|---|
|  | 1.39 | 401.4 |

Example 38

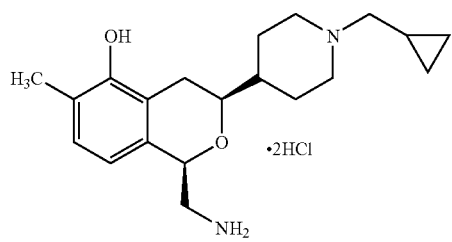

(1R,3S)-1-Aminomethyl-3-(1-cyclopropylmethyl-piperidin-4-yl)-6-methyl-isochroman-5-ol dihydrochloride

| Reactant aldehyde | Retention time $t_R$ (min) of product | CIMS (MH$^+$) of product |
|---|---|---|
| ![cyclopropanecarbaldehyde] | 0.90 | 331.2 |

Example 39

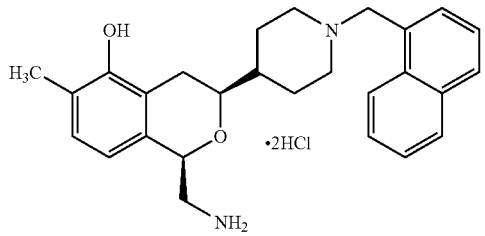

(1R,3S)-1-Aminomethyl-6-methyl-3-(1-naphthalen-1-ylmethyl-piperidin-4-yl)-isochroman-5-ol dihydrochloride

| Reactant aldehyde | Retention time $t_R$ (min) of product | CIMS (MH$^+$) of product |
|---|---|---|
| ![1-naphthaldehyde] | 2.63 | 417.1 |

Example 40

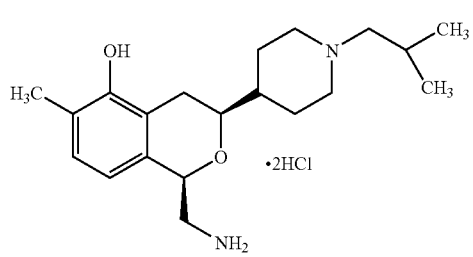

(1R,3S)-1-Aminomethyl-3-(1-isobutyl-piperidin-4-yl)-6-methyl-isochroman-5-ol dihydrochloride

| Reactant aldehyde | Retention time $t_R$ (min) of product | CIMS (MH$^+$) of product |
|---|---|---|
| ![isobutyraldehyde] | 2.24 | 333.2 |

Example 41

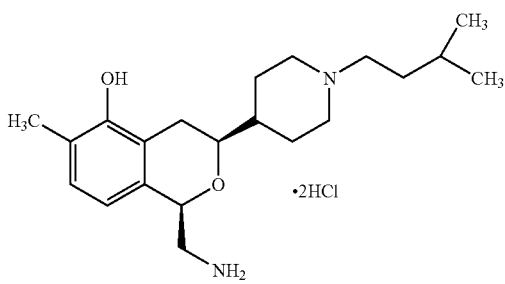

(1R,3S)-1-Aminomethyl-6-methyl-3-[1-(3-methyl-butyl)-piperidin-4-yl]-isochroman-5-ol dihydrochloride

| Reactant aldehyde | Retention time $t_R$ (min) of product | CIMS (MH$^+$) of product |
|---|---|---|
| ![3-methylbutyraldehyde] | 2.39 | 347.2 |

Example 42

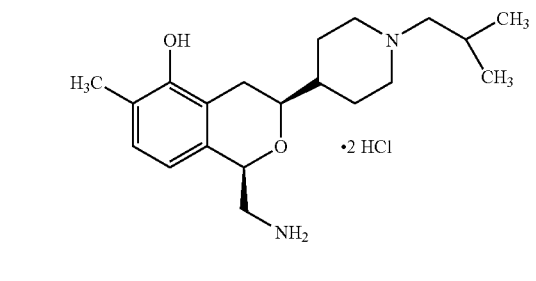

(1R,3S)-1-Aminomethyl-3-[1-(2,2-dimethyl-propyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| 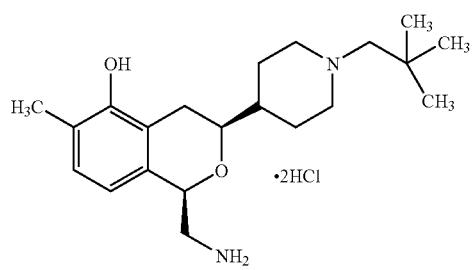 | 2.30 | 347.2 |

Example 43

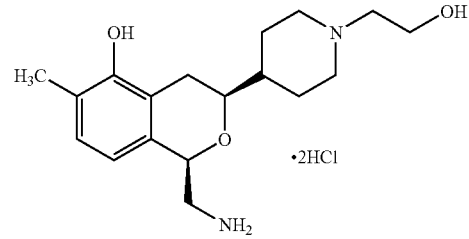

(1R,3S)-1-Aminomethyl-3-[1-(2-hydroxy-ethyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| | 2.07 | 321.2 |

Example 44

(1R,3S)-1-Aminomethyl-3-(1-isopropyl-piperidin-4-yl)-6-methyl-isochroman-5-ol dihydrochloride

| Reactant aldehyde | Retention time $t_R$ (min) of product | CIMS (MH$^+$) of product |
|---|---|---|
| | 2.20 | 319.2 |

Example 45

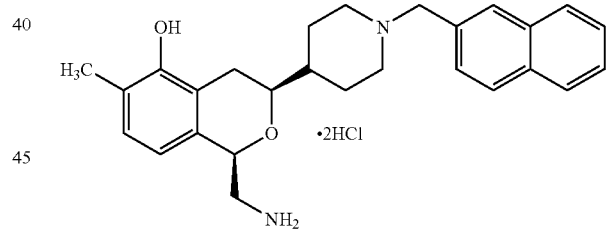

(1R,3S)-1-Aminomethyl-6-methyl-3-(1-naphthalen-2-ylmethyl-piperidin-4-yl)-isochroman-5-ol dihydrochloride

| Reactant aldehyde | Retention time $t_R$ (min) of product | CIMS (MH$^+$) of product |
|---|---|---|
| | 2.64 | 417.2 |

Example 46

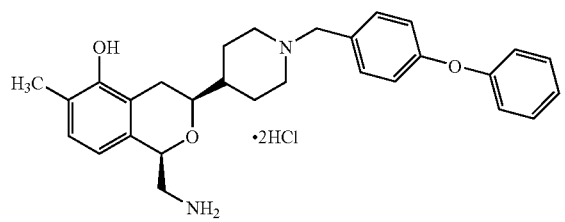

(1R,3S)-1-Aminomethyl-6-methyl-3-[1-(4-phenoxy-benzyl)-piperidin-4-yl]-isochroman-5-ol dihydrochloride

| Reactant aldehyde | Retention time $t_R$ (min) of product | CIMS (MH$^+$) of product |
|---|---|---|
| | 2.82 | 459.2 |

Example 47

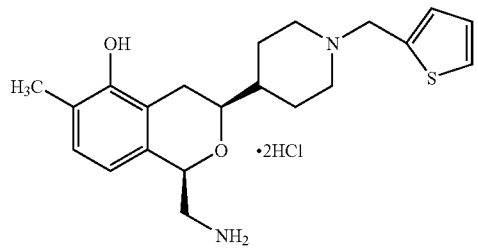

(1R,3S)-1-Aminomethyl-6-methyl-3-(1-thiophen-2-ylmethyl-piperidin-4-yl)-isochroman-5-ol dihydrochloride

| Reactant aldehyde | Retention time $t_R$ (min) of product | CIMS (MH$^+$) of product |
|---|---|---|
| | 2.32 | 373.1 |

Example 48

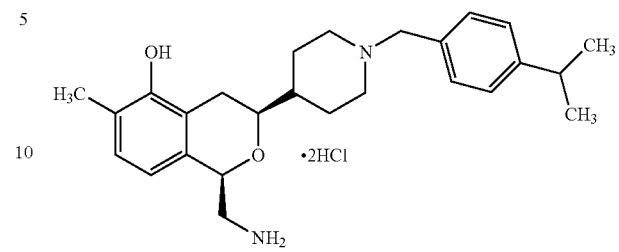

(1R 3S)-1-Aminomethyl-3-[1-(4-isopropyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| | 2.73 | 409.2 |

Example 49

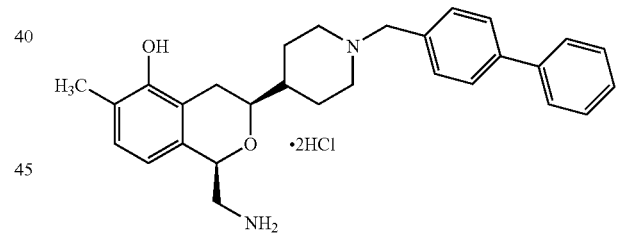

(1R,3S)-1-Aminomethyl-3-(1-biphenyl-4-ylmethyl-piperidin-4-yl)-6-methyl-isochroman-5-ol dihydrochloride

| Reactant aldehyde | Retention time $t_R$ (min) of product | CIMS (MH$^+$) of product |
|---|---|---|
| | 2.73 | 443.2 |

Example 50

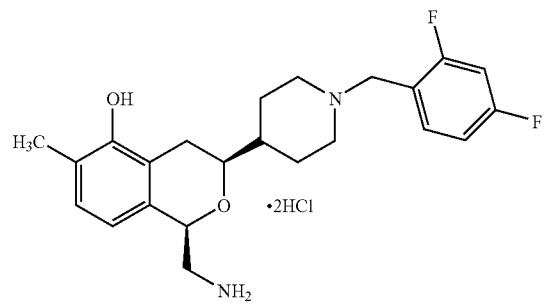

(1R,3S)-1-Aminomethyl-3-[1-(2,4-difluoro-benzyl)-piperidin-4-yl]-6-methyl-isochroman-5-ol dihydrochloride

| Reactant aldehyde | Retention time $t_R$ (min) of product | CIMS (MH⁺) of product |
|---|---|---|
| (2,4-difluorobenzaldehyde) | 2.45 | 403.1 |

Example 51

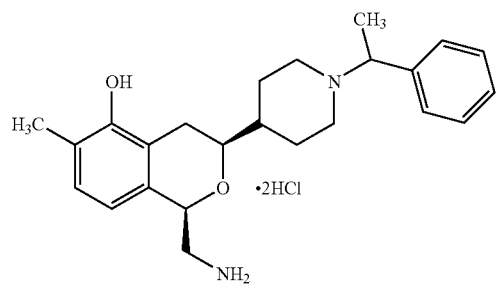

(1R,3S)-1-Aminomethyl-6-methyl-3-[1-(1-phenyl-ethyl)-piperidin-4-yl]-isochroman-5-ol dihydrochloride

| Reactant ketone | Retention time $t_R$ (min) of product | CIMS (MH⁺) of product |
|---|---|---|
| (acetophenone) | 2.42 | 381.3 |

Example 52

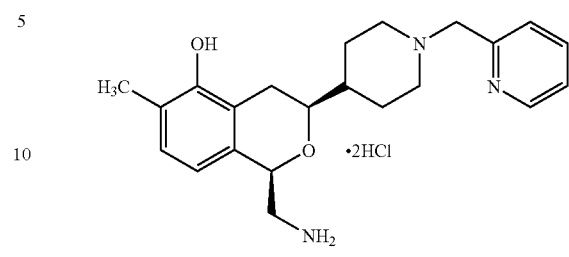

(1R,3S)-1-Aminomethyl-6-methyl-3-(1-pyridin-2-ylmethyl-piperidin-4-yl)-isochroman-5-ol dihydrochloride

| Reactant aldehyde | Retention time $t_R$ (min) of product | CIMS (MH⁺) of product |
|---|---|---|
| (pyridine-2-carbaldehyde) | 2.20 | 368.3 |

Example 53

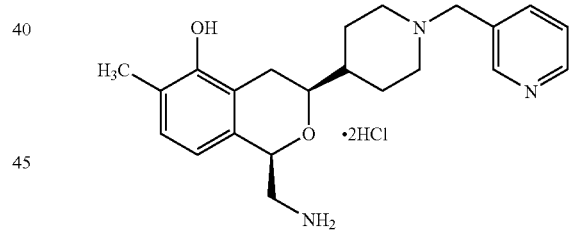

(1R,3S)-1-Aminomethyl-6-methyl-3-(1-pyridin-3-ylmethyl-piperidin-4-yl)-isochroman-5-ol dihydrochloride

| Reactant aldehyde | Retention time $t_R$ (min) of product | CIMS (MH⁺) of product |
|---|---|---|
| (pyridine-3-carbaldehyde) | 2.10 | 368.3 |

Example 54

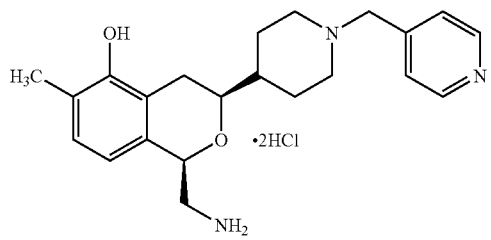

(1R,3S)-1-Aminomethyl-6-methyl-3-(1-pyridin-4-ylmethyl-piperidin-4-yl)-isochroman-5-ol dihydrochloride

| Reactant aldehyde | Retention time $t_R$ (min) of product | CIMS (MH$^+$) of product |
|---|---|---|
|  | 2.07 | 368.3 |

Example 55

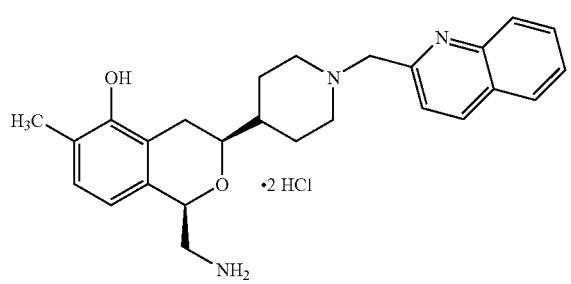

(1R,3S)-1-Aminomethyl-6-methyl-3-(1-quinolin-2-ylmethyl-piperidin-4-yl)-isochroman-5-ol dihydrochloride

| Reactant aldehyde | Retention time $t_R$ (min) of product | CIMS (MH$^+$) of product |
|---|---|---|
|  | 2.47 | 418.3 |

Example 56

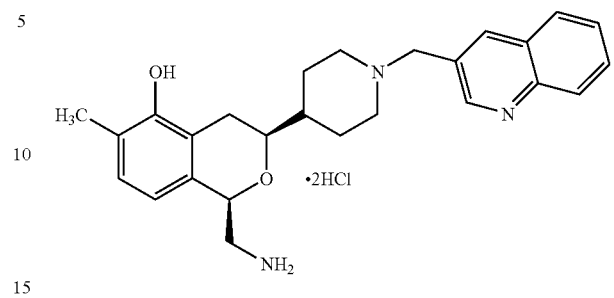

(1R,3S)-1-Aminomethyl-6-methyl-3-(1-quinolin-3-ylmethyl-piperidin-4-yl)-isochroman-5-ol dihydrochloride

| Reactant aldehyde | Retention time $t_R$ (min) of product | CIMS (MH$^+$) of product |
|---|---|---|
|  | 2.29 | 418.3 |

Example 57

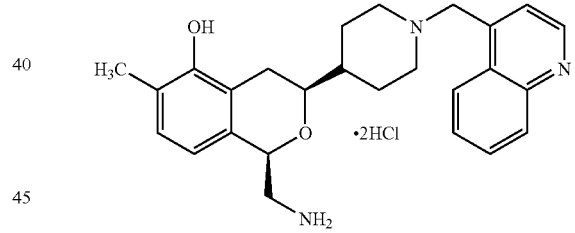

(1R,3S)-1-Aminomethyl-6-methyl-3-(1-quinolin-4-ylmethyl-piperidin-4-yl)-isochroman-5-ol dihydrochloride

| Reactant aldehyde | Retention time $t_R$ (min) of product | CIMS (MH$^+$) of product |
|---|---|---|
|  | 2.20 | 418.3 |

Example 58

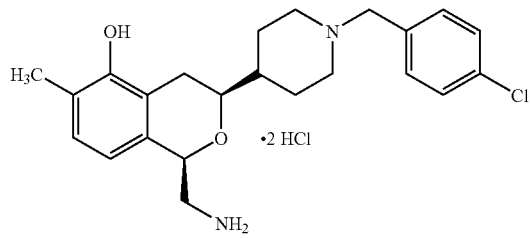

(1R,3S)-1-Aminomethyl-3-[1-(4-chloro-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (4-chlorobenzaldehyde) | 2.49 | 401.2 |

Example 59

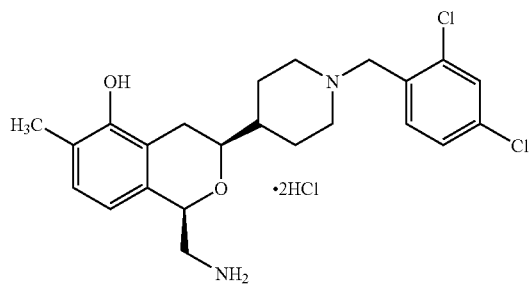

(1R,3S)-1-Aminomethyl-3-[1-(2,4-dichloro-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2,4-dichlorobenzaldehyde) | 2.57 | 435.2 |

Example 60

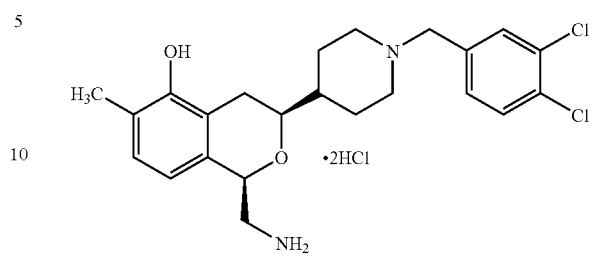

(1R,3S)-1-Aminomethyl-3-[1-(3,4-dichloro-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3,4-dichlorobenzaldehyde) | 2.60 | 435.2 |

Example 61

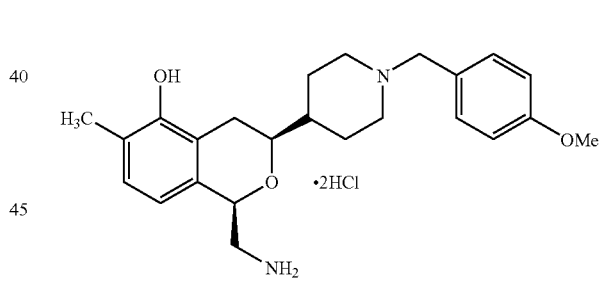

(1R,3S)-1-Aminomethyl-3-[1-(4-methoxy-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (4-methoxybenzaldehyde) | 2.40 | 397.2 |

Example 62

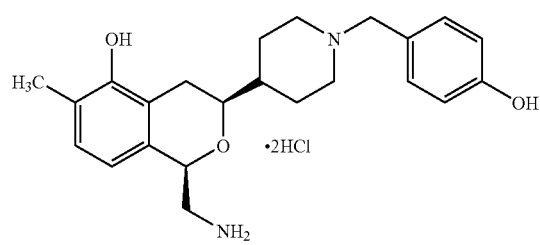

(1R,3S)-1-Aminomethyl-3-[1-(4-hydroxy-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (4-hydroxybenzaldehyde) | 2.22 | 383.3 |

Example 63

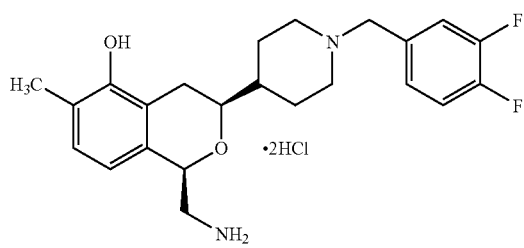

(1R,3S)-1-Aminomethyl-3-[1-(3,4-difluoro-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3,4-difluorobenzaldehyde) | 2.44 | 403.2 |

Example 64

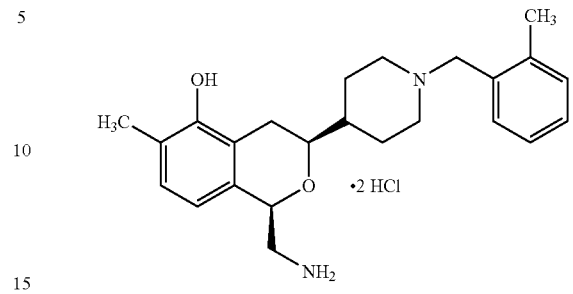

(1R,3S)-1-Aminomethyl-6-methyl-3-[1-(2-methyl-benzyl)-piperidin-4-yl]-isochroman-5-ol dihydrochloride

| Reactant aldehyde | Retention time $t_R$ (min) of product | CIMS (MH$^+$) of product |
|---|---|---|
| (2-methylbenzaldehyde) | 2.40 | 381.2 |

Example 65

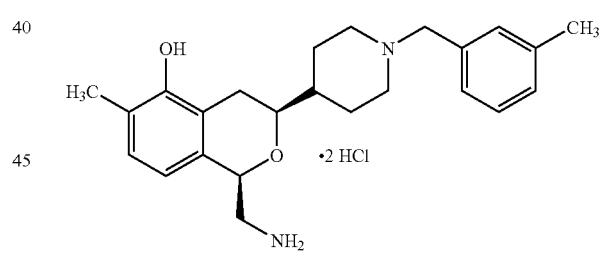

(1R,3S)-1-Aminomethyl-6-methyl-3-[1-(3-methyl-benzyl)-piperidin-4-yl]-isochroman-5-ol dihydrochloride

| Reactant aldehyde | Retention time $t_R$ (min) of product | CIMS (MH$^+$) of product |
|---|---|---|
| (3-methylbenzaldehyde) | 2.44 | 381.2 |

Example 66

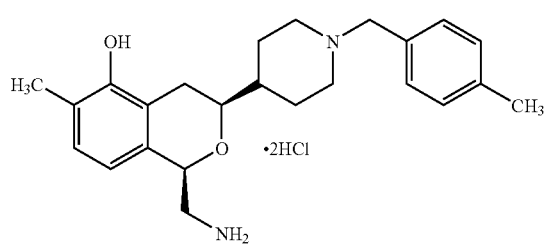

(1R,3S)-1-Aminomethyl-6-methyl-3-[1-(4-methyl-benzyl)-piperidin-4-yl]-isochroman-5-ol dihydrochloride

| Reactant aldehyde | Retention time $t_R$ (min) of product | CIMS (MH$^+$) of product |
|---|---|---|
| (4-methylbenzaldehyde) | 2.46 | 381.2 |

Example 67

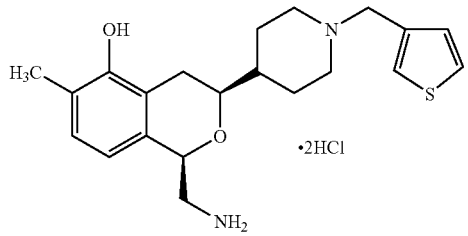

(1R,3S)-1-Aminomethyl-6-methyl-3-(1-thiophen-3-ylmethyl-piperidin-4-yl)-isochroman-5-ol dihydrochloride

| Reactant aldehyde | Retention time $t_R$ (min) of product | CIMS (MH$^+$) of product |
|---|---|---|
| (thiophene-3-carbaldehyde) | 2.30 | 373.2 |

Example 68

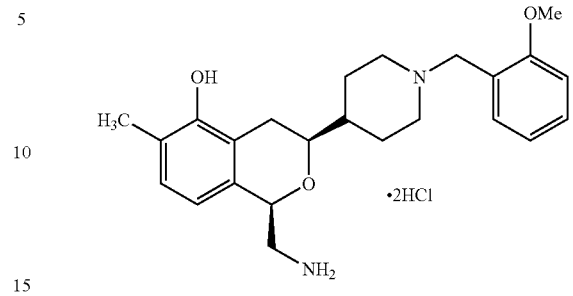

(1R,3S)-1-Aminomethyl-3-[1-(2-methoxy-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2-methoxybenzaldehyde) | 2.35 | 397.2 |

Example 69

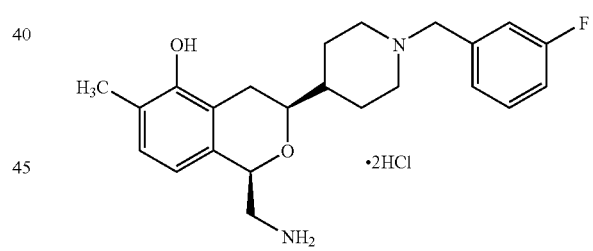

(1R,3S)-1-Aminomethyl-3-[1-(3-fluoro-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3-fluorobenzaldehyde) | 2.37 | 385.2 |

Example 70

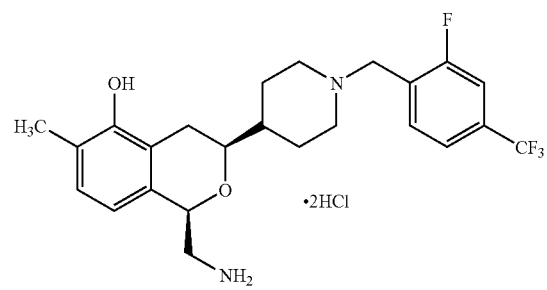

(1R,3S)-1-Aminomethyl-3-[1-(2-fluoro-4-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| | 2.59 | 453.2 |

Example 71

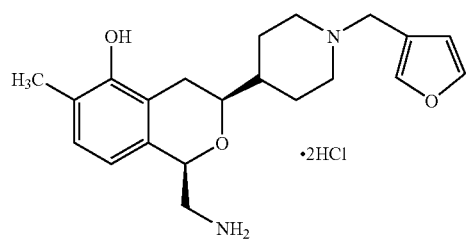

(1R,3S)-1-Aminomethyl-3-(1-furan-3-ylmethyl-piperidin-4-yl)-6-methyl-isochroman-5-ol hydrochloride

| Reactant aldehyde | Retention time $t_R$ (min) of product | CIMS (MH$^+$) of product |
|---|---|---|
| | 2.20 | 357.2 |

Example 72

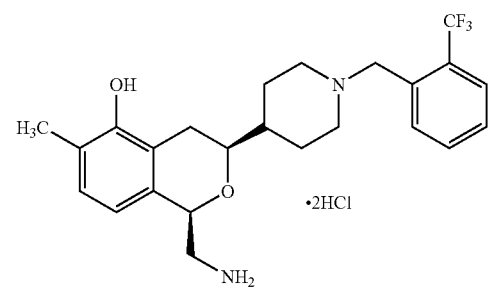

(1R,3S)-1-Aminomethyl-6-methyl-3-[1-(2-trifluoromethyl-benzyl)-piperidin-4-yl]-isochroman-5-ol dihydrochloride

| Reactant aldehyde | Retention time $t_R$ (min) of product | CIMS (MH$^+$) of product |
|---|---|---|
| | 2.05 | 435.2 |

Example 73

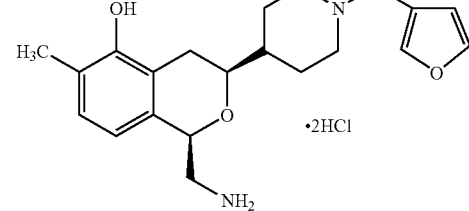

(1R,3S)-1-Aminomethyl-6-methyl-3-[1-(3-trifluoromethyl-benzyl)-piperidin-4-yl]-isochroman-5-ol dihydrochloride

| Reactant aldehyde | Retention time $t_R$ (min) of product | CIMS (MH$^+$) of product |
|---|---|---|
| | 2.13 | 435.2 |

Example 74

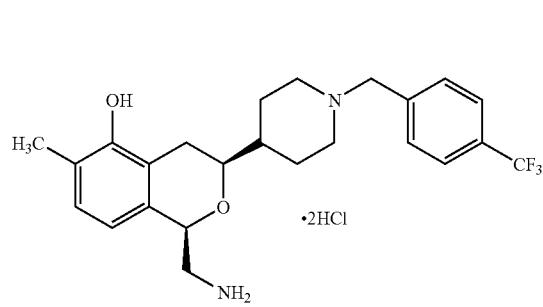

(1R,3S)-1-Aminomethyl-6-methyl-3-[1-(4-trifluoromethyl-benzyl)-piperidin-4-yl]-isochroman-5-ol dihydrochloride

| Reactant aldehyde | Retention time $t_R$ (min) of product | CIMS (MH$^+$) of product |
|---|---|---|
| (4-CF₃-benzaldehyde) | 2.65 | 435.2 |

Example 76

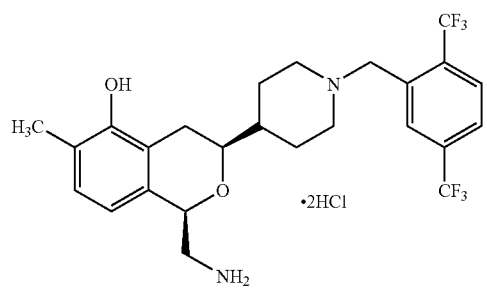

(1R,3S)-1-Aminomethyl-3-[1-(2,5-bis-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2,5-bis-CF₃-benzaldehyde) | 2.22 | 503.2 |

Example 75

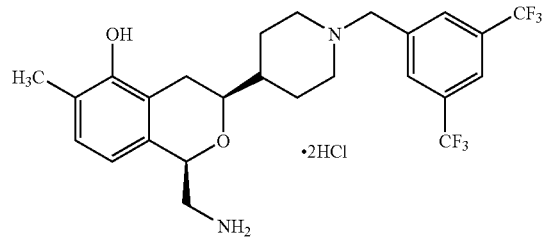

(1R,3S)-1-Aminomethyl-3-[1-(3,5-bis-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3,5-bis-CF₃-benzaldehyde) | 2.32 | 503.2 |

Example 77

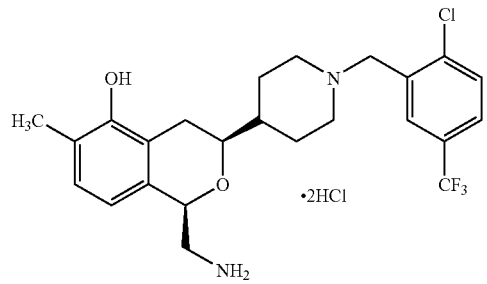

(1R,3S)-1-Aminomethyl-3-[1-(2-chloro-5-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2-Cl-5-CF₃-benzaldehyde) | 2.12 | 469.1 |

Example 78

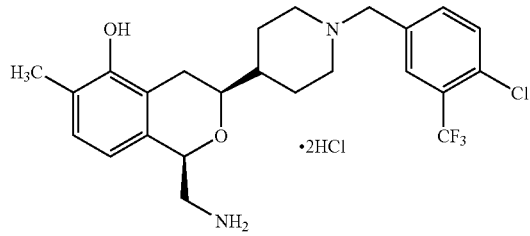

(1R,3S)-1-Aminomethyl-3-[1-(4-chloro-3-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3-chloro-4-CF3 benzaldehyde) | 2.22 | 469.1 |

Example 79

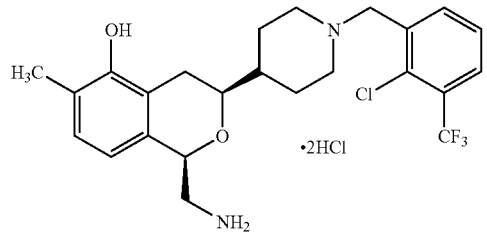

(1R,3S)-1-Aminomethyl-3-[1-(2-chloro-3-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2-chloro-3-CF3 benzaldehyde) | 2.19 | 469.0 |

Example 80

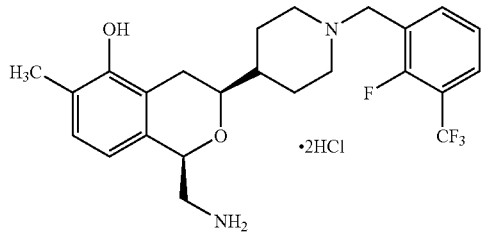

(1R,3S)-1-Aminomethyl-3-[1-(2-fluoro-3-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2-fluoro-3-CF3 benzaldehyde) | 2.14 | 453.0 |

Example 81

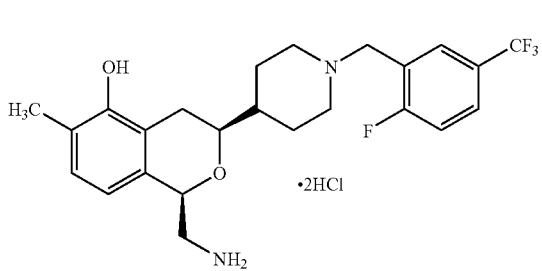

(1R,3S)-1-Aminomethyl-3-[1-(2-fluoro-5-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (2-fluoro-5-CF3 benzaldehyde) | 2.12 | 453.0 |

Example 82

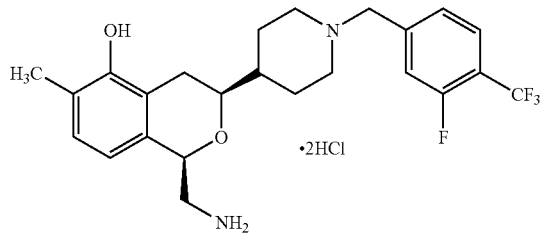

(1R,3S)-1-Aminomethyl-3-[1-(3-fluoro-4-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3-fluoro-4-trifluoromethyl-benzaldehyde) | 2.22 | 453.0 |

Example 84

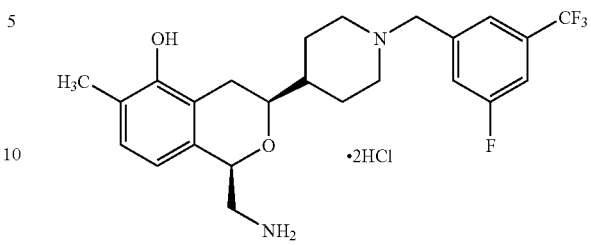

(1R,3S)-1-Aminomethyl-3-[1-(3-fluoro-5-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (3-fluoro-5-trifluoromethyl-benzaldehyde) | 2.19 | 453.2 |

Example 83

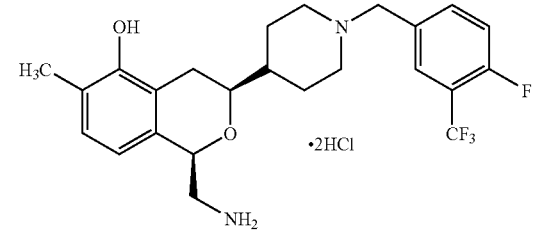

(1R,3S)-1-Aminomethyl-3-[1-(4-fluoro-3-trifluoromethyl-benzyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (4-fluoro-3-trifluoromethyl-benzaldehyde) | 2.19 | 453.0 |

Example 85

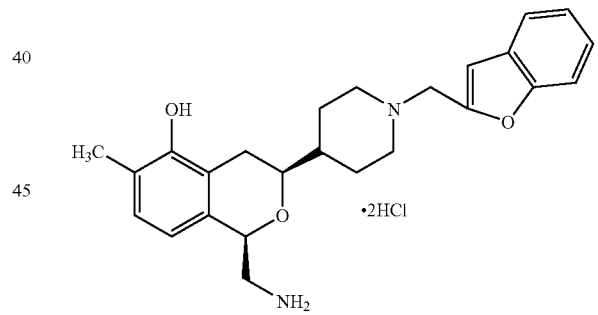

(1R,3S)-1-Aminomethyl-3-(1-benzofuran-2-ylmethyl-piperidin-4-yl)-6-methyl-isochroman-5-ol dihydrochloride

| Reaction aldehyde | Retention time $t_R$ (min) of product | CIMS (MH$^+$) of product |
|---|---|---|
| (benzofuran-2-carbaldehyde) | 2.95 | 407.2 |

Example 86

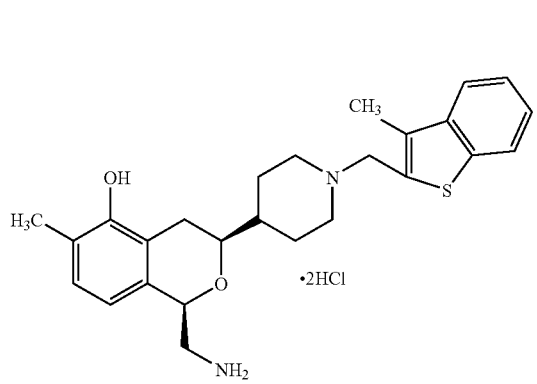

(1R,3S)-1-Aminomethyl-6-methyl-3-[1-(3-methyl-benzo[b]thiophen-2-ylmethyl)-piperidin-4-yl]-isochroman-5-ol dihydrochloride

| Reactant aldehyde | Retention time $t_R$ (min) of product | CIMS (MH$^+$) of product |
|---|---|---|
| (3-methyl-benzo[b]thiophene-2-carbaldehyde) | 2.97 | 437.5 |

Example 87

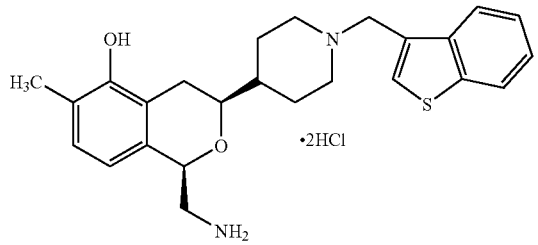

(1R,3S)-1-Aminomethyl-6-methyl-3-(1-benzo[b]thiophen-3-ylmethyl-piperidin-4-yl)-isochroman-5-ol dihydrochloride

| Reactant aldehyde | Retention time $t_R$ (min) of product | CIMS (MH$^+$) of product |
|---|---|---|
| (benzo[b]thiophene-3-carbaldehyde) | 2.72 | 423.3 |

Example 88

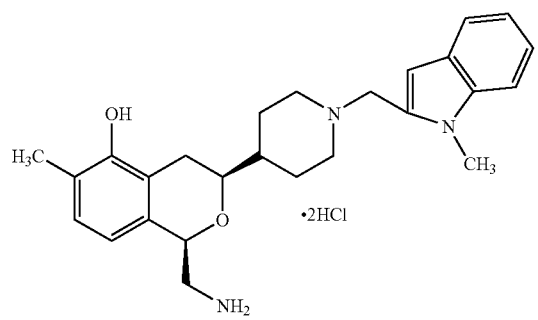

(1R,3S)-1-Aminomethyl-6-methyl-3-[1-(1-methyl-1H-indol-2-ylmethyl)-piperidin-4-yl]-isochroman-5-ol dihydrochloride

| Reactant aldehyde | Retention time $t_R$ (min) of product | CIMS (MH$^+$) of product |
|---|---|---|
| (1-methyl-1H-indole-2-carbaldehyde) | 3.07 | 420.2 |

Example 89

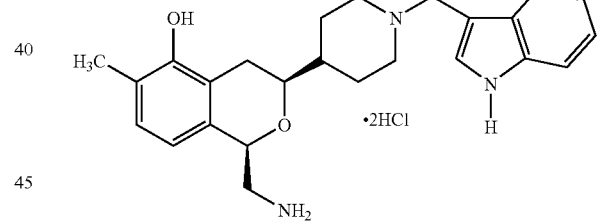

(1R,3S)-1-Aminomethyl-3-[1-(1H-indol-3-ylmethyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| (1H-indole-3-carbaldehyde) | 2.89 | 406.4 |

Example 90

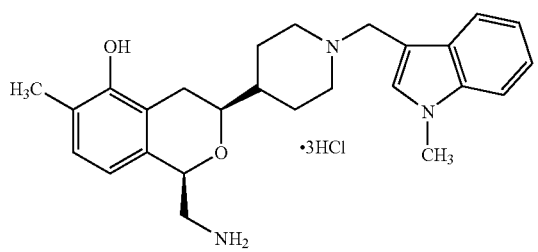

(1R,3S)-1-Aminomethyl-6-methyl-3-[1-(1-methyl-1H-indol-3-ylmethyl)-piperidin-4-yl]-isochroman-5-ol trihydrochloride

| Reactant aldehyde | Retention time $t_R$ (min) of product | CIMS (MH$^+$) of product |
|---|---|---|
| | 2.84 | 420.2 |

Example 91

(1R,3S)-1-Aminomethyl-3-[1-(1-benzyl-1H-indol-3-ylmethyl)-piperidin-4-yl]-6-methyl-isochroman-5-ol dihydrochloride

| Reactant aldehyde | Retention time $t_R$ (min) of product | CIMS (MH$^+$) of product |
|---|---|---|
| | 3.32 | 496.6 |

Example 92

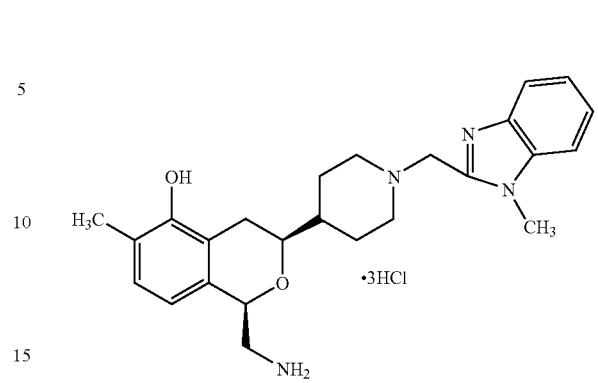

(1R,3S)-1-Aminomethyl-6-methyl-3-[1-(1-methyl-1H-benzoimidazol-2-ylmethyl)-piperidin-4-yl]-isochroman-5-ol trihydrochloride

| Reactant aldehyde | Retention time $t_R$ (min) of product | CIMS (MH$^+$) of product |
|---|---|---|
| | 2.67 | 421.2 |

Example 93

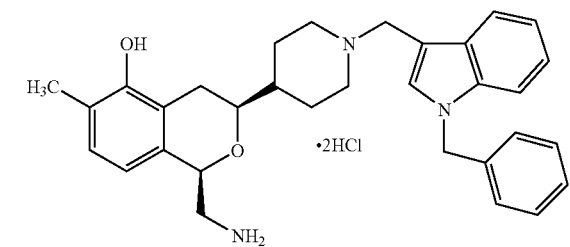

(1R,3S)-1-Aminomethyl-3-[1-(benzyl)-piperidin-4-yl]-6-methyl-isochroman-5-ol dihydrobromide Scheme B, Step B1 (1R,3S)-N-[3-(1-benzyl-piperidin-4-yl)-5-methoxy-6-methyl-isochroman-1-ylmethyl]formamide Stir a suspension of N-((1R,3S)-5-methoxy-6-methyl-3-(4-piperidinyl)-1-isochromanylmethyl)formamide (0.5 g, 1.6 mmol), benzaldehyde (0.16 g, 1.5 mmol), acetic acid (0.9 g and dichloroethane (13 mL) for 5 min. Add sodium triacetoxyborohydride (0.5 g, 2.3 mmol) and stir at room temperature for 4 h. Cool the reaction in an ice bath and and water (18 mL), and then make the make the mixture basic by the addition of 50% aqueous NaOH. Extract the mixture with dichloromethane, filter the biphasic mixture through Celite, separate the phases and reextract the aqueous with dichloromethane. Combine the extracts, wash with $H_2O$, dry over $MSO_4$, filter and concentrate under vacuum to obtain 0.69 g of a brown oil. Purify the crude oil by preparative HPLC on a silica gel cartridge (35 g) and use 2% diethylamine($Et_2NH$)-EtOAc followed by 10% $Et_2NH$-EtOAc. Combine like fractions and concentrate to obtain 0.34 g of the title compound Scheme B, Step B4 (1R,3S)-1-Aminomethyl-3-[1-(benzyl)-piperidin-4-yl]-6-methyl-isochroman-5-ol dihydrobromide To compound (1R,3S)-N-[3-(1-benzyl-piperidin-4-yl)-5-methoxy-6-methyl-isochroman-1-ylmethyl]formamide from the previous step (0.28 g, 0.67 mmol) add 48% HBr (3 mL). Heat and stir the reaction mixture under argon at 100° C. for 1.5 h, and then at room temperature for 2 h. Concentrate the reaction mixture to obtain 0.47 g of brown oil. Dilute the oil with $H_2O$ (20 mL) and basify the mixture with 1M NaOH. After extractive workup with $CH_2Cl_2$ obtain a beige solid, 0.22 g. dissolve the solid in IPA (3-4 mL) and add HBr gas. Stir the solution for 1 h at ambient temperature and then concentrate under vacuum to obtain an oil. The oil was taken up in IPA and ether was added to precipitate 0.22 g of the title compound as a white solid, MS 367 ($MH^+$). Anal. Calculated for $C_{23}H_{30}N_2O_2 \cdot 2HBr \cdot 1.15H_2O$: C, 50.31; H, 6.25; N, 5.10. Found: C, 49.77; H, 6.19; N, 4.71.

Example 94

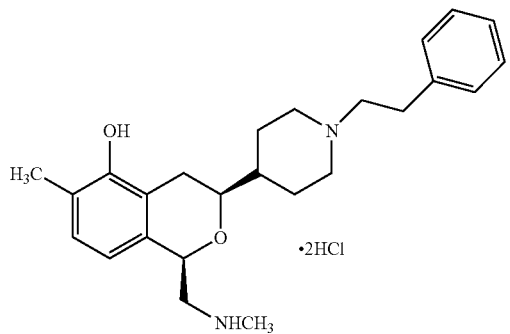

(1R,3S)-6-Methyl-1-methylaminomethyl-3-(1-phenethyl-piperidin-4-yl)-isochroman-5-ol dihydrochloride Scheme B, Step B: (1R,3S)-N-[5-Isopropoxy-6-methyl-3-(1-phenethyl-piperidin-4-yl)-isochroman-1-ylmethyl]-formamide Follow the procedure of Example (for B4) except use phenylacetaldehyde in place of 4-fluorobenzaldehyde to obtain the title compound. Use directly for the next step.

Scheme B Step, B5: (1R,3S) [5-Isopropoxy-6-methyl-3-(1-phenethyl-piperidin-4-yl)-isochroman-1-ylmethyl]-methyl-amine To a solution of 0.5M $LiAlH_4$ in THF (3 mL) at 8° C., add of $AlCl_3$ (35 mg) and (1R,3S)-N-[5-Isopropoxy-6-methyl-3-(1-phenethyl-piperidin-4-yl)-isochroman-1-ylmethyl]-formamide in THF (2 mL). Allow the reaction mixture to warm to 20° C. and stir for 4 hours. Cool to 8° C. and quench by slow addition of saturated, aqueous. $NH_4Cl$ to pH 8. Add EtOAc (8 mL) and then filter the mixture separate the organic layer and concentrate. Purify the residue by chromatography on a 1 g silica gel column (eluent: 10% $CH_3OH/CH_2Cl_2$). Collect the appropriate fractions and concentrate to obtain the title compound.

Scheme B, Step B6: (1R,3S)-6-Methyl-1-methylaminomethyl-3-(1-phenethyl-piperidin-4-yl)-isochroman-5-ol dihydrochloride Cool a solution of (1R,3S) [5-Isopropoxy-6-methyl-3-(1-phenethyl-piperidin-4-yl)-isochroman-1-ylmethyl]-methyl-amine in anhydrous dichloromethane (4 mL) to −20° C., and add 6 equivalents of $BCl_3$ (using 1M $BCl_3$ in dichloromethane) slowly into the solution. Following complete addition, stir the reaction mixture at −20° C. for 2 hours and 0° C. for 1 hour. Cool again to −20° C. and quench with anhydrous $CH_3OH$ (0.5 mL). Allow the resulting solution to warm to room temperature and concentrate. Purify the crude product on a 2 g SCX column and then by chromatography on a 1 g silica gel column (eluted by 7N $NH_3$ in methanol:ethyl acetate=1:10). Collect and concentrate the appropriate fractions and treat with 2M HCl in diethyl ether to obtain the title compound. CIMS 395.4 ($MH^+$), $t_R$ (min)=2.17.

The following examples 95-102 were synthesized similarly to Example 94 with different aldehydes or ketones used as reactants in the first step for the reductive amination. In some examples, compounds were converted to hydrochloride salts instead of hydrobromides, by using saturated HCl in an alcoholic or ethereal solvent instead of HBr-saturated methanol.

Example 95

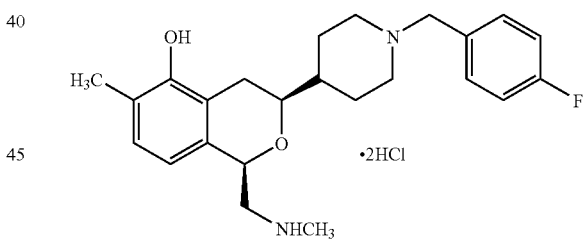

1R,3S)-3-[1-(4-Fluoro-benzyl)-piperidin-4-yl]-6-methyl-1-methylaminomethyl-isochroman-5-ol dihydrochloride

| (Reactant) | Retention time $t_R$ (min) of product | CIMS ($MH^+$) of product |
|---|---|---|
| ![4-fluorobenzaldehyde] | 2.12 | 399.4 |

Example 96

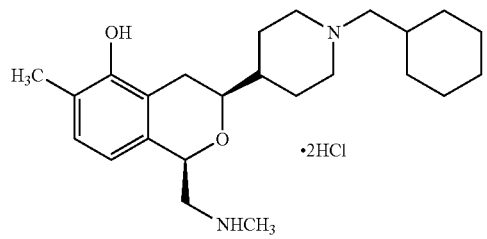

(1R,3S)-3-(1-Cyclohexylmethyl-piperidin-4-yl)-6-methyl-1-methylaminomethyl-isochroman-5-ol dihydrochloride

| Reactant | Retention time $t_R$ (min) of product | CIMS (MH$^+$) of product |
|---|---|---|
| ![cyclohexanecarbaldehyde] | 2.20 | 387.4 |

Example 97

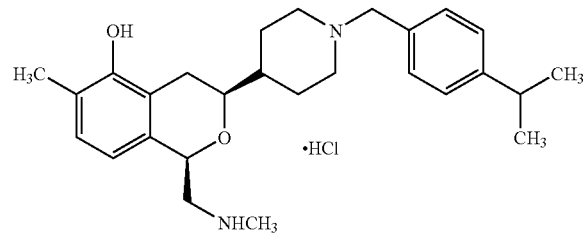

(1R,3S)-3-[1-(4-Isopropyl-benzyl)-piperidin-4-yl]-6-methyl-1-methylaminomethyl-isochroman-5-ol dihydrochloride

| Reactant | Retention time $t_R$ (min) of product | CIMS (MH$^+$) of product |
|---|---|---|
| ![4-isopropylbenzaldehyde] | 2.40 | 423.4 |

Example 98

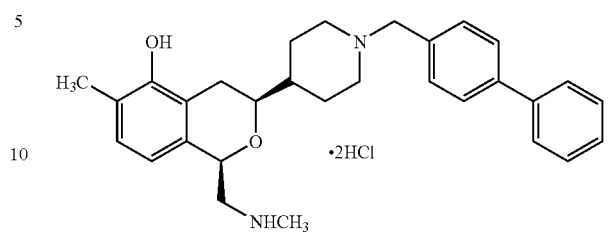

(1R,3S)-3-(1-Biphenyl-4-ylmethyl-piperidin-4-yl)-6-methyl-1-methylaminomethyl-isochroman-5-ol dihydrochloride

| Reactant | Retention time $t_R$ (min) of product | CIMS (MH$^+$) of product |
|---|---|---|
| ![biphenyl-4-carbaldehyde] | 2.44 | 457.4 |

Example 99

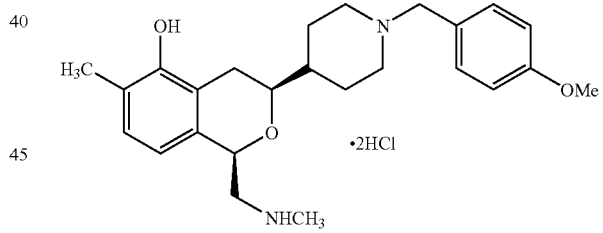

(1R,3S)-3-[1-(4-Methoxy-benzyl)-piperidin-4-yl]-6-methyl-1-methylaminomethyl-isochroman-5-ol dihydrochloride

| Reactant | Retention time $t_R$ (min) of product | CIMS (MH$^+$) of product |
|---|---|---|
| ![4-methoxybenzaldehyde] | 2.12 | 411.4 |

Example 100

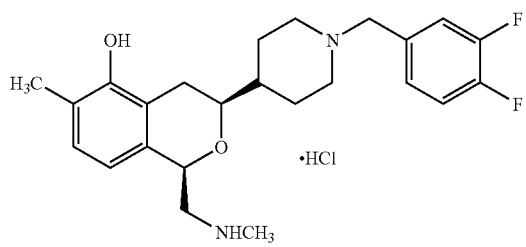

(1R,3S)-3-[1-(3,4-Difluoro-benzyl)-piperidin-4-yl]-6-methyl-1-methylaminomethyl-isochroman-5-ol dihydrochloride

| Reactant | Retention time $t_R$ (min) of product | CIMS (MH+) of product |
|---|---|---|
| 3,4-difluorobenzaldehyde | 2.15 | 417.3 |

Example 101

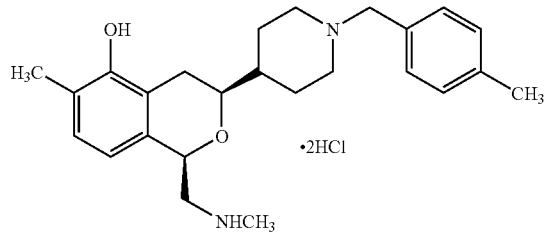

(1R,3S)-6-Methyl-1-methylaminomethyl-3-[1-(4-methyl-benzyl)-piperidin-4-yl]-isochroman-5-ol dihydrochloride

| Reactant | Retention time $t_R$ (min) of product | CIMS (MH+) of product |
|---|---|---|
| 4-methylbenzaldehyde | 2.19 | 395.4 |

Example 102

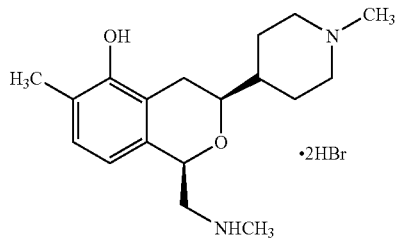

(1R,3S)-6-Methyl-1-methylaminomethyl-3-(1-methyl-piperidin-4-yl)-isochroman-5-ol dihydrobromide

| Reactant | Retention time $t_R$ (min) of product | CIMS (MH+) of product |
|---|---|---|
| HCHO | 0.98 | 305.2 |

Example 103

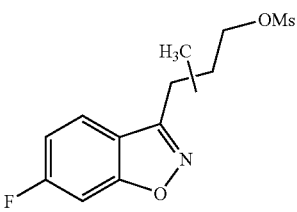

Intermediate: Methanesulfonic acid 3-(6-fluoro-benzo[d]isoxazol-3-yl)-2-methyl-propyl ester and methanesulfonic acid 3-(6-fluoro-benzo[d]isoxazol-3-yl)-butyl ester 4-(2,4-difluorophenyl)-2-methyl-4-oxobutyric acid and 4-(2,4-difluorophenyl)-3-methyl-4-oxobutyric acid Add methylsuccinic anhydride (5 g, 43.8 mmole) to a stirred suspension of 1,3-difluorobenzene (25 g, 219.1 mmole) and aluminum chloride (11.7 g, 87.6 mmole), keeping the temperature less than 50° C. Stir the reaction overnight at 50° C. and then for 3 days at 78° C. Cool to room temperature and slowly add reaction mixture to a mixture of 3N HCl (40 mL) and ice (40 g). Add methylene chloride (80 mL) and separate the organic layer, then extract the aqueous phase with additional methylene chloride (70 mL). Wash the combined organic phase twice with 1N NaOH solution (80 mL) and then acidify the combined basic wash with 6N HCl. Extract the acidic aqueous phase twice with methylene chloride (100 mL), dry over $Na_2SO_4$ and concentrate to obtain product. ESMS 229, $t_R$ (min)=1.57. $^1$H-NMR showed a 4:1 mixture of isomeric products.

3-(6-fluorobenzisoxazol-3-yl)-2-methylpropionic acid and 3-(6-fluorobenzoisoxazol-3-yl)butyric acid Stir the previous mixture (5.16 g, 27 mmole) in isopropyl alcohol (50 mL) containing K$_2$CO$_3$ (18.6 g, 135 mmole) at 45° C. Add hydroxylamine hydrochloride (4.7 g, 67.5 mmole) slowly and warm reaction to 80° C. After 2 hours cool reaction to 50° C., add additional hydroxylamine hydrochloride (2.34 g, 33.7 mmole) and warm to 80° C. overnight. Remove isopropyl alcohol by evaporation and add 2N HCl (50 mL) and ethyl acetate (50 mL). Separate the organic phase and extract the aqueous phase an additional two times with ethyl acetate (50 mL). Combine the organic layers, wash with brine, dry over Na$_2$SO$_4$ and concentrate to obtain product. ESMS 224, $t_R$ (min)=1.56. $^1$H-NMR showed a 4:1 mixture of isomeric products.

3-(6-fluorobenzisoxazol-3-yl)-2-methylpropan-1-ol and 3-(6-fluorobenzisoxazol-3-yl)butan-1-ol Dissolve the previous mixture (6.0 g, 27 mmole) in THF (100 mL) and add 1M Borane-THF (34 mL, 34 mmole). After 1 hour add methanol (15 mL) and stir overnight. Remove the solvents by evaporation and add ethyl acetate (50 mL) and 1N HCl (40 mL). Remove the organic phase, wash with saturated NaHCO$_3$ solution, dry over Na$_2$SO$_4$ and concentrate. Purify the crude product on a 30 g silica gel column (eluting with ethyl acetate:heptate 1:1). Collect the appropriate fractions and concentrate to obtain the title compound. CIMS 210, $t_R$ (min)=1.55. $^1$H-NMR showed a 1.4:1 mixture of isomeric products.

Methanesulfonic acid 3-(6-fluorobenzisoxazol-3-yl)-2-methylpropyl ester and methanesulfonic acid 3-(6-fluorobenzisoxazol-3-yl)butyl ester Dissolve the previous mixture (448 mg, 2.14 mmole) in methylene chloride (2 mL) under nitrogen atmosphere and cool to 0° C. Stir and add triethylamine (388 uL, 2.78 mmole) followed by methanesulfonyl chloride (200 uL, 2.57 mmole). After 1 hour add additional triethylamine (194 uL, 1.4 mmole) and methanesulfonyl chloride (100 uL, 1.3 mmole). After 30 minutes add 1N HCl (5 mL) and methylene chloride (5 mL) and separate the organic phase. Dry over Na$^2$SO$_4$ and concentrate to get product that is used in the next step without further purification.

Example 104 and Example 105

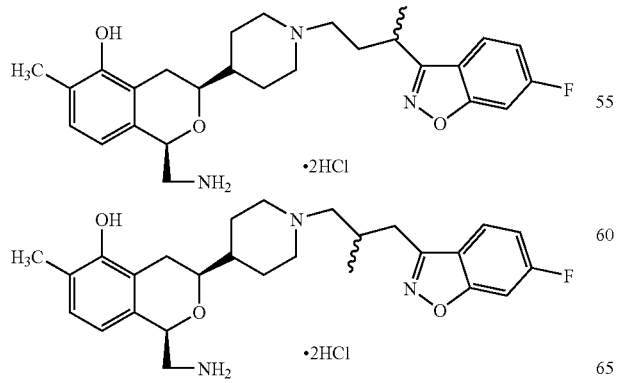

(1R,3S)-1-Aminomethyl-3-{1-[3-(6-fluoro-benzo[d]isoxazol-3-yl)butyl]piperidin-4-yl}-6-methylisochroman-5-ol dihydrochloride (Example 104) and (1R,3S)-1-aminomethyl-3-{1-[3-(6-fluoro-benzo[d]isoxazol-3-yl)-2-methylpropyl]piperidin-4-yl}-6-methyl-isochroman-5-ol dihydrochloride (Example 105)

Scheme B', step B1' N-((1R,3S)-3-{1-[3-(6-fluorobenzisoxazol-3-yl)-2-methylpropyl]piperidin-4-yl}-5-methoxy-6-methyl-isochroman-1-ylmethyl)formamide and N-((1R,3S)-3-{1-[3-(6-fluoro-benzisoxazol-3-yl)-butyl]piperidin-4-yl}-5-methoxy-6-methyl-isochroman-1-ylmethyl)formamide Dissolve the previous mixture of mesylates (507 mg, 1.76 mmole) in THF (6 mL) with N-((1R,3S)-5-methoxy-6-methyl-3-piperidin-4-yl-isochroman-1-ylmethyl)formamide (600 mg, 1.9 mmole) and K$_2$CO$_3$ (253 mg, 1.83 mmole) and stir for 72 hours at 65° C. Add 10 mL of THF and 2 mL of methanol, filter through celite, concentrate and used in the next step without further purification.

Scheme B', step B2' (1R,3S)-1-aminomethyl-3-{1-[3-(6-fluoro-benzo[d]isoxazol-3-yl)butyl]piperidin-4-yl}-6-methylisochroman-5-ol dihydrochloride and (1R,3S)-1-aminomethyl-3-{1-[3-(6-fluoro-benzo[d]isoxazol-3-yl)-2-methylpropyl]piperidin-4-yl}-6-methyl-isochroman-5-ol dihydrochloride Dissolve the previous mixture (338 mg, 0.66 mmole) in 48% HBr (2.5 mL) and heat to 100° C. Evaporate, add 15% NaOH (2 mL), methanol (2 mL) and ethyl acetate (5 mL), and stir for 2 hours. Separate the organic layer and extracted the aqueous phase with ethyl acetate (3×5 mL). Combine the organic layers, dry (MgSO$_4$), concentrate and chromatograph the mixture over a silica gel column (10 g), eluting with methanolic ammonia in methylene chloride (increasing in concentration from 1% to 10%. The appropriate fractions were combined corresponding to the two positional isomers and converted to dihydrochlorides with 2M HCl in diethyl ether to give the respective title compounds. CIMS 468.3, $t_R$ (min)=1.14 and CIMS 468.3, $t_R$ (min)=1.15.

The following examples 106-110 were synthesized similarly to Example 104 with different alkylating agents used in the first step.

Example 106

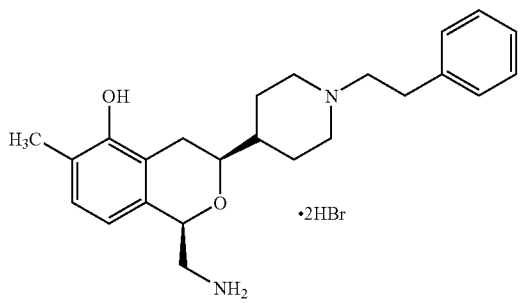

161

(1R,3S)-1-Aminomethyl-6-methyl-3-(1-phenethyl-piperidin-4-yl)-isochroman-5-ol dihydrobromide

| Alkylating Agent | Retention time $t_R$ (min) of product | CIMS (MH$^+$) of product |
|---|---|---|
| (PhCH$_2$CH$_2$Br) | 1.33 | 381.3 |

Example 107

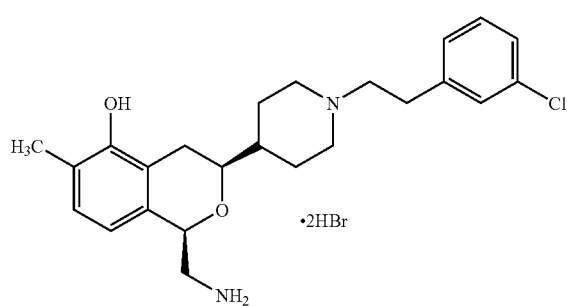

(1R,3S)-1-Aminomethyl-3-{1-[2-(3-chloro-phenyl)-ethyl]-piperidin-4-yl}-6-methyl-isochroman-5-ol dihydrobromide

| Alkylating Agent | Retention time $t_R$ (min) of product | CIMS (MH$^+$) of product |
|---|---|---|
| (MsO-CH$_2$CH$_2$-C$_6$H$_4$-Cl) | 1.5 | 415.2 |

Example 108

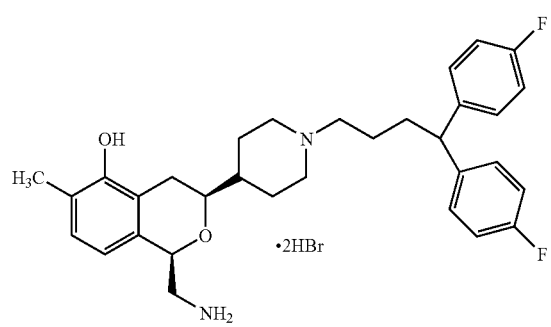

162

(1R,3S)-1-Aminomethyl-3-{1-[4,4-bis-(4-fluoro-phenyl)-butyl]-piperidin-4-yl}-6-methyl-isochroman-5-ol dihydrobromide

| Alkylating Agent | Retention time $t_R$ (min) of product | CIMS (MH$^+$) of product |
|---|---|---|
| (MsO(CH$_2$)$_3$CH(4-F-C$_6$H$_4$)$_2$) | 1.86 | 521.3 |

Example 109

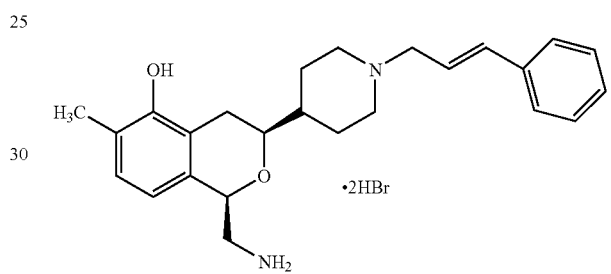

(1R,3S)-1-Aminomethyl-6-methyl-3-[1-(3-phenyl-allyl)-piperidin-4-yl]-isochroman-5-ol dihydrobromide

| Alkylating Agent | Retention time $t_R$ (min) of product | CIMS (MH$^+$) of product |
|---|---|---|
| (cinnamyl bromide) | 1.17 | 393.2 |

Example 110

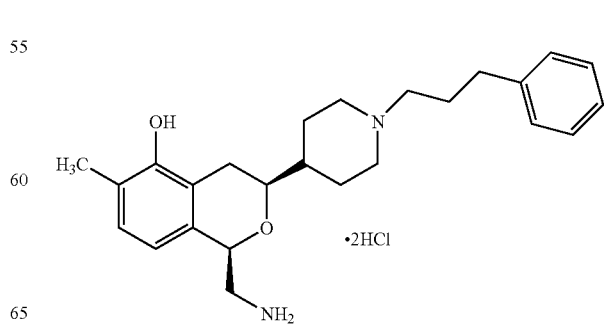

(1R,3S)-1-Aminomethyl-6-methyl-3-[1-(3-phenyl-propyl)-piperidin-4-yl]-isochroman-5-ol dihydrochloride

| Alkylating Agent | Retention time $t_R$ (min) of product | CIMS (MH⁺) of product |
|---|---|---|
| ![Br-CH2CH2CH2-Ph] | 2.49 | 395.2 |

Example 111

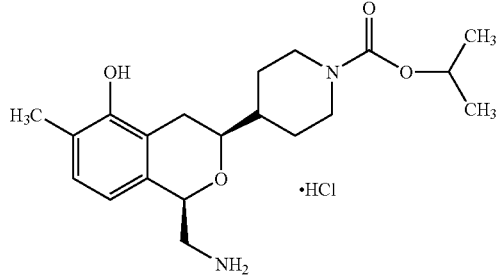

4-((1R,3S)-1-Aminomethyl-5-hydroxy-6-methyl-isochroman-3-yl)-piperidine-1-carboxylic acid isopropyl ester hydrochloride Scheme C, Step C1: 4-((1R,3S)-1-Formylminomethyl-5-isopropoxy-6-methyl-isochroman-3-yl)-piperidine-1-carboxylic acid isopropyl ester To a solution of N-((1R,3S)-5-isopropoxy-6-methyl-3-(4-piperidinyl)-1-isochromanylmethyl)formamide (Example 11, 0.58 mmol) in dichloromethane (4 mL), add DIEA (0.58 mmol), followed by of isopropyl chloroformate (0.64 mmol). Stir the reaction mixture at room temperature overnight. Evaporate the solvent and purify the resulting residue by chromatography on a 2 g silica gel column (eluted by 3% methanol in dichloromethane). Collect the appropriate fractions, concentrate and obtain the title compound.

Scheme C Steps C2, C3: 4-((1R,3S)-1-Aminomethyl-5-hydroxy-6-methyl-isochroman-3-yl)-piperidine-1-carboxylic acid isopropyl ester hydrochloride Stir a solution of 4-((1R,3S)-1-formylaminomethyl-5-isopropoxy-6-methyl-isochroman-3-yl)-piperidine-1-carboxylic acid isopropyl ester directly from the previous step in of 5% methanolic hydrochloric acid (4 mL) at room temperature for 2 days. Remove the solvent to give yellow oil. Purify the oil on a 2 g SCX column. The resulting residue was redissolved in 4 mL of anhydrous dichloromethane, cooled to −20° C., and 6 equivalents of BCl₃ (using 1M BCl₃ in dichloromethane) was added slowly into the solution. After the addition, the reaction mixture was stirred at −20° C. for 2 hours and 0° C. for 1 hour. It was then cooled to −20° C. and quenched with 0.5 mL anhydrous CH₃OH. The resulting solution was warmed to room temperature and concentrated. The crude product was purified by 2 g SCX column, followed by 1 g silica gel column (eluted by 7N NH₃ in methanol:ethyl acetate=1:10) and the hydrochloride was formed with 2M HCl in diethyl ether. CIMS 363.2 (MH⁺), $t_R$ (min)=2.65.

The following examples 111-167 were synthesized similarly to Example with different haloformates, sulfonyl halides, sulfamoyl halides, acid halides, carbamoyl halides and isocyanates used as reactants in first step.

Example 112

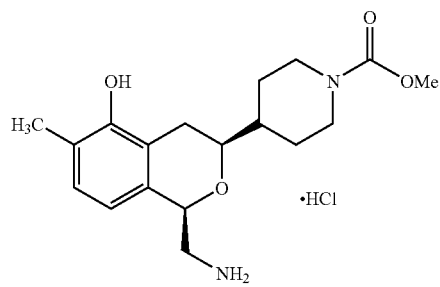

4-((1R,3S)-1-Aminomethyl-5-hydroxy-6-methyl-isochroman-3-yl)-piperidine-1-carboxylic acid methyl ester hydrochloride

| Reactant | Retention time $t_R$ (min) of product | CIMS (MH⁺) of product |
|---|---|---|
| ![Cl-C(=O)-OMe] | 2.22 | 335.3 |

Example 113

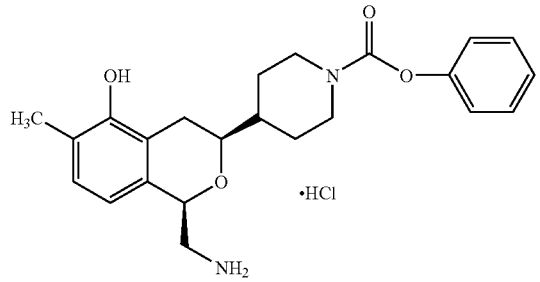

165

4-((1R,3S)-1-Aminomethyl-5-hydroxy-6-methyl-isochroman-3-yl)-piperidine-1-carboxylic acid phenyl ester hydrochloride

| Reactant | Retention time $t_R$ (min) of product | CIMS (MH$^+$) of product |
|---|---|---|
| (phenyl chloroformate) | 2.56 | 397.3 |

Example 114

4-((1R,3S)-1-Aminomethyl-5-hydroxy-6-methyl-isochroman-3-yl)-piperidine-1-carboxylic acid p-tolyl ester hydrochloride

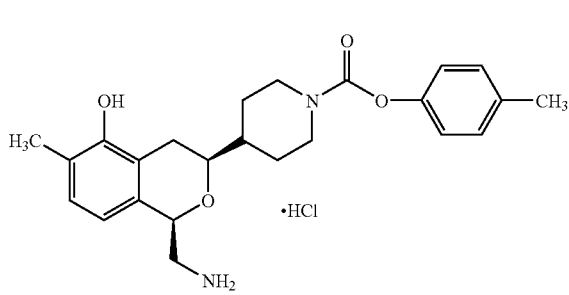

| Reactant | Retention time $t_R$ (min) of product | CIMS (MH$^+$) of product |
|---|---|---|
| (p-tolyl chloroformate) | 2.67 | 411.3 |

Example 115

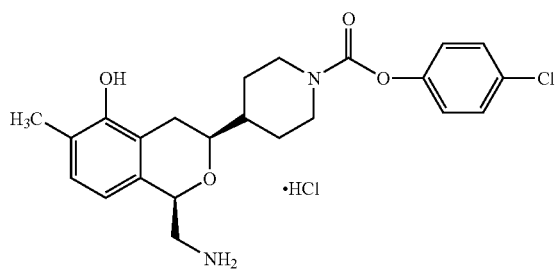

166

4-((1R,3S)-1-Aminomethyl-5-hydroxy-6-methyl-isochroman-3-yl)-piperidine-1-carboxylic acid 4-chloro-phenyl ester hydrochloride

| Reactant | Retention time $t_R$ (min) of product | CIMS (MH$^+$) of product |
|---|---|---|
| (4-chlorophenyl chloroformate) | 2.67 | 411.3 |

Example 116

4-((1R,3S)-1-Aminomethyl-5-hydroxy-6-methyl-isochroman-3-yl)-piperidine-1-carboxylic acid 2-chloro-phenyl ester hydrochloride

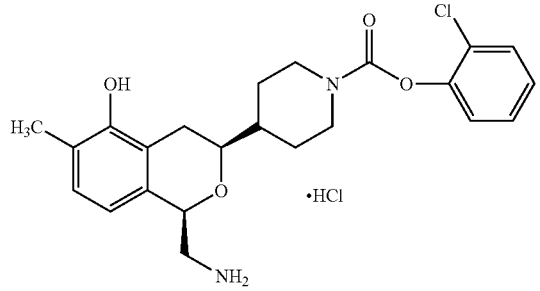

| Reactant | Retention time $t_R$ (min) of product | CIMS (MH$^+$) of product |
|---|---|---|
| (2-chlorophenyl chloroformate) | 2.74 | 431.3 |

Example 117

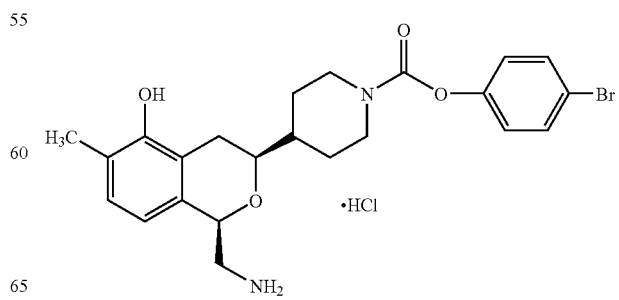

167

4-((1R,3S)-1-Aminomethyl-5-hydroxy-6-methyl-isochroman-3-yl)-piperidine-1-carboxylic acid 4-bromo-phenyl ester hydrochloride

| Reactant | Retention time $t_R$ (min) of product | CIMS (MH$^+$) of product |
|---|---|---|
| 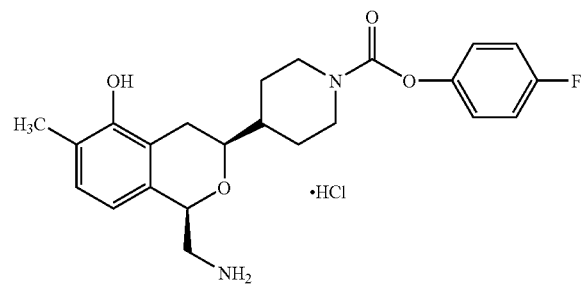 | 2.77 | 475.2 |

Example 118

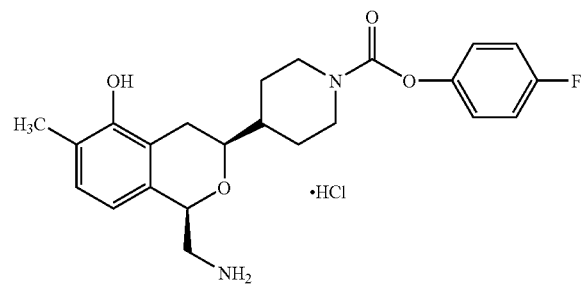

4-((1R,3S)-1-Aminomethyl-5-hydroxy-6-methyl-isochroman-3-yl)-piperidine-1-carboxylic acid 4-fluoro-phenyl ester hydrochloride

| Reactant | Retention time $t_R$ (min) of product | CIMS (MH$^+$) of product |
|---|---|---|
| 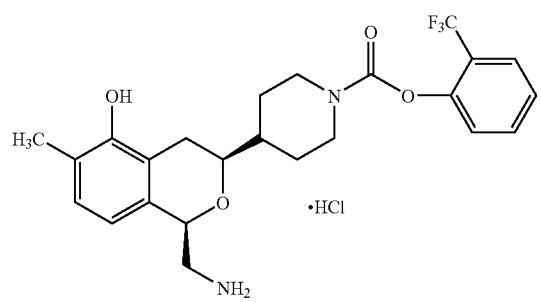 | 2.60 | 415.3 |

Example 119

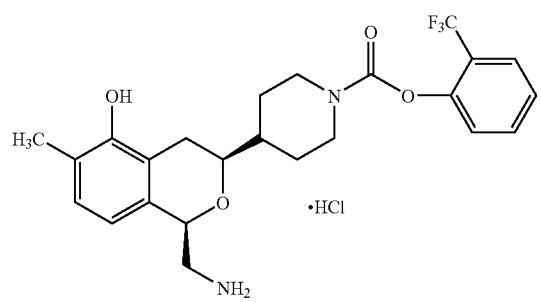

168

4-((1R,3S)-1-Aminomethyl-5-hydroxy-6-methyl-isochroman-3-yl)-piperidine-1-carboxylic acid 2-trifluoromethyl-phenyl ester hydrochloride

| Reactant | Retention time $t_R$ (min) of product | CIMS (MH$^+$) of product |
|---|---|---|
| 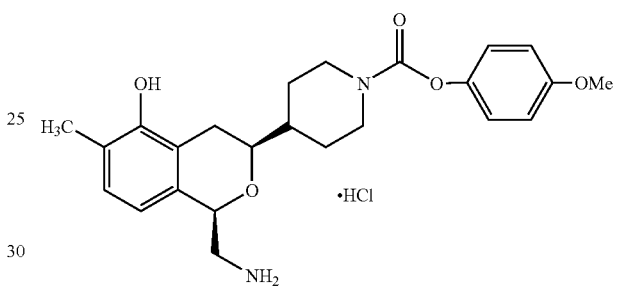 | 2.80 | 465.3 |

Example 120

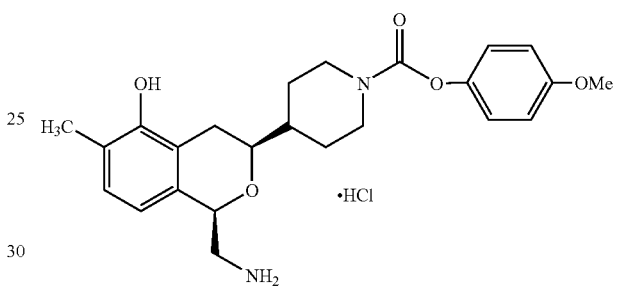

4-((1R,3S)-1-Aminomethyl-5-hydroxy-6-methyl-isochroman-3-yl)-piperidine-1-carboxylic acid 4-methoxy-phenyl ester hydrochloride

| Reactant | Retention time $t_R$ (min) of product | CIMS (MH$^+$) of product |
|---|---|---|
| 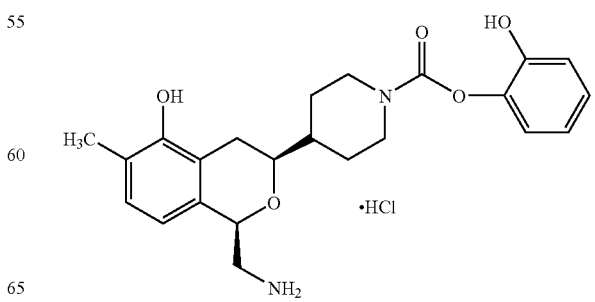 | 2.55 | 427.3 |

Example 121

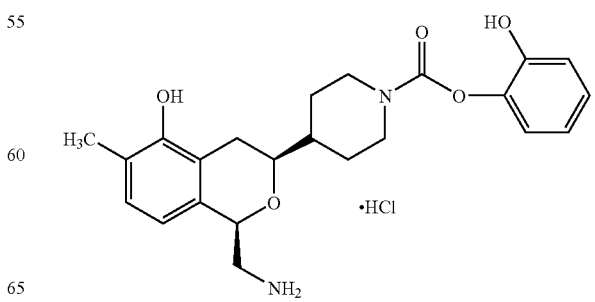

4-((1R,3S)-1-Aminomethyl-5-hydroxy-6-methyl-isochroman-3-yl)-piperidine-1-carboxylic acid 2-hydroxy-phenyl ester hydrochloride

| Reactant | Retention time $t_R$ (min) of product | CIMS (MH$^+$) of product |
|---|---|---|
| 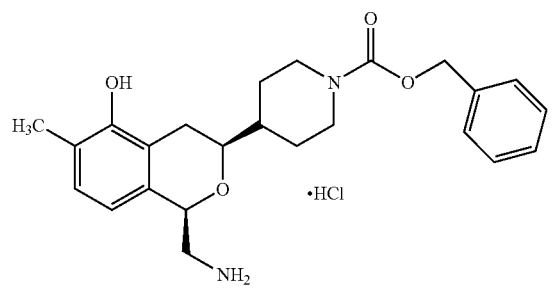 | 2.39 | 413.3 |

Example 122

4-((1R,3S)-1-Aminomethyl-5-hydroxy-6-methyl-isochroman-3-yl)-piperidine-1-carboxylic acid benzyl ester hydrochloride

| Reactant | Retention time $t_R$ (min) of product | CIMS (MH$^+$) of product |
|---|---|---|
| | 2.63 | 411.3 |

Example 123

4-((1R,3S)-1-Aminomethyl-5-hydroxy-6-methyl-isochroman-3-yl)-piperidine-1-carboxylic acid naphthalen-2-yl ester hydrochloride

| Reactant | Retention time $t_R$ (min) of product | CIMS (MH$^+$) of product |
|---|---|---|
| 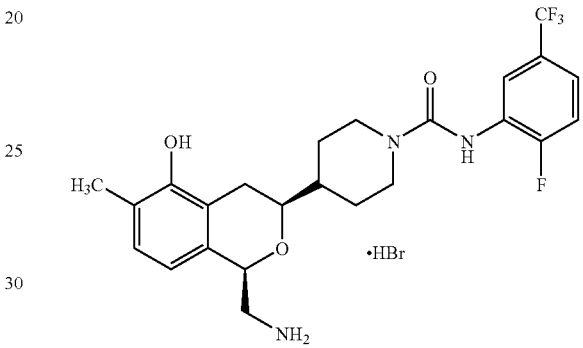 | 2.80 | 447.3 |

Example 124

4-((1R,3S)-1-Aminomethyl-5-hydroxy-6-methyl-isochroman-3-yl)-piperidine-1-carboxylic acid (2-fluoro-5-trifluoromethyl-phenyl)-amide hydrobromide

| Reactant | Retention time $t_R$ (min) of product | CIMS (MH$^+$) of product |
|---|---|---|
| | 1.42 | 482.3 |

Example 125

171

4-((1R,3S)-1-Aminomethyl-5-hydroxy-6-methyl-isochroman-3-yl)-piperidine-1-carboxylic acid (3-methoxy-phenyl)-amide

| Reactant | Retention time $t_R$ (min) of product | CIMS (MH$^+$) of product |
|---|---|---|
| 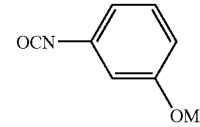 | 2.79 | 426.0 |

Example 126

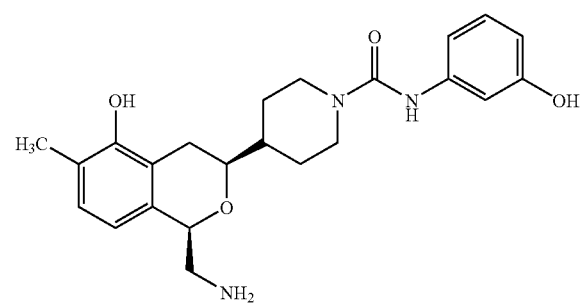

4-((1R,3S)-1-Aminomethyl-5-hydroxy-6-methyl-isochroman-3-yl)-piperidine-1-carboxylic acid (3-hydroxy-phenyl)-amide

| Reactant | Retention time $t_R$ (min) of product | CIMS (MH$^+$) of product |
|---|---|---|
| 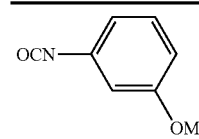 | 2.57 | 412.2 |

Example 127

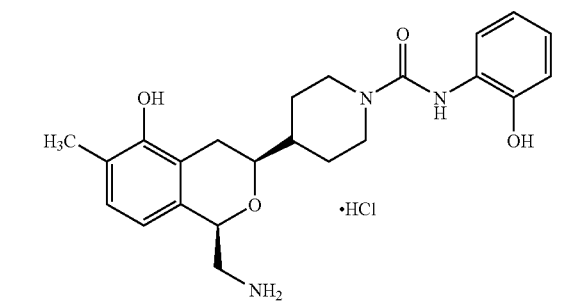

172

4-((1R,3S)-1-Aminomethyl-5-hydroxy-6-methyl-isochroman-3-yl)-piperidine-1-carboxylic acid (2-hydroxy-phenyl)-amide hydrochloride

| Reactant | Retention time $t_R$ (min) of product | CIMS (MH$^+$) of product |
|---|---|---|
| 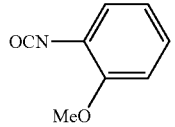 | 2.65 | 412.2 |

Example 128

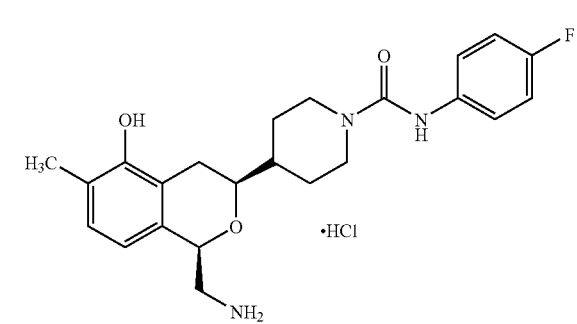

4-((1R,3S)-1-Aminomethyl-5-hydroxy-6-methyl-isochroman-3-yl)-piperidine-1-carboxylic acid (4-fluoro-phenyl)-amide hydrochloride

| Reactant | Retention time $t_R$ (min) of product | CIMS (MH$^+$) of product |
|---|---|---|
| 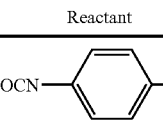 | 2.80 | 414.1 |

Example 129

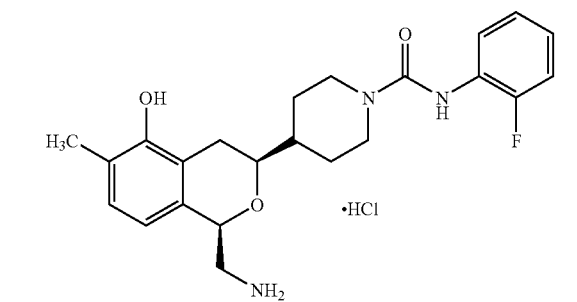

Example 130

4-((1R,3S)-1-Aminomethyl-5-hydroxy-6-methyl-isochroman-3-yl)-piperidine-1-carboxylic acid (2-fluoro-phenyl)-amide hydrochloride

| Reactant | Retention time $t_R$ (min) of product | CIMS (MH⁺) of product |
|---|---|---|
| OCN—⟨2-F-phenyl⟩ | 2.75 | 414.2 |

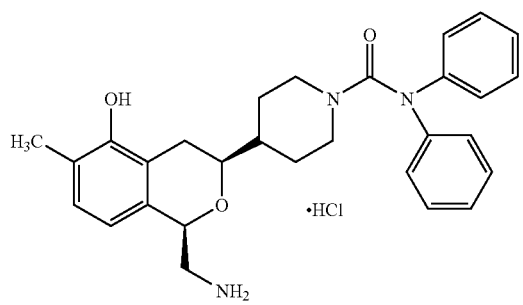

4-((1R,3S)-1-Aminomethyl-5-hydroxy-6-methyl-isochroman-3-yl)-piperidine-1-carboxylic acid diphenylamide hydrochloride

| Reactant | Retention time $t_R$ (min) of product | CIMS (MH⁺) of product |
|---|---|---|
| ClC(O)N(Ph)₂ | 3.04 | 472.3 |

Example 131

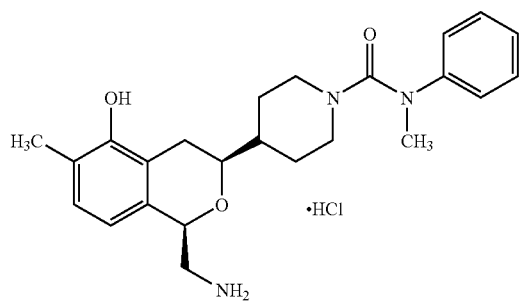

Example 132

4-((1R,3S)-1-Aminomethyl-5-hydroxy-6-methyl-isochroman-3-yl)-piperidine-1-carboxylic acid methyl-phenyl-amide hydrochloride

| Reactant | Retention time $t_R$ (min) of product | CIMS (MH⁺) of product |
|---|---|---|
| ClC(O)N(CH₃)Ph | 2.63 | 410.2 |

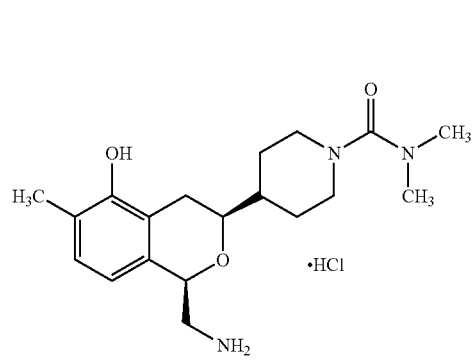

4-((1R,3S)-1-Aminomethyl-5-hydroxy-6-methyl-isochroman-3-yl)-piperidine-1-carboxylic acid dimethylamide hydrochloride

| Reactant | Retention time $t_R$ (min) of product | CIMS (MH⁺) of product |
|---|---|---|
| ClC(O)N(CH₃)₂ | 2.15 | 348.3 |

Example 133

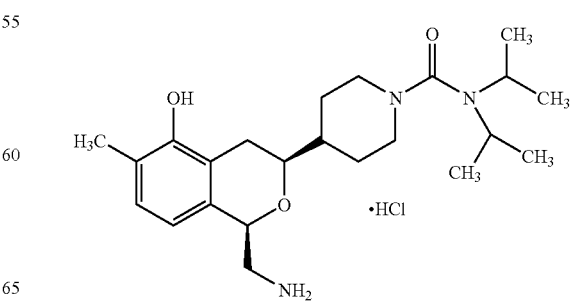

175

4-((1R,3S)-1-Aminomethyl-5-hydroxy-6-methyl-isochroman-3-yl)-piperidine-1-carboxylic acid diisopropylamide hydrochloride

| Reactant | Retention time $t_R$ (min) of product | CIMS (MH$^+$) of product |
|---|---|---|
| (structure) | 2.62 | 404.4 |

Example 134

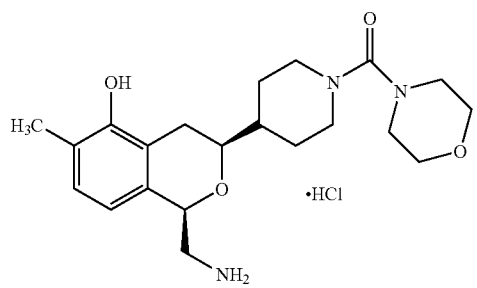

[4-((1R,3S)-1-Aminomethyl-5-hydroxy-6-methyl-isochroman-3-yl)-piperidin-1-yl]-morpholin-4-yl-methanone hydrochloride

| Reactant | Retention time $t_R$ (min) of product | CIMS (MH$^+$) of product |
|---|---|---|
| (structure) | 2.10 | 390.3 |

Example 135

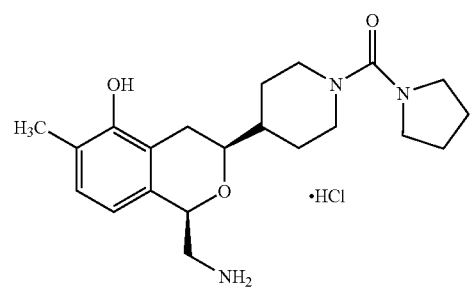

176

[4-((1R,3S)-1-Aminomethyl-5-hydroxy-6-methyl-isochroman-3-yl)-piperidin-1-yl]-pyrrolidin-1-yl-methanone hydrochloride

| Reactant | Retention time $t_R$ (min) of product | CIMS (MH$^+$) of product |
|---|---|---|
| (structure) | 2.27 | 374.3 |

Example 136

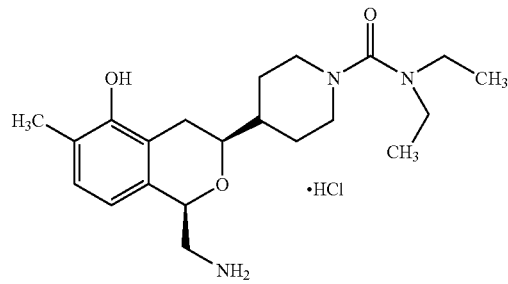

4-((1R,3S)-1-Aminomethyl-5-hydroxy-6-methyl-isochroman-3-yl)-piperidine-1-carboxylic acid diethylamide hydrochloride

| Reactant | Retention time $t_R$ (min) of product | CIMS (MH$^+$) of product |
|---|---|---|
| (structure) | 2.37 | 376.3 |

Example 137

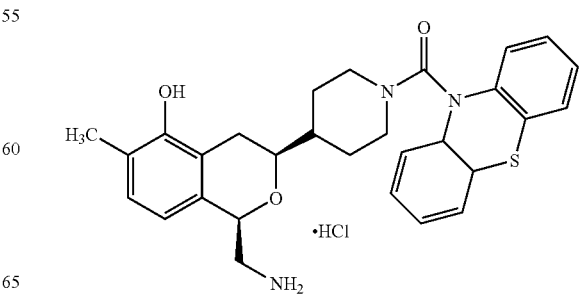

Example 138

[4-((1R,3S)-1-Aminomethyl-5-hydroxy-6-methyl-isochroman-3-yl)-piperidin-1-yl]-phenothiazin-10-yl-methanone hydrochloride

| Reactant | Retention time $t_R$ (min) of product | CIMS (MH$^+$) of product |
|---|---|---|
| 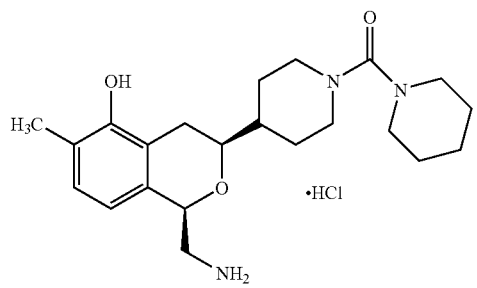 | 2.97 | 502.3 |

Example 139

[4-((1R,3S)-1-Aminomethyl-5-hydroxy-6-methyl-isochroman-3-yl)-piperidin-1-yl]-piperidin-1-yl-methanone hydrochloride

| Reactant | Retention time $t_R$ (min) of product | CIMS (MH$^+$) of product |
|---|---|---|
| 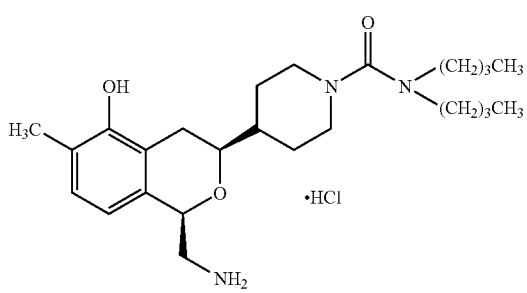 | 2.40 | 388.3 |

Example 140

4-((1R,3S)-1-Aminomethyl-5-hydroxy-6-methyl-isochroman-3-yl)-piperidine-1-carboxylic acid dibutylamide hydrochloride

| Reactant | Retention time $t_R$ (min) of product | CIMS (MH$^+$) of product |
|---|---|---|
| 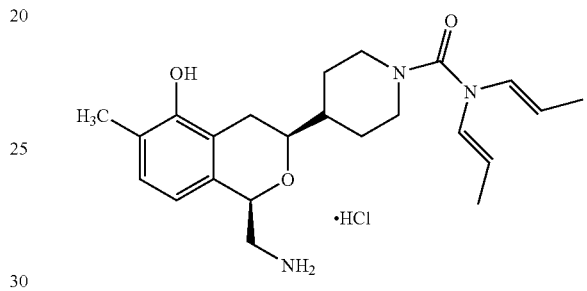 | 2.87 | 432.4 |

Example 141

4-((1R,3S)-1-Aminomethyl-5-hydroxy-6-methyl-isochroman-3-yl)-piperidine-1-carboxylic acid diallylamide hydrochloride

| Reactant | Retention time $t_R$ (min) of product | CIMS (MH$^+$) of product |
|---|---|---|
| 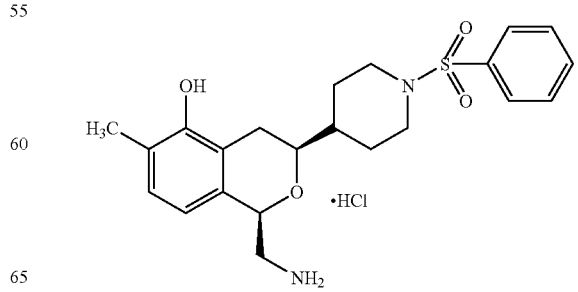 | 2.54 | 400.3 |

179

(1R,3S)-1-Aminomethyl-3-(1-benzenesulfonyl-piperidin-4-yl)-6-methyl-isochroman-5-ol hydrochloride

| Reactant | Retention time $t_R$ (min) of product | CIMS (MH$^+$) of product |
|---|---|---|
| ![phenyl-SO2Cl] | 2.89 | 417.2 |

Example 142

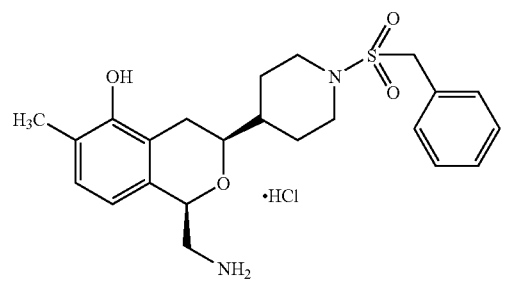

(1R,3S)-1-Aminomethyl-6-methyl-3-(1-phenylmethanesulfonyl-piperidin-4-yl)-isochroman-5-ol hydrochloride

| Reactant | Retention time $t_R$ (min) of product | CIMS (MH$^+$) of product |
|---|---|---|
| benzyl-SO₂Cl | 2.62 | 431.5 |

Example 143

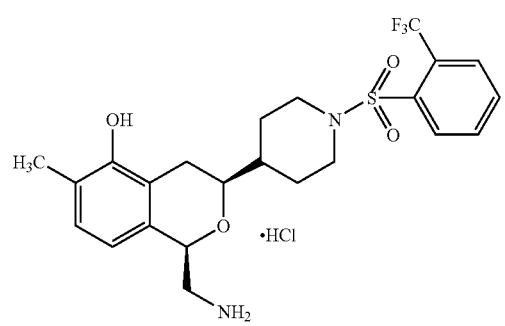

180

(1R,3S)-1-Aminomethyl-6-methyl-3-[1-(2-trifluoromethyl-benzenesulfonyl)-piperidin-4-yl]-isochroman-5-ol hydrochloride

| Reactant | Retention time $t_R$ (min) of product | CIMS (MH$^+$) of product |
|---|---|---|
| 2-CF₃-phenyl-SO₂Cl | 2.74 | 485.5 |

Example 144

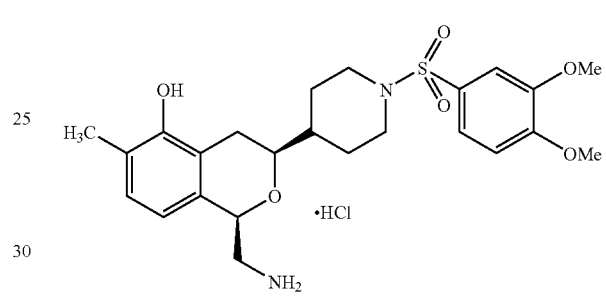

(1R,3S)-1-Aminomethyl-3-[1-(3,4-dimethoxy-benzenesulfonyl)-piperidin-4-yl]-6-methyl-isochroman-5-ol hydrochloride

| Reactant | Retention time $t_R$ (min) of product | CIMS (MH$^+$) of product |
|---|---|---|
| 3,4-(MeO)₂-phenyl-SO₂Cl | 2.54 | 477.5 |

Example 145

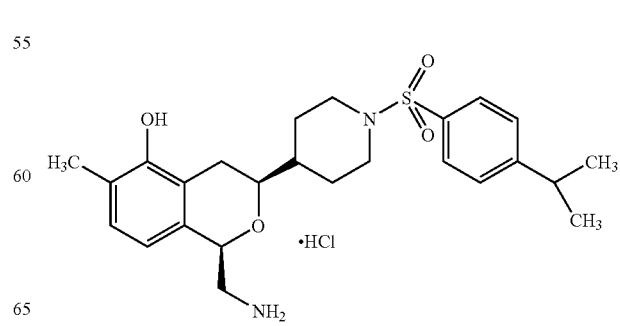

181

(1R,3S)-1-Aminomethyl-3-[1-(4-isopropyl-benzene-sulfonyl)-piperidin-4-yl]-6-methyl-isochroman-5-ol hydrochloride

| Reactant | Retention time $t_R$ (min) of product | CIMS (MH$^+$) of product |
|---|---|---|
| H₃C-CH(CH₃)-C₆H₄-SO₂Cl | 2.90 | 459.5 |

Example 146

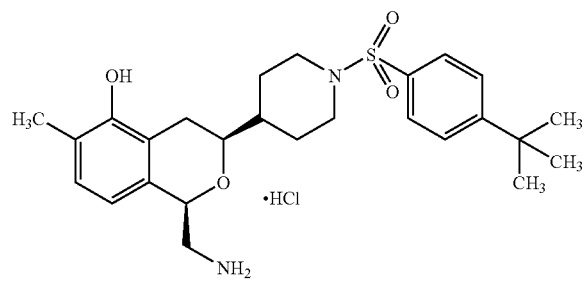

(1R,3S)-1-Aminomethyl-3-[1-(4-tert-butyl-benzene-sulfonyl)-piperidin-4-yl]-6-methyl-isochroman-5-ol hydrochloride

| Reactant | Retention time $t_R$ (min) of product | CIMS (MH$^+$) of product |
|---|---|---|
| (H₃C)₃C-C₆H₄-SO₂Cl | 2.97 | 473.6 |

Example 147

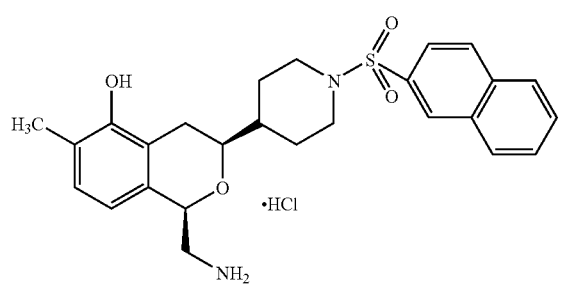

182

(1R 3S)-1-Aminomethyl-6-methyl-3-[1-(naphthalene-2-sulfonyl)-piperidin-4-yl]-isochroman-5-ol hydrochloride

| Reactant | Retention time $t_R$ (min) of product | CIMS (MH$^+$) of product |
|---|---|---|
| naphthalene-SO₂Cl | 2.82 | 467.5 |

Example 148

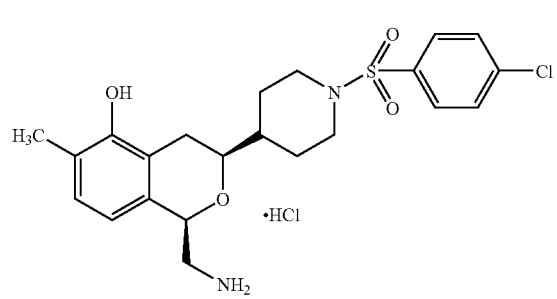

(1R,3S)-1-Aminomethyl-3-[1-(4-chloro-benzene-sulfonyl)-piperidin-4-yl]-6-methyl-isochroman-5-ol hydrochloride

| Reactant | Retention time $t_R$ (min) of product | CIMS (MH$^+$) of product |
|---|---|---|
| Cl-C₆H₄-SO₂Cl | 2.74 | 451.3 |

Example 149

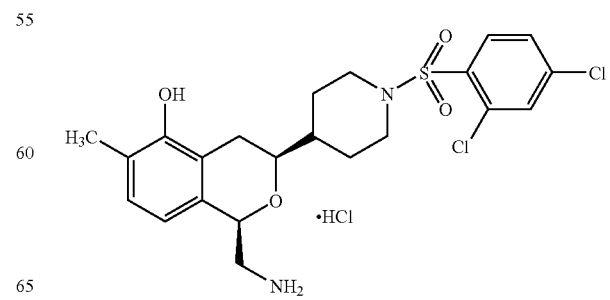

183

(1R,3S)-1-Aminomethyl-3-[1-(2,4-dichloro-benzenesulfonyl)-piperidin-4-yl]-6-methyl-isochroman-5-ol hydrochloride

| Reactant | Retention time $t_R$ (min) of product | CIMS (MH⁺) of product |
|---|---|---|
| | 2.84 | 485.3 |

Example 150

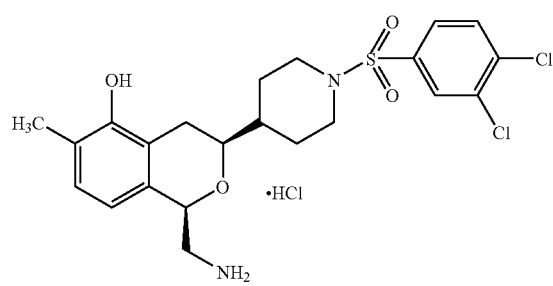

(1R,3S)-1-Aminomethyl-3-[1-(3,4-dichloro-benzenesulfonyl)-piperidin-4-yl]-6-methyl-isochroman-5-ol hydrochloride

| Reactant | Retention time $t_R$ (min) of product | CIMS (MH⁺) of product |
|---|---|---|
| | 2.88 | 485.3 |

Example 151

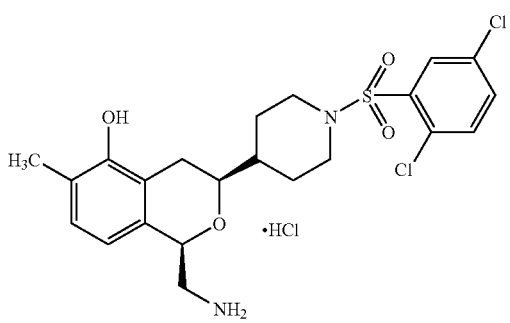

184

(1R,3S)-1-Aminomethyl-3-[1-(2,5-dichloro-benzenesulfonyl)-piperidin-4-yl]-6-methyl-isochroman-5-ol hydrochloride

| Reactant | Retention time $t_R$ (min) of product | CIMS (MH⁺) of product |
|---|---|---|
| | 2.82 | 485.3 |

Example 152

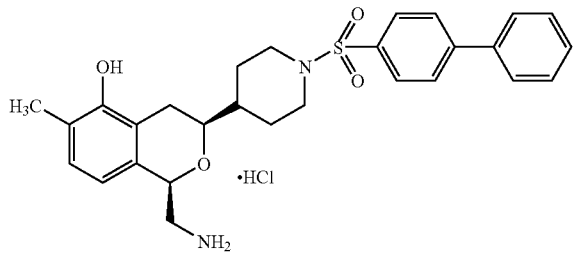

(1R,3S)-1-Aminomethyl-3-[1-(biphenyl-4-sulfonyl)-piperidin-4-yl]-6-methyl-isochroman-5-ol hydrochloride

| Reactant | Retention time $t_R$ (min) of product | CIMS (MH⁺) of product |
|---|---|---|
| | 2.94 | 493.4 |

Example 153

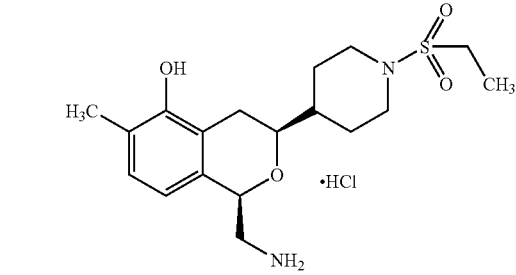

Example 154

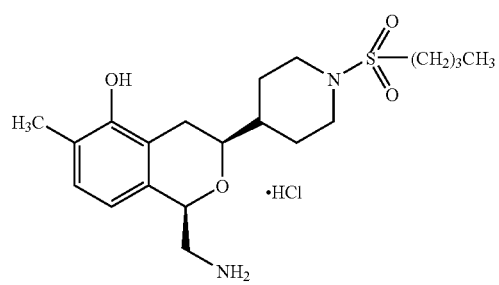

(1R,3S)-1-Aminomethyl-3-(1-ethanesulfonyl-piperidin-4-yl)-6-methyl-isochroman-5-ol hydrochloride

| Reactant | Retention time $t_R$ (min) of product | CIMS (MH⁺) of product |
|---|---|---|
| H₃C—SO₂Cl | 2.35 | 369.2 |

(1R,3S)-1-Aminomethyl-3-[1-(butane-1-sulfonyl)-piperidin-4-yl]-6-methyl-isochroman-5-ol hydrochloride

| Reactant | Retention time $t_R$ (min) of product | CIMS (MH⁺) of product |
|---|---|---|
| CH₃(CH₂)₃—SO₂Cl | 2.66 | 397.2 |

Example 155

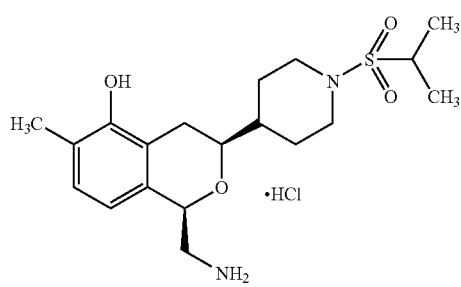

(1R,3S)-1-Aminomethyl-6-methyl-3-[1-(Propane-2-sulfonyl)-piperidin-4-yl]-isochroman-5-ol hydrochloride

| Reactant | Retention time $t_R$ (min) of product | CIMS (MH⁺) of product |
|---|---|---|
| (H₃C)₂CH—SO₂Cl | 2.47 | 383.2 |

Example 156

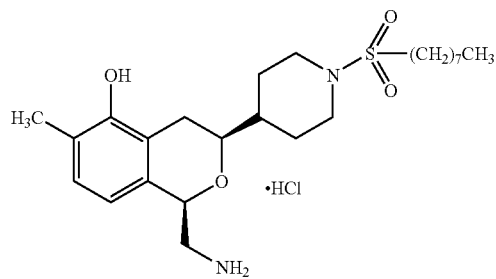

(1R,3S)-1-Aminomethyl-6-methyl-3-[1-(octane-1-sulfonyl)-piperidin-4-yl]-isochroman-5-ol hydrochloride

| Reactant | Retention time $t_R$ (min) of product | CIMS (MH⁺) of product |
|---|---|---|
| CH₃(CH₂)₇—SO₂Cl | 3.29 | 453.3 |

Example 157

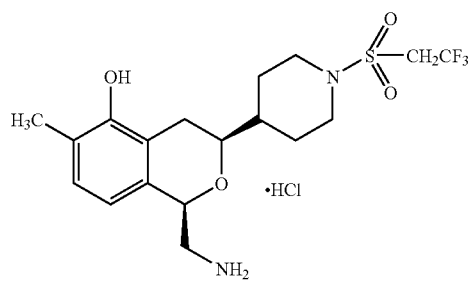

(1R,3S)-1-Aminomethyl-6-methyl-3-[1-(2,2,2-trifluoro-ethanesulfonyl)-piperidin-4-yl]-isochroman-5-ol hydrochloride

| Reactant | Retention time $t_R$ (min) of product | CIMS (MH⁺) of product |
|---|---|---|
| CF₃CH₂—SO₂Cl | 2.65 | 423.2 |

Example 158

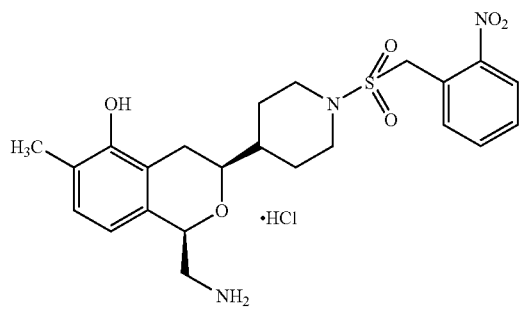

(1R,3S)-1-Aminomethyl-6-methyl-3-[1-(2-nitro-phenylmethanesulfonyl)-piperidin-4-yl]-isochroman-5-ol hydrochloride

| Reactant | Retention time $t_R$ (min) of product | CIMS (MH$^+$) of product |
|---|---|---|
| (2-nitrobenzyl SO$_2$Cl) | 2.74 | 476.2 |

Example 159

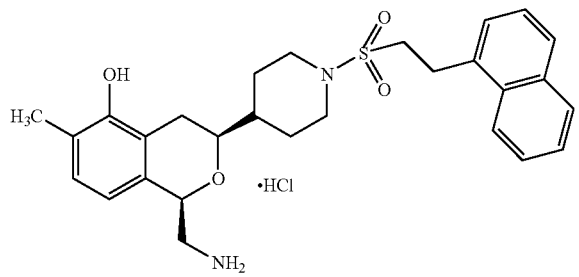

(1R,3S)-1-Aminomethyl-6-methyl-3-[1-(2-naphthalen-1-yl-ethanesulfonyl)-piperidin-4-yl]-isochroman-5-ol hydrochloride

| Reactant | Retention time $t_R$ (min) of product | CIMS (MH$^+$) of product |
|---|---|---|
| (naphthyl-ethyl SO$_2$Cl) | 3.07 | 495.3 |

Example 160

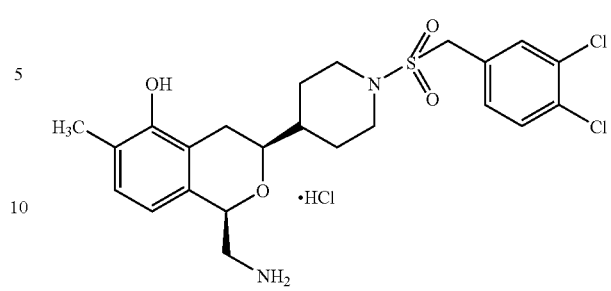

(1R,3S)-1-Aminomethyl-3-[1-(3,4-dichloro-phenyl-methanesulfonyl)-piperidin-4-yl]-6-methyl-isochroman-5-ol hydrochloride

| Reactant | Retention time $t_R$ (min) of product | CIMS (MH$^+$) of product |
|---|---|---|
| (3,4-dichlorobenzyl SO$_2$Cl) | 3.00 | 499.2 |

Example 161

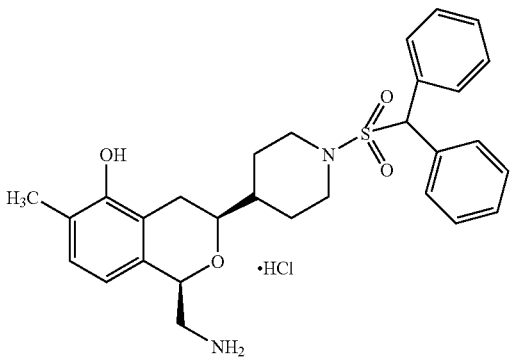

(1R,3S)-1-Aminomethyl-3-[1-(2,2-diphenyl-ethane-sulfonyl)-piperidin-4-yl]-6-methyl-isochroman-5-ol hydrochloride

| Reactant | Retention time $t_R$ (min) of product | CIMS (MH$^+$) of product |
|---|---|---|
| (diphenylmethyl SO$_2$Cl) | 3.07 | 521.2 |

Example 162

1(R)-[4-((1R,3S)-1-Aminomethyl-5-hydroxy-6-methyl-isochroman-3-yl)-piperidine-1-sulfonylmethyl]-7,7-dimethyl-bicyclo[2.2.1]heptan-2-one hydrochloride

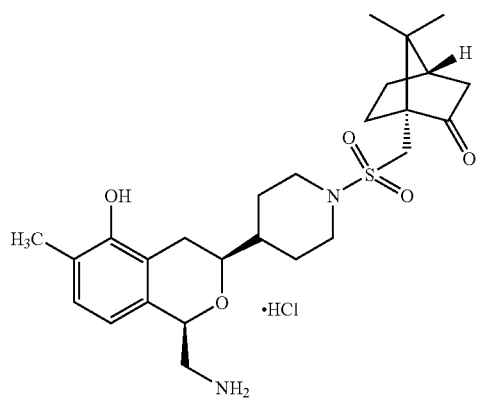

| Reactant | Retention time $t_R$ (min) of product | CIMS (MH⁺) of product |
|---|---|---|
|  | 2.79 | 491.2 |

Example 163

1(S)-[4-((1R,3S)-1-Aminomethyl-5-hydroxy-6-methyl-isochroman-3-yl)-piperidine-1-sulfonylmethyl]-7,7-dimethyl-bicyclo[2.2.1]heptan-2-one hydrochloride

| Reactant | Retention time $t_R$ (min) of product | CIMS (MH⁺) of product |
|---|---|---|
|  | 2.81 | 491.3 |

Example 164

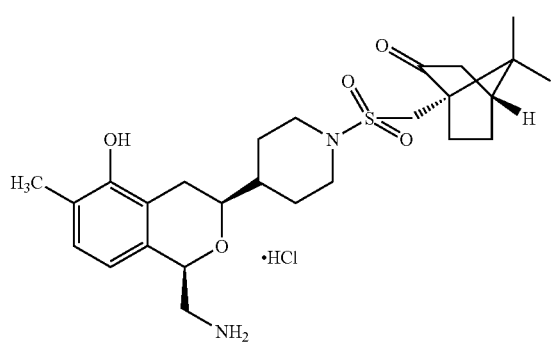

4-((1R,3S)-1-Aminomethyl-5-hydroxy-6-methyl-isochroman-3-yl)-piperidine-1-sulfonic acid dimethylamide hydrochloride

| Reactant | Retention time $t_R$ (min) of product | CIMS (MH⁺) of product |
|---|---|---|
| (CH₃)₂N—SO₂Cl | 2.49 | 384.2 |

Example 165

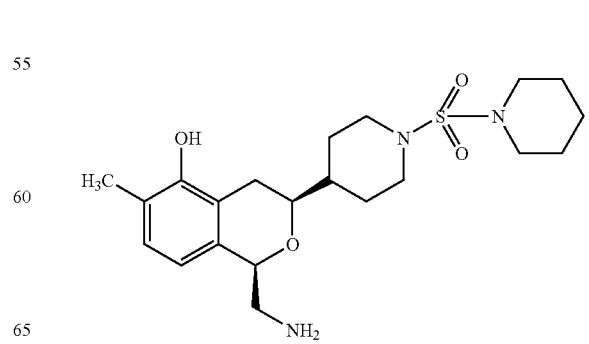

191

(1R,3S)-1-Aminomethyl-6-methyl-3-[1-(piperidine-1-sulfonyl)-piperidin-4-yl]-isochroman-5-ol hydrochloride

| Reactant | Retention time $t_R$ (min) of product | CIMS (MH$^+$) of product |
|---|---|---|
| 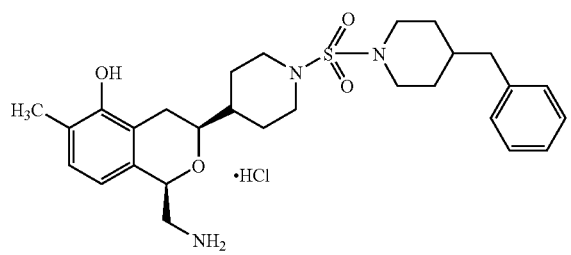 | 2.57 | 424.3 |

Example 166

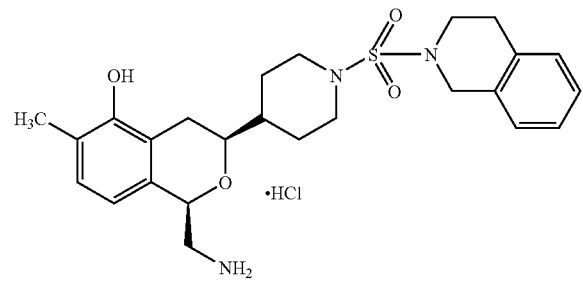

(1R,3S)-1-Aminomethyl-3-[1-(4-benzyl-piperidine-1-sulfonyl)-piperidin-4-yl]-6-methyl-isochroman-5-ol hydrochloride

| Reactant | Retention time $t_R$ (min) of product | CIMS (MH$^+$) of product |
|---|---|---|
| 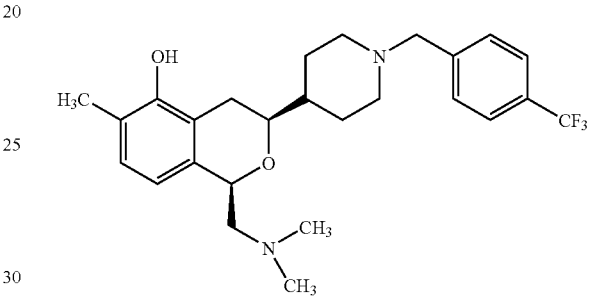 | 3.00 | 514.4 |

Example 167

192

(1R,3S)-1-Aminomethyl-3-[1-(3,4-dihydro-1H-isoquinoline-2-sulfonyl)-piperidin-yl]-6-methyl-isochroman-5-ol hydrochloride

| Reactant | Retention time $t_R$ (min) of product | CIMS (MH$^+$) of product |
|---|---|---|
| | 2.75 | 472.3 |

Example 168

(1R,3S)-1-Dimethylaminomethyl-6-methyl-i-3-[1-(4-trifluoromethylbenzyl)piperidin-4-yl]-isochroman-5-ol Scheme D, Step D1: [1-Hydroxy-2-(2-methoxy-3-methylphenyl)ethyl]piperidine-1-carboxylic acid benzyl ester Chill (5° C.) and stir a slurry of (S)-2-(2-methoxy-3-methylphenyl)-1-(4-piperidinyl)ethanol (19.8 g, 53.5 mmol) in THF (220 mL) and saturated aqueous K$_2$CO$_3$ (220 mL) and add benzyl chloroformate (7.87 mL, 53.5 mmol) dropwise. Stir the reaction mixture in the cold for 20 min and then add 200 mL of H$_2$O and 400 mL of EtOAc. Separate the organic layer and extract the aqueous layer was with EtOAc (400 mL). Wash the combined organic phase with brine, dry over Na$_2$SO$_4$ and concentrate. Purify the resulting crude product by chromatography over SiO$_2$ using EtOAc:CH$_2$Cl$_2$ (1:5). Concentration of the product-containing fractions gave 19 g (93%) of solid product; $^1$H-NMR (DMSO-d$_6$) δ 7.3-7.4 (m, 5H), 7.1-6.9 (m, 3H), 5.1 (s, 2H), 4.5 (d, 1H), 4.1-4.0 (m, 2H), 3.6 (s, 3H), 3.5 (m, 1H), 2.8-2.7 (m, 3H), 2.5 (m, 1H), 2.2 (s, 3H), 1.8 (m, 1H), 1.6 (m, 1H), 1.4 (m, 1H), 1.4-1.2 (m, 2H).

Scheme D, Step D2 REM Bound (S)-2-(2-Methoxy-3-methylphenyl)-1-(4-piperidinyl)ethanol To a solution of [1-Hydroxy-2-(2-methoxy-3-methylphenyl)ethyl]piperidine-1-carboxylic acid benzyl ester (3.43 g) in anhydrous methanol (64 mL) add 10% Pd on carbon (173 mg). Hydrogenate the reaction mixture at 55 psi of H$_2$ for 2 hours. Filter through celite and wash three times with of methanol (30 mL). Combine the filtrates and evaporate to give 2.2 g of viscous oil. Dissolve the resulting oil in NMP (18 mL)

and transfer to a shaking vessel. Add REM resin (2.0 g, 1.05 mmol/g of loading). Shake the reaction mixture at room temperature for 4 days, filter and wash the filter cake three times each with dichloromethane, methanol, and dichloromethane again. Dry the resulting resin under high vacuum overnight.

Scheme D, Step D3 Rem Bound (1R,3S)-4-(1-Bromomethyl-5-methoxy-6-methyl-isochroman-3-yl)-piperidine Keep all reagents in the refrigerator at −5° C. before using. Flush a 20 mL vial three times with argon. To this vial add REM bound (S)-2-(2-Methoxy-3-methylphenyl)-1-(4-piperidinyl)ethanol (300 mg), anhydrous toluene (9 mL), bromoacetaldehyde dimethyl acetal (89 µL), and borontrifluoride diethyl etherate (144 µL). Cap the vial and place on a shaking table for one day. Transfer the reaction mixture to a 50 mL shaking vessel, filter and wash the resin one time with toluene and twice each with dichloromethane, dioxane-0.1 N aqueous NaOH (1:1 ratio), dioxane, methanol and dichloromethane. Dry the resulting resin under high vacuum overnight.

Scheme D, Step D4 (1R,3S)-1-(4-Trifluoromethylbenzyl)-4-(1-bromomethyl-5-methoxy-6-methyl-isochroman-3-yl)-piperidine Add 4-trifluoromethylbenzyl bromide (7.2 g) and NMP (20 mL) to REM bound (1R,3S)-4-(1-bromomethyl-5-methoxy-6-methyl-isochroman-3-yl)-piperidine (2.0 g 0.78 mmol/g of loading) in a 50 mL shaking vessel. Shake the reaction mixture at room temperature overnight, filter and wash three times each with NMP, dichloromethane, methanol, and dichloromethane. To this resin add of dichloromethane (18.6 mL) and of DIEA (1.4 mL). Shake the resulting mixture at room temperature overnight, filter and wash the resin twice each with dichloromethane, methanol, and dichloromethane. Combine the filtrates concentrate and add Amberlite IRA-67 (2.0 g) with of dichloromethane (20 mL). Shake the resulting mixture at room temperature for 4 hours, filter and wash twice each with dichloromethane, methanol, and dichloromethane. Combine the filtrates and concentrate to yield the title compound. CIMS 512.1 (MH$^+$), t$_R$ (min)=3.52.

Scheme D, Step D5 (1R,3S)-[3-(1-(4-Trifluoromethylbenzyl)piperidinyl-4-yl)-5-methoxy-6-methyl-isochroman-1-ylmethyl]-dimethylamine Add 2N dimethylamine in methanol (3 mL) to (1R,3S)-1 benzyl-4-(1-bromomethyl-5-methoxy-6-methyl-isochroman-3-yl)-piperidine (30 mg) in an 8 mL vial. Cap the vial, and then stir and heat the reaction mixture at 80° C. for 16 hours. Cool the resulting mixture and concentrate. Purify the crude product on a 1 g SCX column and use the title compound directly for the next step.

Scheme D, Step D6 (1R,3S)-1-Dimethylaminomethyl-6-methyl-)-3-[1-(4-trifluoromethylbenzyl)piperidin-4-yl]-isochroman-5-ol To an 8 mL vial containing (1R,3S)-[3-(1-enzyl-piperidinyl-4-yl)-5-methoxy-6-methyl-isochroman-1-ylmethyl]-dimethylamine from the previous step, add 48% HBr (1 mL). Stir and heat the reaction mixture at 100° C. for three hours. Cool the reaction mixture and concentrate the crude product. Purify the crude product on a 1 g SCX column. Concentrate the appropriate fractions to obtain the title compound. CIMS 463.5 (MH$^+$), t$_R$ (min)=2.75.

The following examples 169-188 were synthesized similarly to Example 68 with different alkylating agents (Step D4) and amines (Step D5) used as reactants.

Example 169

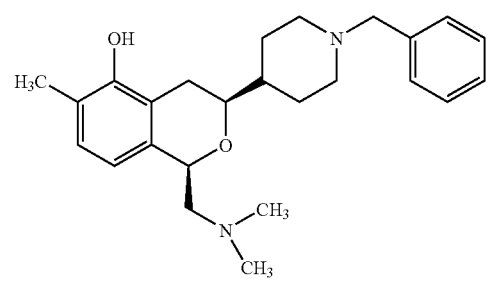

(1R,3S)-3-(1-Benzyl-piperidin-4-yl)-1-dimethylaminomethyl-6-methyl-isochroman-5-ol

| Reactant: Step D4 | Reactant: Step D5 | Retention time t$_R$ (min) of product | CIMS (MH$^+$) of product |
|---|---|---|---|
| Br-CH₂-C₆H₅ | HN(CH$_3$)$_2$ | 2.50 | 395.3 |

Example 170

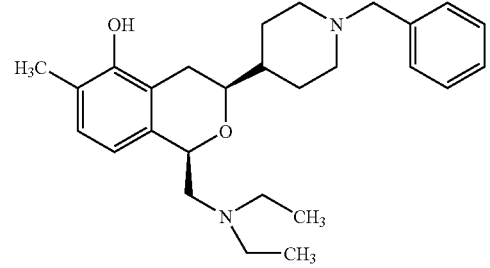

(1R,3S)-3-(1-Benzyl-piperidin-4-yl)-1-diethylaminomethyl-6-methyl-isochroman-5-ol

| Reactant: Step D4 | Reactant: Step D5 | Retention time t$_R$ (min) of product | CIMS (MH$^+$) of product |
|---|---|---|---|
| Br-CH₂-C₆H₅ | HN(C$_2$H$_5$)$_2$ | 2.65 | 423.3 |

Example 171

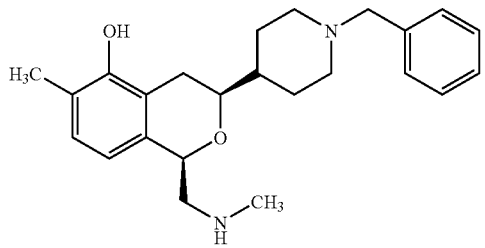

(1R,3S)-3-(1-Benzyl-piperidin-4-yl)-6-methyl-1-methylaminomethyl-isochroman-5-ol

| Reactant: Step D4 | Reactant: Step D5 | Retention time $t_R$ (min) of product | CIMS (MH⁺) of product |
|---|---|---|---|
| Br-CH₂-C₆H₅ | H₂NCH₃ | 2.51 | 381.3 |

Example 173

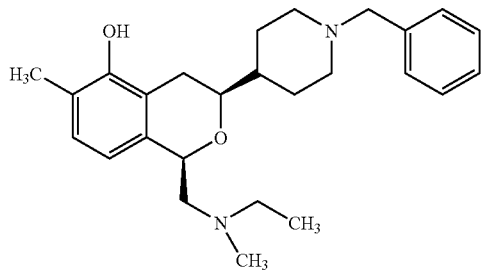

(1R,3S)-3-(1-Benzyl-piperidin-4-yl)-1-[(ethyl-methyl-amino)-methyl]-6-methyl-isochroman-5-ol

| Reactant: Step D4 | Reactant: Step D5 | Retention time $t_R$ (min) of product | CIMS (MH⁺) of product |
|---|---|---|---|
| Br-CH₂-C₆H₅ | HN(CH₃)(C₂H₅) | 2.59 | 409.3 |

Example 172

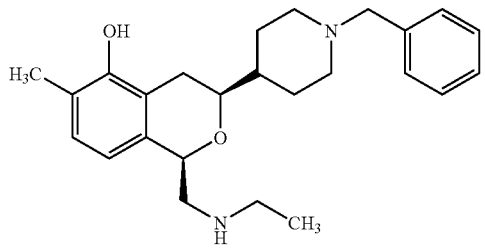

(1R,3S)-3-(1-Benzyl-piperidin-4-yl)-1-ethylaminomethyl-6-methyl-isochroman-5-ol

| Reactant: Step D4 | Reactant: Step D5 | Retention time $t_R$ (min) of product | CIMS (MH⁺) of product |
|---|---|---|---|
| Br-CH₂-C₆H₅ | H₂NC₂H₅ | 2.55 | 395.3 |

Example 174

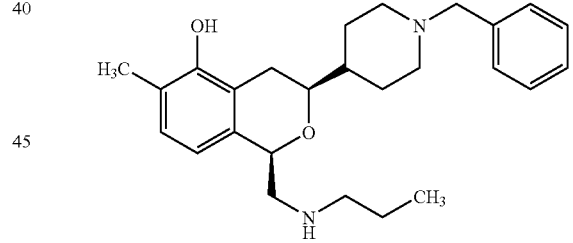

(1R,3S)-3-(1-Benzyl-piperidin-4-yl)-6-methyl-1-propylaminomethyl-isochroman-5-ol

| Reactant: Step D4 | Reactant: Step D5 | Retention time $t_R$ (min) of product | CIMS (MH⁺) of product |
|---|---|---|---|
| Br-CH₂-C₆H₅ | H₂N(CH₂)₂CH₃ | 2.59 | 409.3 |

Example 175

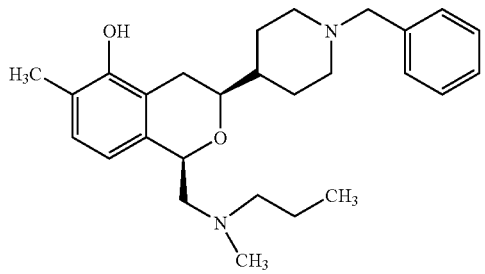

(1R,3S)-3-(1-Benzyl-piperidin-4-yl)-6-methyl-1-[(methyl-propyl-amino)-methyl]-isochroman-5-ol

| Reactant: Step D4 | Reactant: Step D5 | Retention time $t_R$ (min) of product | CIMS (MH$^+$) of product |
|---|---|---|---|
| Br-CH$_2$-C$_6$H$_5$ | HN(CH$_3$)CH$_2$CH$_2$CH$_3$ | 2.67 | 423.3 |

Example 177

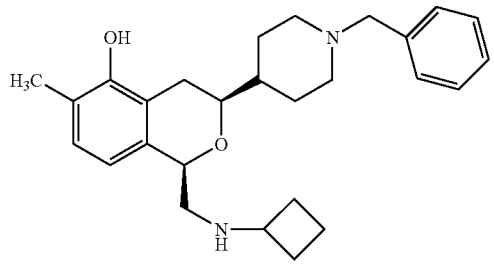

(1R,3S)-3-(1-Benzyl-piperidin-4-yl)-1-cyclobutylaminomethyl-6-methyl-isochroman-5-ol

| Reactant: Step D4 | Reactant: Step D5 | Retention time $t_R$ (min) of product | CIMS (MH$^+$) of product |
|---|---|---|---|
| Br-CH$_2$-C$_6$H$_5$ | H$_2$N-cyclobutyl | 2.67 | 421.3 |

Example 176

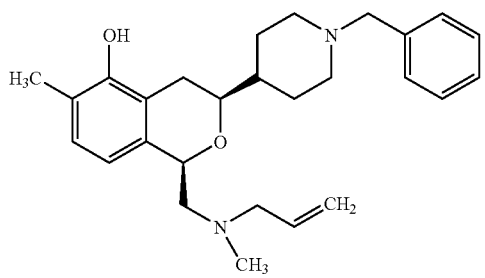

(1R,3S)-1-[(Allyl-methyl-amino)-methyl]-3-(1-benzyl-piperidin-4-yl)-6-methyl-isochroman-5-ol

| Reactant: Step D4 | Reactant: Step D5 | Retention time $t_R$ (min) of product | CIMS (MH$^+$) of product |
|---|---|---|---|
| Br-CH$_2$-C$_6$H$_5$ | HN(CH$_3$)CH$_2$CH=CH$_2$ | 2.65 | 421.3 |

Example 178

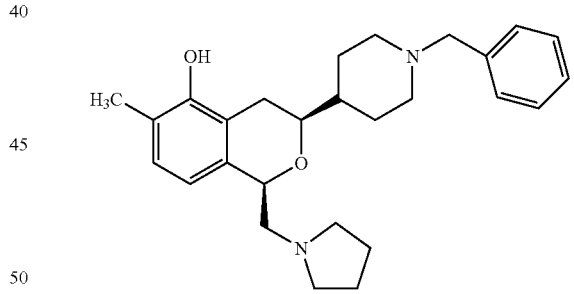

(1R,3S)-3-(1-Benzyl-piperidin-4-yl)-6-methyl-1-pyrrolidin-1-ylmethyl-isochroman-5-ol

| Reactant: Step D4 | Reactant: Step D5 | Retention time $t_R$ (min) of product | CIMS (MH$^+$) of product |
|---|---|---|---|
| Br-CH$_2$-C$_6$H$_5$ | pyrrolidine | 2.67 | 421.3 |

Example 179

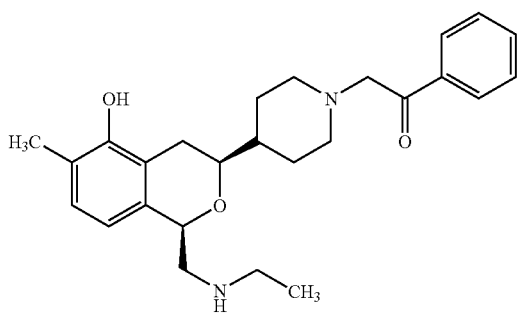

2-[4-((1R,3S)-1-Ethylaminomethyl-5-hydroxy-6-methyl-isochroman-3-yl)-piperidin-1-yl]-1-phenyl-ethanone

| Reactant: Step D4 | Reactant: Step D5 | Retention time $t_R$ (min) of product | CIMS (MH$^+$) of product |
|---|---|---|---|
| Br-CH2-C(O)-Ph | H$_2$NC$_2$H$_5$ | 2.52 | 423.4 |

Example 180

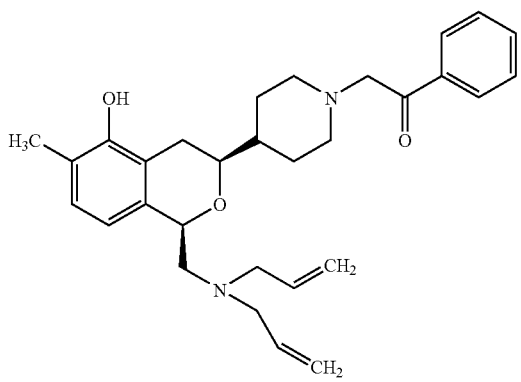

2-[4-((1R,3S)-1-Diallylaminomethyl-5-hydroxy-6-methyl-isochroman-3-yl)-piperidin-1-yl]-1-phenyl-ethanone

| Reactant: Step D4 | Reactant: Step D5 | Retention time $t_R$ (min) of product | CIMS (MH$^+$) of product |
|---|---|---|---|
| Br-CH2-C(O)-Ph | HN(CH2CH=CH2)2 | 2.75 | 475.4 |

Example 181

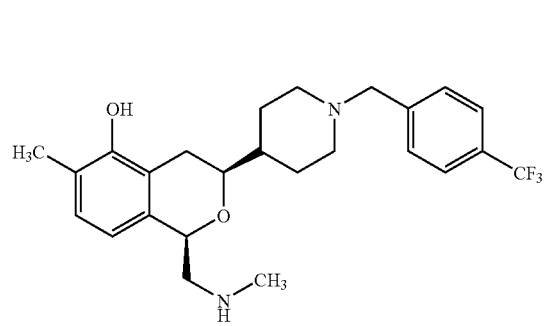

(1R,3S)-6-Methyl-1-methylaminomethyl-3-[1-(4-trifluoromethyl-benzyl)-piperidin-4-yl]-isochroman-5-ol hydrochloride

| Reactant: Step D4 | Reactant: Step D5 | Retention time $t_R$ (min) of product | CIMS (MH$^+$) of product |
|---|---|---|---|
| Br-CH2-C6H4-CF3 | H$_2$NCH$_3$ | 2.36 | 449.4 |

Example 182

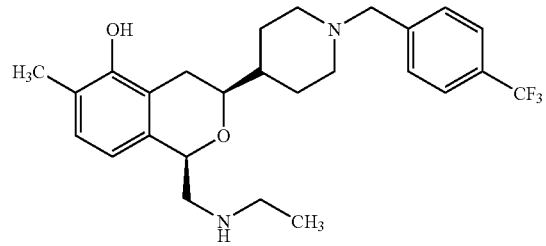

(1R,3S)-1-Ethylaminomethyl-6-methyl-3-[1-(4-trifluoromethyl-benzyl)-piperidin-4-yl]-isochroman-5-ol

| Reactant: Step D4 | Reactant: Step D5 | Retention time $t_R$ (min) of product | CIMS (MH$^+$) of product |
|---|---|---|---|
| Br-CH2-C6H4-CF3 | H$_2$NC$_2$H$_5$ | 2.77 | 463.5 |

Example 183

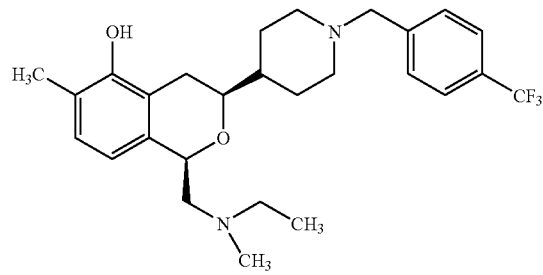

(1R,3S)-1-[(Ethyl-methyl-amino)-methyl]-6-methyl-3-[1-(4-trifluoromethyl-benzyl)-piperidin-4-yl]-isochroman-5-ol

| Reactant: Step D4 | Reactant: Step D5 | Retention time $t_R$ (min) of product | CIMS (MH⁺) of product |
|---|---|---|---|
| | | 2.80 | 477.5 |

Example 184

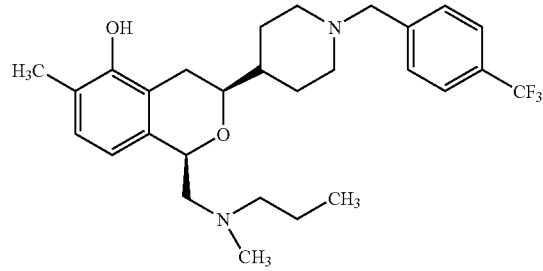

(1R,3S)-6-Methyl-1-[(methyl-propyl-amino)-methyl]-3-[1-(4-trifluoromethyl-benzyl)-piperidin-4-yl]-isochroman-5-ol

| Reactant: Step D4 | Reactant: Step D5 | Retention time $t_R$ (min) of product | CIMS (MH⁺) of product |
|---|---|---|---|
| | | 2.87 | 491.5 |

Example 185

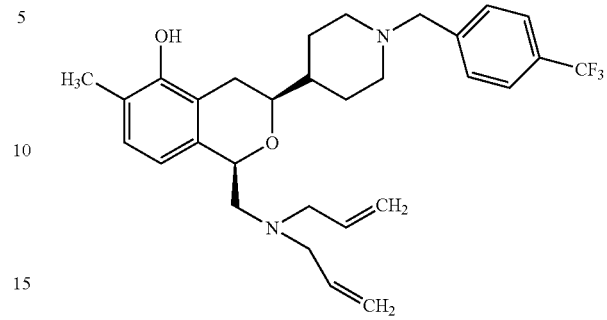

(1R,3S)-1-Diallylaminomethyl-6-methyl-3-[1-(4-trifluoromethyl-benzyl)-piperidin-4-yl]-isochroman-5-ol

| Reactant: Step D4 | Reactant: Step D5 | Retention time $t_R$ (min) of product | CIMS (MH⁺) of product |
|---|---|---|---|
| | | 2.96 | 515.5 |

Example 186

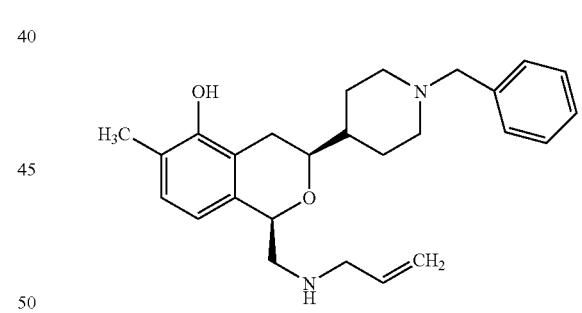

(1R,3S)-1-Allylaminomethyl-3-(1-benzyl-piperidin-4-yl)-6-methyl-isochroman-5-ol

| Reactant: Step D4 | Reactant: Step D5 | Retention time $t_R$ (min) of product | CIMS (MH⁺) of product |
|---|---|---|---|
| | | 2.57 | 407.5 |

Example 187

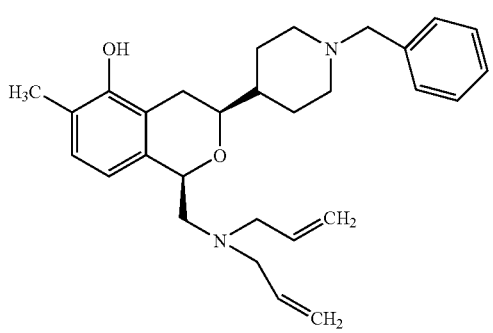

(1R,3S)-3-(1-Benzyl-piperidin-4-yl)-1-diallylaminomethyl-6-methyl-isochroman-5-ol

| Reactant: Step D4 | Reactant: Step D5 | Retention time $t_R$ (min) of product | CIMS (MH+) of product |
|---|---|---|---|
| Br-CH2-Ph | HN(CH2CH=CH2)2 | 2.74 | 447.5 |

Example 188

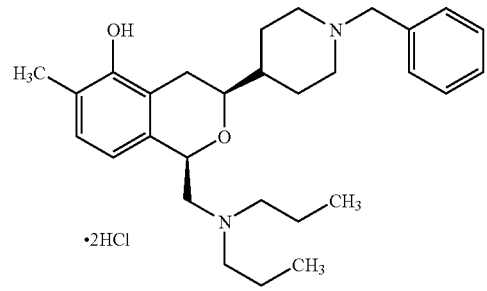

(1R,3S)-3-(1-Benzyl-piperidin-4-yl)-1-dipropylaminomethyl-6-methyl-isochroman-5-ol dihydrochloride

| Reactant: Step D4 | Reactant: Step D5 | Retention time $t_R$ (min) of product | CIMS (MH+) of product |
|---|---|---|---|
| Br-CH2-Ph | HN(CH2CH2CH3)2 | 2.42 | 451.5 |

Example 189

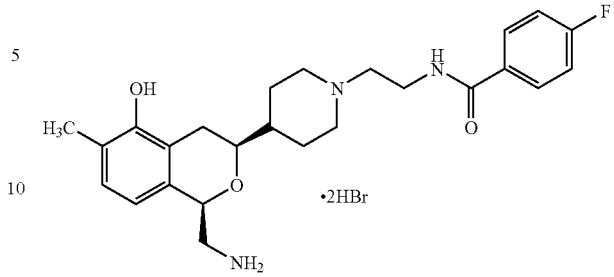

N-{2-[4-((1R,3S)-1-Aminomethyl-5-hydroxy-6-methylisochroman-3-yl)-piperidin-1-yl]ethyl}-4-fluorobenzamide dihydrobromide

Scheme E, Step E1 {2-[4-((1R,3S)-1-Formylaminomethyl-5-methoxy-6-methyl-isochroman-3-yl)-piperidin-1-yl]-ethyl}carbamic acid tert-butyl ester Stir a solution of N-((1R,3S)-5-methoxy-6-methyl-3-(4-piperidinyl)-1-isochromanyl-methyl)formamide (4.0 g, 12.5 mmole) in dichloroethane (110 mL) and add sodium triacetoxyborohydride (4.0 g, 18.8 mmole). Dissolve t-butyl N-(2-oxoethyl)-carbamate (1.0 g, 6.3 mmole) in dichloroethane (20 mL) and add it to the reaction mixture. After 6 hours add another 6.3 mmole of t-butyl N-(2-oxoethyl)-carbamate in dichloroethane. After another 42 hours adjust the pH of the reaction mixture to about 14 with 50% NaOH and extract with dichloromethane. Wash the combined extracts with water and dry over $Mg_2SO_4$. Purify the crude product on a 33 g silica gel column (eluting with ammonium hydroxide:methanol:ethyl acetate 1:1:98). Collect the appropriate fractions and concentrate to obtain the title compound. CIMS 462, $t_R$ (min)=0.46.

Scheme E, Step E2 (1R,3S)-N-{3-[1-(2-Aminoethyl)-piperidin-4-yl]-5-methoxy-6-methylisochroman-1-ylmethyl}formamide dihydrochloride Stir a chilled (5° C.) solution of {2-[4-((1R,3S)-1-formylaminomethyl-5-methoxy-6-methyl-isochroman-3-yl)-piperidin-1-yl]-ethyl}carbamic acid tert-butyl ester (1.8 g, 3.9 mmole) in ethyl acetate (525 mL) and bubble in HCl gas for 5 min. Remove the source of HCl and stir at room temperature for 3 hours. Concentrate the reaction mixture to 200-300 mL, dilute with diethyl ether and collect the resulting solid. CIMS 362.3 $t_R$ (min)=1.02.

Scheme E, Step E3 4-Fluoro-N-{2-[4-((1R,3S)-1-formylaminomethyl-5-methoxy-6-methyl-isochroman-3-yl)-piperidin-1-yl]-ethyl}benzamide (1R,3S)-N-{3-[1-(2-Amino-ethyl)-piperidin-4-yl]-5-methoxy-6-methyl-isochroman-1-ylmethyl}formamide was obtained by distributing the dihydrochloride between aqueous sodium hydroxide and dichloromethane and then evaporating the organic phase. To a mixture of IRA-67 (1.2 g) and (1R,3S)-N-{3-[1-(2-amino-ethyl)-piperidin-4-yl]-5-methoxy-6-methyl-isochroman-1-ylmethyl}formamide (0.3 g, 0.69 mmole) add chloroform (12 mL) and 4-fluorobenzoyl chloride (0.310 g, 1.95 mmole) in chloroform (2 mL). After 24 hours add additional 4-fluorobenzoyl chloride (0.3 g, 1.89 mmole) and IRA-67 (2 g). After an additional 18 hours add PS-trisamine (1.0 g of 3.75 mmole/g) and stir for 6 hours. Filter and concentrate, then flush the product over a 35 g silica gel cartridge (eluting with ammonium hydroxide:methanol: ethyl acetate 1:4:95). Collect the appropriate fraction and concentrate to obtain the title compound. CIMS 484, $t_R$ (min)=0.46.

Scheme E, Step E4 N-{2-[4-((1R,3S)-1-Aminomethyl-5-hydroxy-6-methylisochroman-3-yl)-piperidin-1-yl]ethyl}-4-fluorobenzamide dihydrobromide Stir (1R,3S)-N-[3-(1-{2-[3-(4-fluoro-phenyl)-ureido]ethyl}piperidin-4-yl)-5-methoxy-6-methylisochroman-1-ylmethyl]formamide (0.125 g, 0.26 mmol) and 48% HBr (3 mL) at 100° C. for 2 hours. Concentrate to an oil, dissolve in isopropyl alcohol, and add diethyl ether to precipitate the product. CIMS 442, $t_R$ (min)=0.58.

The following examples 190-191 were synthesized similarly to Example 189 with different acid chlorides in step F3

Example 190

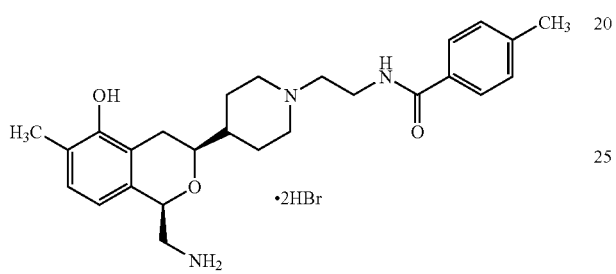

N-{2-[4-((1R,3S)-1-Aminomethyl-5-hydroxy-6-methylisochroman-3-yl)-piperidin-1-yl]-ethyl}-4-methylbenzamide dihydrobromide

| Reactant acid chloride | Retention time $t_R$ (min) of product | ESMS (MH⁺) of product |
|---|---|---|
| 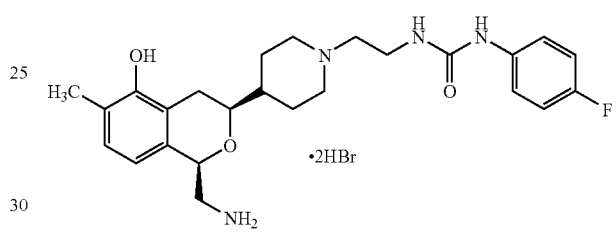 | 1.97 | 438.3 |

Example 191

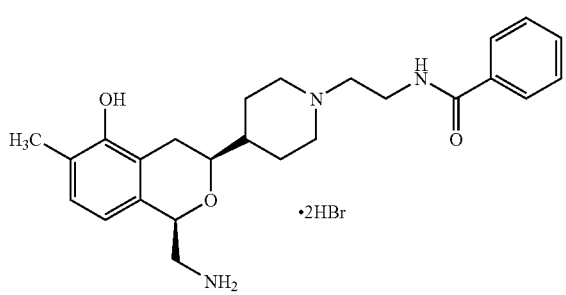

N-{2-[4-((1R,3S)-1-Aminomethyl-5-hydroxy-6-methylisochroman-3-yl)-piperidin-1-yl]-ethyl}benzamide dihydrobromide

| Reactant acid chloride | Retention time $t_R$ (min) of product | ESMS (MH⁺) of product |
|---|---|---|
| (benzoyl chloride structure) | 1.86 | 424.3 |

Example 192

(1R,3S)-1-{2-[4-(1-Aminomethyl-5-hydroxy-6-methyl-isochroman-3-yl)-piperidin-1-yl]ethyl}-3-(4-fluoro-phenyl)urea dihydrobromide

Scheme E, Step E5 N-[3-((1R,3S)-1-{2-[3-(4-Fluoro-phenyl)ureido]ethyl}piperidin-4-yl)-5-methoxy-6-methylisochroman-1-ylmethyl]formamide Dissolve (1R,3S)-N-{3-[1-(2-amino-ethyl)-piperidin-4-yl]-5-methoxy-6-methyl-isochroman-1-ylmethyl}formamide (0.395 g, 1.1 mmole) in chloroform (5 mL) and add 4-fluorophenylisocyanate (0.185 g, 1.3 mmole). Stir for 2 hours, add PS-trisamine (0.425 g of 3.6 mmole/g) and stir 20 hours. Filter, concentrate and purify by flash chromatography over silica gel (eluting with 5% (increasing to 15%) ammonia-saturated methanol in dichloromethane). Collect the appropriate fractions and concentrate to obtain the title compound. CIMS 499.3 $t_R$ (min)=3.01.

Scheme E, Step E6 and E7 1-{2-[4-((1R,3S)-1-Aminomethyl-5-hydroxy-6-methyl-isochroman-3-yl)-piperidin-1-yl]ethyl}-3-(4-fluoro-phenyl)urea dihydrobromide Prepare in analogous fashion to scheme B, steps B3 and B3 above starting from (1R,3S)-N-[3-(1-{2-[3-(4-Fluoro-phenyl)ureido]ethyl}piperidin-4-yl)-5-methoxy-6-methylisochroman-1-ylmethyl]formamide. CIMS 457.4, $t_R$ (min)=0.72.

The following example was synthesized similarly to Example 192 with a different isocyanate in step F5

Example 193

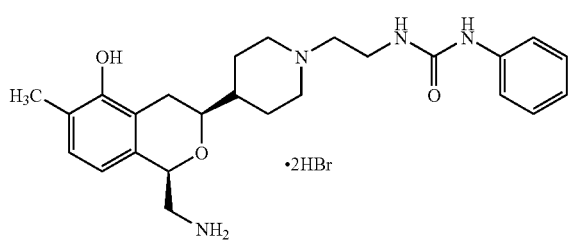

1-{2-[4-((1R,3S)-1-Aminomethyl-5-hydroxy-6-methyl-isochroman-3-yl)piperidin-1-yl]-ethyl}-3-phenylurea dihydrobromide

| Reactant isocyanate | Retention time $t_R$ (min) of product | ESMS (MH$^+$) of product |
|---|---|---|
| ⌬—NCO | 1.95 | 439.3 |

Example 194

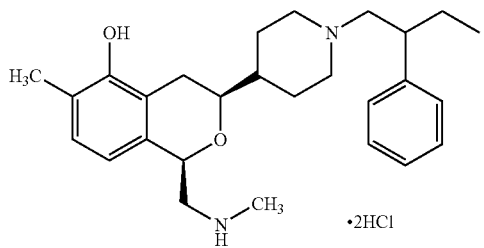

(1R,3S)-6-Methyl-1-methylaminomethyl-3-[1-(2-phenylbutyl)-piperidin-4-yl]isochroman-5-ol dihydrochloride

Scheme E, Step E1 N-{(1R,3S)-5-Isopropoxy-6-methyl-3-[1-(2-phenyl-butyryl)-piperidin-4-yl]-isochroman-1-ylmethyl}formamide Stir a solution of N-((1R,3S)-5-isopropoxy-6-methyl-3-(4-piperidinyl)-1-isochromanyl-methyl)formamide (200 mg, 0.58 mmole) in dichloromethane (3 mL), cool to 10° C. and add 2-phenylbutyryl chloride (115 mg, 0.64 mmole) and triethylamine (88 mg, 0.87 mmole). Allow to warm to room temperature and pour into dilute HCl. Separate the layers an extract the aqueous layer two times with 4 mL of dichloromethane. Wash the combined organic extracts with water and dry over Na$_2$SO$_4$. Purify the crude product on a 10 g silica gel column (eluting with ethyl acetate:heptane 3:1). Collect the appropriate fractions and concentrate to obtain the title compound. It was used without further purification in the next step.

Scheme F, Step F2 {(1R,3S)-5-Isopropoxy-6-methyl-3-[1-(2-phenyl-butyl)-piperidin-4-yl]-isochroman-1-ylmethyl}methyamine Dissolve N-{(1R,3S)-5-isopropoxy-6-methyl-3-[1-(2-phenyl-butyryl)-piperidin-4-yl]-isochroman-1-ylmethyl}formamide (0.10 g, 0.20 mmole) in 1M lithium aluminum hydride in diethyl ether (1.5 mL) and bring to reflux. After 3.5 hr cool to room temperature, add methylene chloride (2 mL) followed by dropwise addition of 10% NaOH until no further reaction is observed. Add 2 mL of methylene chloride and 4 mL of water and filter reaction mixture and wash the filter cake with additional methylene chloride and water. Combine the organic phases and dry over Na$_2$SO$_4$. Purify the crude product on a 4 g silica gel column (eluting with methylene chloride and then methylene chloride:methanol:ammonium hydroxide 89:10:1). Collect the appropriate fractions and concentrate to obtain the title compound. It was used without further purification in the next step.

(1R,3S)-6-Methyl-1-methylaminomethyl-3-[1-(2-phenylbutyl)-piperidin-4-yl]isochroman-5-ol dihydrochloride {(1R,3S)-5-Isopropoxy-6-methyl-3-[1-(2-phenyl-butyl)-piperidin-4-yl]-isochroman-1-ylmethyl}methyamine (0.06 g, 0.13 mmole) was treated with 48% HBr as in Scheme B, step B4 to give the title compound dihydrochloride after treatment with hydrogen chloride in diethyl ether. CIMS 423.2 (NH$^+$), $t_R$ (min)=1.17.

Example 195

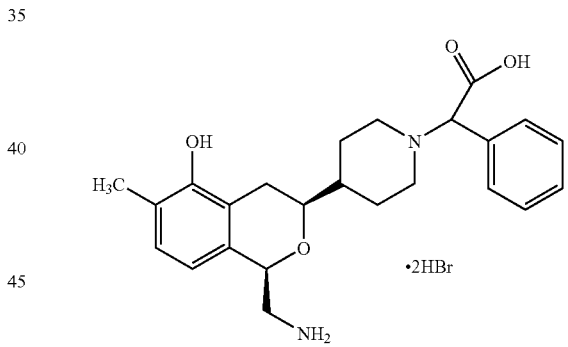

[4-((1R,3S)-1-Aminomethyl-5-hydroxy-6-methyl-isochroman-3-yl)-piperidin-1-yl]-phenylacetic acid dihydrobromide

[4-((1R,3S)-1-Formylaminomethyl-5-hydroxy-6-methyl-isochroman-3-yl)-piperidin-1-yl]-phenyl-acetic acid ethyl ester Stir a solution of N-((1R,3S)-5-methoxy-6-methyl-3-(4-piperidinyl)-1-isochromanyl-methyl)formamide (200 mg, 0.58 mmole), ethyl 2-bromophenylacetate (229 mg, 0.94 mmole) and diisopropylethylamine (243 mg, 1.88 mmole) in acetonitrile overnight at room temperature. Add ethyl acetate and water (2 mL each), then separate the organic phase and dry over Na$_2$SO$_4$. Purify the crude product on a 4 g silica gel column (eluting with ethyl acetate:heptane 3:1). Collect the appropriate fractions and concentrate to obtain the title compound. It was used without further purification in the next step.

[4-((1R,3S)-1-Aminomethyl-5-hydroxy-6-methyl-isochroman-3-yl)-piperidin-1-yl]-phenylacetic acid dihydrobromide

[4-((1R,3S)-1-Formylaminomethyl-5-hydroxy-6-methyl-isochroman-3-yl)-piperidin-1-yl]-phenyl-acetic acid ethyl ester (26 mg, 0.054 mmole) was dissolved in 300 uL of 48% HBr heated at 100° C. After 7 hours the temperature is lowered to 60° C. and the reaction stirred overnight. Add 3 drops of water and collect the precipitated product dihydrobromide. CIMS 411.2 (NH$^+$), $t_R$ (min)=1.13.

Synthesize Examples 196-207 according to the procedure described in Example 111, except perform the hydrolysis of the formylamino group by treatment with 15% aqueous NaOH in methanol/THF at 70° C. instead of 5% methanolic HCl.

Example 196

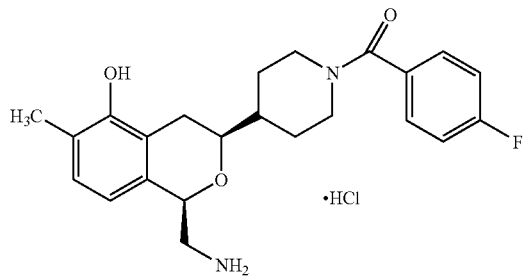

[4-((1R,3S)-1-Aminomethyl-5-hydroxy-6-methyl-isochroman-3-yl)-piperidin-1-yl]-(4-fluoro-phenyl)-methanone hydrochloride

| Reactant acid chloride | Retention time $t_R$ (min) of product | ESMS (MH$^+$) of product |
|---|---|---|
| 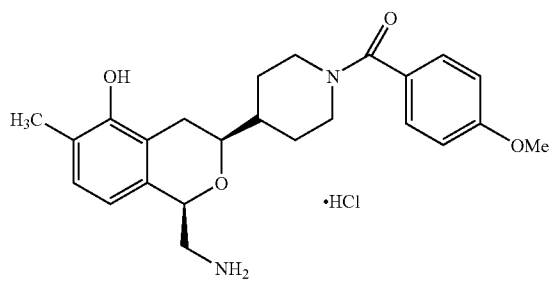 | 2.37 | 399.2 |

Example 197

[4-((1R,3S)-1-Aminomethyl-5-hydroxy-6-methyl-isochroman-3-yl)-piperidin-1-yl]-(4-methoxy-phenyl)-methanone hydrochloride

| Reactant acid chloride | Retention time $t_R$ (min) of product | ESMS (MH$^+$) of product |
|---|---|---|
| 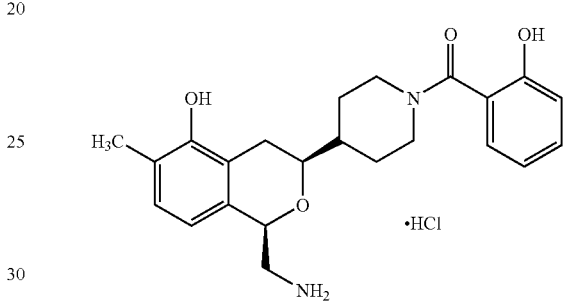 | 2.34 | 411.3 |

Example 198

[4-((1R,3S)-1-Aminomethyl-5-hydroxy-6-methyl-isochroman-3-yl)-piperidin-1-yl]-(2-hydroxy-phenyl)-methanone hydrochloride

| Reactant acid chloride | Retention time $t_R$ (min) of product | ESMS (MH$^+$) of product |
|---|---|---|
| 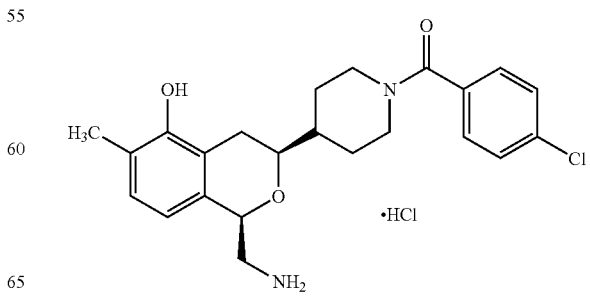 | 2.19 | 397.2 |

Example 199

211

[4-((1R,3S)-1-Aminomethyl-5-hydroxy-6-methyl-isochroman-3-yl)-piperidin-1-yl]-(4-chloro-phenyl)-methanone hydrochloride

| Reactant acid chloride | Retention time $t_R$ (min) of product | ESMS (MH$^+$) of product |
| --- | --- | --- |
| 4-chlorobenzoyl chloride | 2.47 | 415.2 |

Example 200

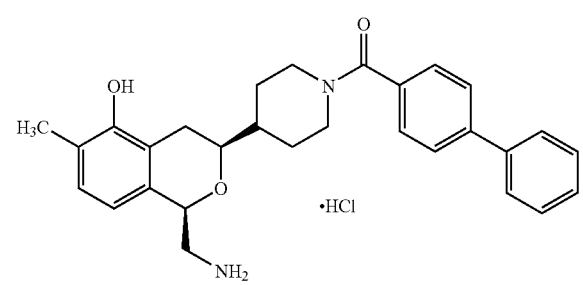

[4-((1R,3S)-1-Aminomethyl-5-hydroxy-6-methyl-isochroman-3-yl)-piperidin-1-yl]-biphenyl-4-yl-methanone hydrochloride

| Reactant acid chloride | Retention time $t_R$ (min) of product | ESMS (MH$^+$) of product |
| --- | --- | --- |
| biphenyl-4-carbonyl chloride | 2.7 | 457.3 |

Example 201

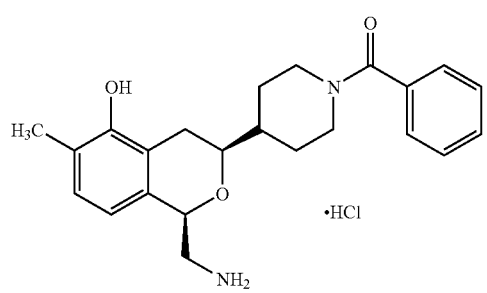

212

[4-((1R,3S)-1-Aminomethyl-5-hydroxy-6-methyl-isochroman-3-yl)-piperidin-1-yl]-phenyl-methanone hydrochloride

| Reactant acid chloride | Retention time $t_R$ (min) of product | ESMS (MH$^+$) of product |
| --- | --- | --- |
| benzoyl chloride | 2.29 | 381.2 |

Example 202

[4-((1R,3S)-1-Aminomethyl-5-hydroxy-6-methyl-isochroman-3-yl)-piperidin-1-yl]-(4-bromo-phenyl)-methanone hydrochloride

| Reactant acid chloride | Retention time $t_R$ (min) of product | ESMS (MH$^+$) of product |
| --- | --- | --- |
| 4-bromobenzoyl chloride | 2.29 | 381.2 |

Example 203

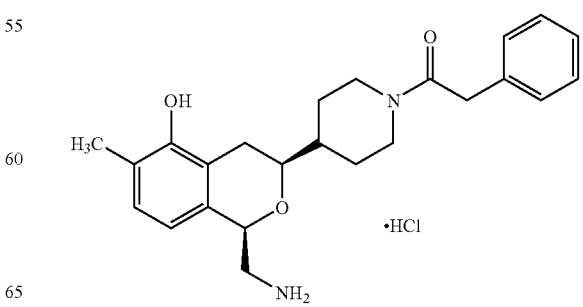

213

1-[4-((1R,3S)-1-Aminomethyl-5-hydroxy-6-methyl-isochroman-3-yl)-piperidin-1-yl]-2-phenyl-ethanone hydrochloride

| Reactant acid chloride | Retention time $t_R$ (min) of product | ESMS (MH$^+$) of product |
|---|---|---|
| 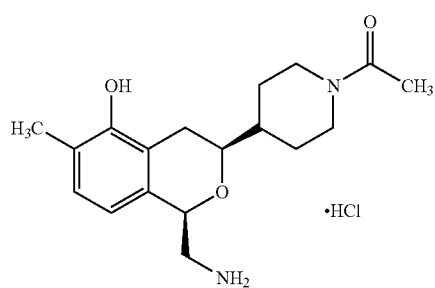 | 2.35 | 395.2 |

Example 204

1-[4-((1R,3S)-1-Aminomethyl-5-hydroxy-6-methyl-isochroman-3-yl)-piperidin-1-yl]-ethanone hydrochloride

| Reactant acid chloride | Retention time $t_R$ (min) of product | ESMS (MH$^+$) of product |
|---|---|---|
| 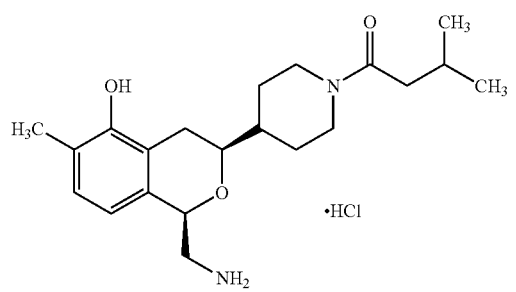 | 1.97 | 319.2 |

Example 205

214

1-[4-((1R,3S)-1-Aminomethyl-5-hydroxy-6-methyl-isochroman-3-yl)-piperidin-1-yl]-3-methyl-butan-1-one hydrochloride

| Reactant acid chloride | Retention time $t_R$ (min) of product | ESMS (MH$^+$) of product |
|---|---|---|
| 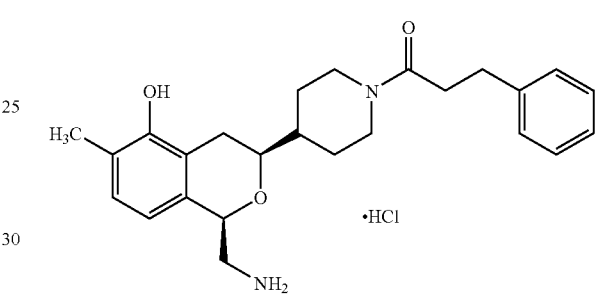 | 2.27 | 361.2 |

Example 206

1-[4-((1R,3S)-1-Aminomethyl-5-hydroxy-6-methyl-isochroman-3-yl)-piperidin-1-yl]-3-phenyl-propan-1-one hydrochloride

| Reactant acid chloride | Retention time $t_R$ (min) of product | ESMS (MH$^+$) of product |
|---|---|---|
| 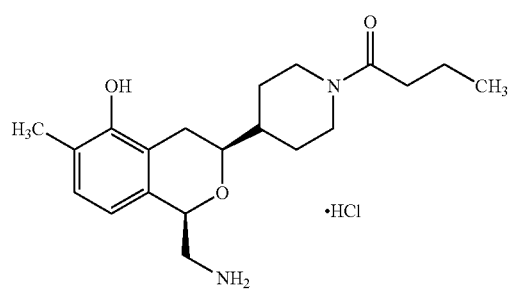 | 2.47 | 409.2 |

Example 207

1-[4-((1R,3S)-1-Aminomethyl-5-hydroxy-6-methyl-isochroman-3-yl)-piperidin-1-yl]-butan-1-one hydrochloride

| Reactant acid chloride | Retention time $t_R$ (min) of product | ESMS (MH$^+$) of product |
|---|---|---|
| 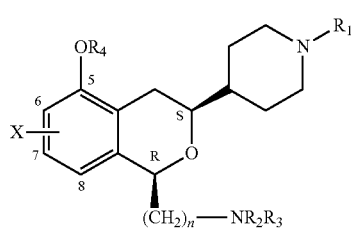 | 2.17 | 347.2 |

What is claimed is:

1. A compound of formula I:

(I)

wherein

R$_1$ is selected from the group consisting of phenylcarbamoylC$_{1-6}$alkyl, naphthylcarbamoylC$_{1-6}$alkyl, naphthylC$_{1-6}$alkyl, C$_{3-6}$cycloalkylC$_{1-6}$alkyl, phenylC$_{1-6}$alkenyl, α-carboxybenzyl, hydroxyC$_{1-6}$alkyl, phenoxyphenylC$_{1-6}$alkyl, and phenylureaC$_{1-6}$alkyl, wherein benzyl and phenyl are optionally substituted with one or two substituents each independently selected from the group consisting of C$_{1-6}$alkyl, C$_{1-6}$ perfluoroalkyl, halogen, hydroxy, C$_1$-C$_6$ alkoxy and nitro;

R$_2$ and R$_3$ are independently selected from the group consisting of hydrogen, C$_{1-6}$alkyl, formyl, C$_{2-6}$alkenyl, and C$_{3-6}$cycloalkylC$_{1-6}$alkyl, or R$_2$ and R$_3$ taken together with the nitrogen atom to which they are attached form a ring of from 2-5 carbon atoms;

R$_4$ is selected from the group consisting of hydrogen and C$_{1-4}$alkyl;

X is C$_{1-6}$alkyl; and n is 1;

or a stereoisomer or a pharmaceutically acceptable salt thereof.

2. The compound according to claim 1 wherein

R$_4$ is selected from the group consisting of hydrogen and C$_{1-4}$alkyl;

or a stereoisomer or a pharmaceutically acceptable salt thereof.

3. The compound according to claim 2 wherein

R$_2$ and R$_3$ are independently selected from the group consisting of hydrogen, C$_{1-3}$alkyl, C$_{2-4}$alkenyl, and C$_{3-6}$cycloalkylC$_{1-3}$alkyl, or R$_2$ and R$_3$ taken together with the nitrogen atom to which they are attached form a ring of from 2-5 carbon atoms;

R$_4$ is selected from the group consisting of hydrogen and C$_{1-3}$alkyl;

X is C$_{1-4}$alkyl; and n is 1;

or a stereoisomer or a pharmaceutically acceptable salt thereof.

4. The compound according to claim 3 wherein

R$_2$ and R$_3$ are hydrogen;

R$_4$ is hydrogen; and

X is C$_{1-3}$alkyl;

or a stereoisomer or a pharmaceutically acceptable salt thereof.

5. The compound according to claim 4 wherein

X is methyl;

or a stereoisomer or a pharmaceutically acceptable salt thereof.

6. The compound according to claim 5 wherein

X is bonded at the 6-position of the ring;

or a stereoisomer or a pharmaceutically acceptable salt thereof.

7. The compound according to claim 1 which is selected from the group consisting of (1R,3S)-1-Aminomethyl-6-methyl-3-[1-(3-phenyl-allyl)-piperidin-4-yl]-isochroman-5-ol, N-{2-[4-((1R,3S)-1-Aminomethyl-5-hydroxy-6-methyl-isochroman-3-yl)-piperidin-1-yl]-ethyl}-benzamide, N-{2-[4-((1R,3S)-1-Aminomethyl-5-hydroxy-6-methyl-isochroman-3-yl)-piperidin-1-yl]-ethyl}-4-fluoro-benzamide, N-{2-[4-((1R,3S)-1-Aminomethyl-5-hydroxy-6-methyl-isochroman-3-yl)-piperidin-1-yl]-ethyl}-4-methyl-benzamide, (1R,3S)-1-Aminomethyl-3-(1-cyclopropylmethyl-piperidin-4-yl)-6-methyl-isochroman-5-ol, 1-{2-[4-((1R,3S)-1-Aminomethyl-5-hydroxy-6-methyl-isochroman-3-yl)-piperidin-1-yl]-ethyl}-3-(4-fluoro-phenyl)-urea;

1-{2-[4-((1R,3S)-1-Aminomethyl-5-hydroxy-6-methyl-isochroman-3-yl)-piperidin-1-yl]-ethyl}-3-phenyl-urea;

(1R,3S)-1-Aminomethyl-6-methyl-3-(1-napthalen-1-yl-methyl-piperidin-4-yl)-isochroman-5-ol, (1R,3S)-1-Aminomethyl-3-[1-(2-hydroxy-ethyl)-piperidin-4-yl]-6-methyl-isochroman-5-ol, (1R,3S)-1-Aminomethyl-6-methyl-3-(1-naphthalen-2-yl-methyl-piperidin-4-yl)-isochroman-5-ol, (1R,3S)-1-Aminomethyl-6-methyl-3-[1-(4-phenoxy-benzyl)-piperidin-4-yl]-isochroman-5-ol, (1R,3S)-3-(1-Cyclohexylmethyl-piperidin-4-yl)-6-methyl-1-methylaminomethyl-isochroman-5-ol, N-{3-[4-((1R,3S)-1-Aminomethyl-5-hydroxy-6-methyl-isochroman-3-yl)-piperidin-1-yl]-1-methyl-propyl}-4-chloro-benzamide, N-{3-[4-((1R,3S)-1-Aminomethyl-5-hydroxy-6-methyl-isochroman-3-yl)-piperidin-1-yl]-1-ethyl-2-methyl-propyl}-4-methyl-benzamide, N-{3-[4-((1R,3S)-1-Aminomethyl-5-hydroxy-6-methyl-isochroman-3-yl)-piperidin-1-yl]-1-methyl-propyl}-4-methyl-benzamide, N-{3-[4-((1R,3S)-1-Aminomethyl-5-hydroxy-6-methyl-isochroman-3-yl)-piperidin-1-yl]-1-methyl-propyl}-4-trifluoromethyl-benzamide, N-{3-[4-((1R,3S)-1-Aminomethyl-5-hydroxy-6-methyl-isochroman-3-yl)-piperidin-1-yl]-1-methyl-propyl}-2,4-dichloro-benzamide, Biphenyl-4-carboxylic acid {3-[4-((1R,3S)-1-aminomethyl-5-hydroxy-6-methyl-isochroman-3-yl)-piperidin-1-yl]-1-methyl-propyl}-amide, Benzo[b]thiophene-2-carboxylic acid {3-[4-((1R,3S)-1-aminomethyl-5-hydroxy-6-methyl-isochroman-3-yl)-piperidin-1-yl]-1-methyl-propyl}-amide, N-{3-[4-((1R,3S)-1-Aminomethyl-5-hydroxy-6-methyl-isochroman-3-yl)-piperidin-1-yl]-1-methyl-propyl}-benzamide, N-{3-[4-((1R,3S)-1-Aminomethyl-5-hydroxy-6-methyl-isochroman-3-yl)-piperidin-1-yl]-1-methyl-propyl}-4-fluoro-benzamide, N-{3-[4-((1R,3S)-1-Aminomethyl-5-hydroxy-6-methyl-isochroman-3-yl)-piperidin-1-yl]-1-methyl-propyl}-4-bromo-benzamide, N-{3-[4-((1R,3S)-1-Aminomethyl-5-hydroxy-6-methyl-isochroman-3-yl)-piperidin-1-yl]-1-methyl-propyl}-4-nitro-benzamide, Naphthalene-2-carboxylic acid {3-[4-((1R,3S)-1-aminomethyl-5-hydroxy-6-methyl-isochroman-3-yl)-piperidin-1-yl]-1-methyl-propyl}-amide dihydrochloride, and Thiophene-2-carboxylic acid {3-[4-((1R,3S)-aminomethyl-5-hydroxy-6-methyl-isochroman-3-yl)-piperidin-1-yl]-1-methyl-propyl}-amide, or a stereoisomer or a pharmaceutically acceptable salt thereof.

8. A pharmaceutical composition comprising a pharmaceutically acceptable carrier and a therapeutically effective amount of the compound according to claim 1 or a stereoisomer or a pharmaceutically acceptable salt thereof.

9. A method for treating Parkinson's disease comprising the administering to a patient in need of such treatment a therapeutically effective amount of the compound according to claim 1 or a stereoisomer or a pharmaceutically acceptable salt thereof.

10. A method for treating an extra-pyramidal side effect associated with the use of an neuroleptic agent, comprising administering to a patient in need of such treatment a therapeutically effective amount of the compound according to claim 1 or a stereoisomer or a pharmaceutically acceptable salt thereof.

* * * * *